US008919957B2

(12) United States Patent
Zhou et al.

(10) Patent No.: US 8,919,957 B2
(45) Date of Patent: Dec. 30, 2014

(54) APPARATUS AND METHOD FOR OPERATING A REAL TIME LARGE DIOPTER RANGE SEQUENTIAL WAVEFRONT SENSOR

(71) Applicant: Clarity Medical Systems, Inc., Pleasanton, CA (US)

(72) Inventors: Yan Zhou, Pleasanton, CA (US); Bradford Chew, San Ramon, CA (US); William Shea, Pleasanton, CA (US)

(73) Assignee: Clarity Medical Systems, Inc., Pleasanton, CA (US)

( * ) Notice: Subject to any disclaimer, the term of this patent is extended or adjusted under 35 U.S.C. 154(b) by 0 days.

(21) Appl. No.: 14/074,060

(22) Filed: Nov. 7, 2013

(65) Prior Publication Data

US 2014/0055749 A1 Feb. 27, 2014

Related U.S. Application Data

(60) Continuation-in-part of application No. 13/745,738, filed on Jan. 18, 2013, now Pat. No. 8,678,591, which is a continuation of application No. 13/198,442, filed on Aug. 4, 2011, now Pat. No. 8,356,900, which is a continuation-in-part of application No. 12/790,301, filed on May 28, 2010, now Pat. No. 8,579,437, which is a division of application No. 11/761,890, filed on Jun. 12, 2007, now Pat. No. 7,815,310, which is a continuation-in-part of application No. 11/335,980, filed on Jan. 20, 2006, now Pat. No. 7,445,335, application No. 14/074,060, which is a continuation-in-part of application No. 13/902,716, filed on May 24, 2013, now Pat. No. 8,827,452, which is a continuation of application No. 13/354,763, filed on Jan. 20, 2012, now Pat. No. 8,454,162, which is a continuation of application No. 12/605,219, filed on Oct. 23, 2009, now Pat. No. 8,100,530, which is a continuation-in-part of application No. 11/761,890, filed on Jun. 12, 2007, now Pat. No. 7,815,310, which is a continuation-in-part of application No. 11/335,980, filed on Jan. 20, 2006, now Pat. No. 7,445,335.

(60) Provisional application No. 61/723,531, filed on Nov. 7, 2012.

(51) Int. Cl.
*A61B 3/10* (2006.01)
*G01J 9/00* (2006.01)
*G01J 3/06* (2006.01)
*A61F 9/008* (2006.01)

(52) U.S. Cl.
CPC ............ *A61B 3/1015* (2013.01); *A61B 3/102* (2013.01); *G01J 9/00* (2013.01); *G01J 2003/064* (2013.01); *A61F 2009/00848* (2013.01)
USPC ............ 351/205; 351/210; 351/212; 351/214

(58) Field of Classification Search
CPC .... A61B 3/1015; A61B 3/102; A61B 3/1025; A61B 3/13; A61B 3/1035
USPC .................. 351/205, 210, 211, 212, 214, 246
See application file for complete search history.

(56) References Cited

U.S. PATENT DOCUMENTS 4,141,652 A 2/1979 Feinleib
5,164,578 A 11/1992 Witthoft et al.
(Continued)

FOREIGN PATENT DOCUMENTS

EP 1 967 864 A2 9/2008
GB 2 399 627 A 9/2004
(Continued)

OTHER PUBLICATIONS

Dave, T., "Wavefront Aberrometry Part 1: Current Theories and Concepts", Optometry Today, Nov. 19, 2004, pp. 41-45.
(Continued)

*Primary Examiner* — Huy K Mai
(74) *Attorney, Agent, or Firm* — Kilpatrick Townsend Stockton LLP; James K. Chang, Esq.

(57) ABSTRACT

A sequential wavefront sensor includes a light source, a beam deflecting element, a position sensing detector configured to output a plurality of output signals and a plurality of composite transimpedance amplifiers each coupled to receive an output signal. The output of each composite transimpedance amplifier is phase-locked to a light source drive signal and a beam deflecting element drive signal.

4 Claims, 35 Drawing Sheets

(56) References Cited

U.S. PATENT DOCUMENTS

| | | | |
|---|---|---|---|
| 5,258,791 A * | 11/1993 | Penney et al. | 351/211 |
| 5,345,281 A | 9/1994 | Taboada et al. | |
| 5,457,310 A | 10/1995 | Fournier | |
| 5,568,208 A | 10/1996 | Van de Velde | |
| 5,651,600 A | 7/1997 | Dorsey-Palmateer | |
| 5,777,719 A | 7/1998 | Williams | |
| 6,199,986 B1 | 3/2001 | Williams et al. | |
| 6,376,819 B1 | 4/2002 | Neal et al. | |
| 6,409,345 B1 | 6/2002 | Molebny | |
| 6,530,917 B1 | 3/2003 | Seiler | |
| 6,578,963 B2 | 6/2003 | Pettit | |
| 6,595,642 B2 | 7/2003 | Wirth | |
| 6,685,317 B2 | 2/2004 | Su et al. | |
| 6,709,108 B2 | 3/2004 | Levine et al. | |
| 6,736,510 B1 | 5/2004 | Van Heugten | |
| 6,781,681 B2 | 8/2004 | Horwitz | |
| 6,784,408 B1 | 8/2004 | Cheung | |
| 6,791,696 B1 | 9/2004 | Fantone et al. | |
| 6,793,654 B2 | 9/2004 | Lemberg | |
| 6,827,444 B2 | 12/2004 | Williams et al. | |
| 6,880,933 B2 | 4/2005 | Davis | |
| 6,890,076 B2 | 5/2005 | Roorda | |
| 6,910,770 B2 | 6/2005 | Campbell | |
| 6,932,475 B2 | 8/2005 | Molebny | |
| 6,964,480 B2 | 11/2005 | Levine | |
| 7,284,862 B1 | 10/2007 | Lai | |
| 7,414,712 B2 | 8/2008 | Yoon | |
| 7,554,672 B2 | 6/2009 | Greenaway | |
| 7,665,846 B2 | 2/2010 | Campin et al. | |
| 7,771,048 B2 | 8/2010 | Dai et al. | |
| 7,988,291 B2 | 8/2011 | Ianchulev | |
| 8,002,410 B2 | 8/2011 | Shea | |
| 8,356,900 B2 | 1/2013 | Zhou et al. | |
| 8,454,162 B2 | 6/2013 | Zhou et al. | |
| 8,579,437 B2 | 11/2013 | Su et al. | |
| 8,591,027 B2 | 11/2013 | Su et al. | |
| 8,678,591 B2 | 3/2014 | Zhou et al. | |
| 2001/0019361 A1 | 9/2001 | Savoye | |
| 2002/0159030 A1 | 10/2002 | Frey et al. | |
| 2002/0169441 A1 | 11/2002 | Lemberg | |
| 2003/0038921 A1 | 2/2003 | Neal et al. | |
| 2003/0053031 A1 | 3/2003 | Wirth | |
| 2003/0063257 A1 | 4/2003 | Molebny | |
| 2003/0086063 A1 | 5/2003 | Williams et al. | |
| 2003/0174281 A1 | 9/2003 | Herekar et al. | |
| 2003/0223037 A1 | 12/2003 | Chernyak | |
| 2004/0004696 A1 | 1/2004 | Davis et al. | |
| 2004/0008321 A1 | 1/2004 | Saigusa et al. | |
| 2004/0156015 A1 | 8/2004 | Campbell | |
| 2004/0239876 A1 | 12/2004 | Levine | |
| 2005/0094100 A1 | 5/2005 | Ross et al. | |
| 2005/0134851 A1 | 6/2005 | Murphy | |
| 2006/0077347 A1 | 4/2006 | Liang | |
| 2007/0171366 A1 | 7/2007 | Su et al. | |
| 2008/0284979 A1 | 11/2008 | Yee et al. | |
| 2009/0185132 A1 | 7/2009 | Raymond | |
| 2010/0231858 A1 | 9/2010 | Su et al. | |
| 2010/0271595 A1 * | 10/2010 | Molebny | 351/221 |
| 2011/0164220 A1 | 7/2011 | Su et al. | |
| 2012/0026466 A1 | 2/2012 | Zhou et al. | |
| 2012/0069303 A1 | 3/2012 | Seesselberg | |
| 2012/0188506 A1 | 7/2012 | Zhou et al. | |
| 2012/0238904 A1 | 9/2012 | Manns et al. | |
| 2012/0268717 A1 | 10/2012 | Zhou et al. | |
| 2013/0265541 A1 | 10/2013 | Zhou | |

FOREIGN PATENT DOCUMENTS

| | | |
|---|---|---|
| WO | 03/073121 A1 | 9/2003 |
| WO | 2004/021875 A1 | 3/2004 |
| WO | 2007/087058 A1 | 8/2007 |

OTHER PUBLICATIONS

"Hands-on Internet Photodiode Sensing Using the Internet, Cyril Bateman Has Been Examining the Benefits of Transimpedance Amplifiers Over Transconductance Amplifiers When Measuring Light Using a Photodiode," Electronics World, Nexus Media Communications, Swanley, Kent GB, vol. 106, No. 1767, pp. 210-215, Mar. 2000.

Abado, Shaddy, "Two-dimensional high-bandwidth Shack-Hartmann wavefront sensor: design guidelines and evaluation testing," Optical Engineering, 2010, vol. 49, No. 6, pp. 064403.

Abado, Shaddy, "Designing and testing a high-bandwidth 2-D wavefront sensor for Aero-optics," Proc. SPIE, Advanced Wavefront Control: Methods, Devices, and Applications VII, Aug. 11, 2009, vol. 7466.

De Lima Monteiro, D.W. et al., "Fast Hartmann-Shack Wavefront Sensors Manufactured in Standard CMOS Technology," IEEE Sensors Journal, IEEE Service Center, New York, NY, Oct. 1, 2005, vol. 5, No. 5, pp. 976-982.

Rana, N.K., "A Non-contact Method for Rod Straightness Measurement Based on Quadrant Laser Sensor," Industrial Technology, 2006, ICIT 2006, IEEE International Conference on IEEE, PI, Dec. 1, 2006, pp. 2292-2297.

"Transimpedanzverstärker," Wikipedia, Apr. 25, 2012, retrieved from the Internet: http://de.wikipedia.org/w/index.php?title-Transimpedanzverst%C3%A4rker&oldid=102459149 [retrieved on Jan. 31, 2014] section "Anwendung".

Vera-Marquina, A. et al., "Quadrant photodiode for electronic processing," Proc. SPIE 7419, Infrared Systems and Photoelectronic Technology IV, 74190Z, vol. 7419, Aug. 2, 2009, pp. 74190Z-3 to 74190Z-4.

Brockington, Samuel et al., "Plasma density gradient measurement using laser deflection," Review of Scientific Instruments, AIP, Melville, NY, vol. 76, No. 6, Jun. 6, 2005, 063503, 7 pages.

Ginis, H.S. et al., Variability of wavefront aberration measurements in small pupil sizes using a clinical Shack-Hartmann aberrometer, BMC Ophthalmology, Feb. 11, 2004, 4:1.

Goodman, J., "Introduction to Fourier Optics, Second Edition," The McGraw-Hill Companies, Inc., 1998, pp. 232-233, 273-274.

Liang, J. et al., "Objective measurements of wave aberrations of the human eye with the use of a Hartmann-Shack wavefront sensor," J. Opt. Soc. Am. A., vol. 11, No. 7, Jul. 1994, pp. 1949-1957.

Wei, Xin et al., "Design and validation of a scanning Shack-Hartmann aberrometer for measurements of the eye over a wide field of view," Optics Express, OSA, Jan. 18, 2010, vol. 18, No. 2, pp. 1-10.

Widiker, J. et al., "High speed Shack-Hartmann wavefront sensor design with commercial off-the-shelf optics," Applied Optics, vol. 45, Jan. 2006, pp. 393-395.

* cited by examiner

Wavefront Source being measured

Wavefront Source being measured

Wavefront Source being measured

Wavefront Source being measured

Divergent Spherical: Positive Axes     Convergent Spherical: Negative Axes

APPARATUS AND METHOD FOR OPERATING A REAL TIME LARGE DIOPTER RANGE SEQUENTIAL WAVEFRONT SENSOR

CROSS-REFERENCE TO RELATED APPLICATIONS

This application is a continuation-in-part of U.S. application Ser. No. 13/745,738 filed Jan. 18, 2013, which is a continuation of U.S. application Ser. No. 13/198,442 filed Aug. 4, 2011 (now U.S. Pat. No. 8,356,900 issued Jan. 22, 2013), which is a continuation-in-part of U.S. application Ser. No. 12/790,301 filed May 28, 2010, which is a division of U.S. application Ser. No. 11/761,890 filed Jun. 12, 2007, (now U.S. Pat. No. 7,815,310 issued Oct. 19, 2010), which is a continuation-in-part of U.S. application Ser. No. 11/335,980 filed Jan. 20, 2006 (now U.S. Pat. No. 7,445,335 issued Nov. 4, 2008); this application is a continuation-in-part of U.S. application Ser. No. 13/902,716 filed May 24, 2013, which is a continuation of U.S. application Ser. No. 13/354,763 filed Jan. 20, 2012, (now U.S. Pat. No. 8,454,162 issued Jun. 4, 2013), which is a continuation of U.S. application Ser. No. 12/605,219 filed Oct. 23, 2009, (now U.S. Pat. No. 8,100,530 issued Jan. 24, 2012), which is a continuation-in-part of U.S. application Ser. No. 11/761,890 filed Jun. 12, 2007, (now U.S. Pat. No. 7,815,310 issued Oct. 19, 2010), which is a continuation-in-part of U.S. application Ser. No. 11/335,980 filed Jan. 20, 2006 (now U.S. Pat. No. 7,445,335 issued Nov. 4, 2008); this application claims the benefit of priority to U.S. provisional application Ser. No. 61/723,531 filed Nov. 7, 2012, each of which are incorporated by reference in its entirety.

TECHNICAL FIELD OF THE INVENTION

One or more embodiments of the present invention relate generally to wavefront sensor(s) for use in vision correction procedures. In particular, the invention relates to the electronics and algorithms for driving, controlling and processing the data of a real-time sequential wavefront sensor and other subassemblies associated with the wavefront sensor.

BACKGROUND OF THE INVENTION

Conventional wavefront sensors for human eye wavefront characterization are generally designed to take a snap shot or several snap shots of a patient's eye wavefront with room lighting turned down or off. These wavefront sensors generally use a CCD or CMOS image sensor to capture the wavefront data and need to use relatively complicated data processing algorithms to figure out the wavefront aberrations. Due to the fact that a CCD or CMOS image sensor generally has a limited number of gray scales and cannot be operated at a frame rate well above the 1/f noise range, these wavefront sensors therefore cannot take full advantage of lock-in detection scheme to provide higher signal to noise ratio. They cannot employ a simple algorithm to quickly derive the wavefront aberration. As a result, when these wavefront sensors are integrated with an ophthalmic device such as a surgical microscope, they generally cannot provide accurate/repeatable real time wavefront aberration measurement, especially with the microscope's illumination light turned on.

There is a need in the art for an apparatus and a method to not only realize real time wavefront measurement and display, but also address the various issues including what has been mentioned above.

SUMMARY OF THE INVENTION

One or more embodiments satisfy one or more of the above-identified needs in the art. In particular, one embodiment is an electronic control and driving circuit together with associated algorithm and software for driving, controlling and processing the data of a real-time sequential wavefront sensor to achieve various functions.

The circuit includes an opto-electronic position sensing detector/device (PSD) such as a quadrant photodiode/detector/cell/sensor or a lateral effect position sensing detector, a transimpedance amplifier, an Analog to Digital (A/D) converter, a digital amplifier with programmable gain control, a superluminescent diode (SLD or SLED) and its drive circuit, a wavefront scanning/shifting device and its driver circuit, and a front-end data processing unit (e.g. processor, microcontroller, PGA, programmable device). In addition, a camera is used to provide live video images of the eye from which the wavefront is being measured. Furthermore, a back-end data processing unit is employed to convert the sequential wavefront data from the front-end processing unit to display clinical ophthalmic information overlaid on or side-by-side with a live image of the patient's eye. The circuits (frontend and/or backend) can be electronically connected to one or more various devices in one way or another for coordinated operation of each device, including for example, an eye transverse position measurement device, an eye distance measurement device, an accommodation enabling eye fixation target, a data storage device, a laser based surgical ablation device, and a display device.

One embodiment of the present disclosure is to use a variable gain amplifier between the transimpedance amplifier and the A/D converter in the above-mentioned circuit to realize a large signal strength measurement over a larger signal strength dynamic range. The need for such a large signal strength measurement dynamic range arises from the need to measure both weak and strong wavefront signals for various eye or environmental conditions, such as a dense cataract eye versus an aphakic eye, or a long eye versus a short eye, or large distance from the eye, or bright external illumination Another embodiment of the disclosure is to use a composite amplifier with a high impedance feedback resistor as part of the transimpedance amplifier to maximize signal-to-noise ratio, reduce electronic noise, and maintain amplifier stability without reducing gain-bandwidth product.

Still another embodiment of the disclosure is to combine a composite transimpedance amplifier with a lock-in detection circuit to recover small signals which would otherwise be obscured by noise sources much larger than the signal of interest.

Still another embodiment is a wavefront sensor that includes a light source configured to output a light beam to illuminate a subject eye, a light source driver circuit, coupled to the light source, configured to output a light source drive signal at a first pulsing frequency, a position sensitive detector having a plurality of detector elements configured to output a plurality of detector output signals indicating signal strength of incident light on each detector element, a first beam deflecting element configured to intercept a wavefront beam returned from a subject eye when the subject eye is illuminated by the light source and configured to direct a portion of the wavefront from the subject eye through an aperture toward the detector, where the portion of the wavefront directed through the aperture forms a spot on the detector and with amplitude of deflection of a centroid of the spot from a reference point on the detector approximately indicated by a ratiometric combination of the signal strengths and with the amplitude of the deflection indicating the degree of tilt or convergence or divergence of the portion of the wavefront from a plane wave, a beam deflecting element driving circuit 720, coupled to the first beam deflecting element, configured to output a beam deflecting element drive signal to scan the portion of the wavefront at a wavefront scanning frequency and a plurality of composite transimpedance amplifiers, each having an input coupled to receive one of the plurality of detector output signals and an output for providing an amplified detector output signal, with the output of each transimpedance amplifier phase-locked to the light source drive signal and the beam deflecting element drive signal.

These and other features and advantages of the present invention will become more readily apparent to those skilled in the art upon review of the following detailed description of the preferred embodiments taken in conjunction with the accompanying drawings.

DETAILED DESCRIPTION OF THE INVENTION

Figure 1:
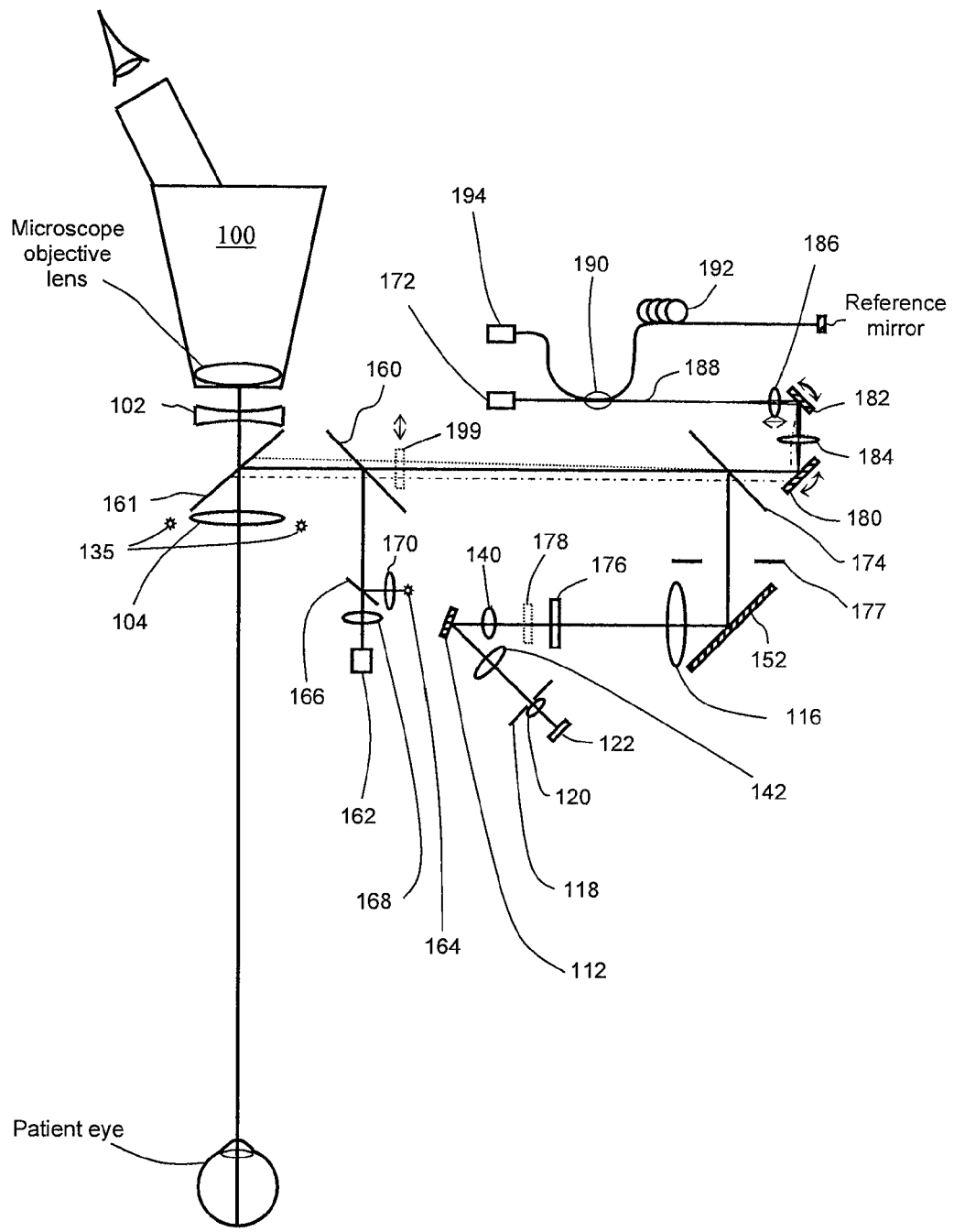
FIG. 1 shows one example embodiment of the optical configuration of a large diopter range real time sequential wavefront sensor integrated with a surgical microscope.

Reference will now be made in detail to various embodiments of the invention. Examples of these embodiments are illustrated in the accompanying drawings. While the invention will be described in conjunction with these embodiments, it will be understood that it is not intended to limit the invention to any embodiment. On the contrary, it is intended to cover alternatives, modifications, and equivalents as may be included within the spirit and scope of the invention as defined by the appended claims. In the following description, numerous specific details are set forth in order to provide a thorough understanding of the various embodiments. However, the present invention may be practiced without some or all of these specific details. In other instances, well known process operations have not been described in detail in order not to unnecessarily obscure nor apply limitations to the present invention. Further, each appearance of the phrase an "example embodiment" at various places in the specification does not necessarily refer to the same example embodiment.

In a typical wavefront sensor used for the measurement of wavefront aberration of a human eye, the wavefront from the eye pupil or cornea plane is generally relayed to a wavefront sensing or sampling plane using the well known 4-F relay principle once or multiple times (see for example, J. Liang, et al. (1994) "Objective measurement of the wave aberrations of the human eye with the use of a Hartmann-Shack wave-front sensor," J. Opt. Soc. Am. A 11, 1949-1957; J. J. Widiker, et al. (2006) "High-speed Shack-Hartmann wavefront sensor design with commercial off-the-shelf optics," Applied Optics, 45(2), 383-395; U.S. Pat. No. 7,654,672). Such a single or multiple 4-F relay system will preserve the phase information of the incident wavefront while allowing it to be relayed without detrimental propagation effects. In addition, by configuring an afocal imaging system using two lenses of different focal lengths to realize the 4-F relay, the relay can allow for the magnification or demagnification of the incident wavefront with an associated demagnification or magnification of the divergence or convergence of the incident wavefront (see for example, J. W. Goodman, *Introduction to Fourier Optics,* $2^{nd}$ ed. McGraw-Hill, 1996).

In recent years, it has been realized that there is a need for a real time wavefront sensor to provide live feedback for various vision correction procedures such as LRI/AK refinement, Laser Enhancement, and cataract/refractive surgery. For these procedures, it has been realized that any interference to a normal surgical operation is undesirable, especially the turning off of the surgical microscope's illumination light and a waiting period for wavefront data capturing and processing. Surgeons want a real time feedback to be provided to them as the vision correction procedure is being normally performed. In addition, most surgeons also prefer that the real time wavefront measurement results being displayed continuously is synchronized and superimposed onto or displayed side-by-side next to a real time video display/movie of the eye, with the overlaid or side-by-side-displayed wavefront measurement results shown in a qualitative or a quantitative or a combined qualitative/quantitative manner. Another main issue is the movement of the eye relative to the wavefront sensor during a vision correction surgical procedure while the wavefront is being measured in real time. Previous wavefront sensors do not provide means to compensate for eye movement; instead, they require the eye to be re-aligned to the wavefront sensor for meaningful wavefront measurement.

In a co-pending patent application (US20120026466) assigned to the same assignee of this patent application, a large diopter range sequential wavefront sensor especially suitable for addressing the issues encountered during a vision correction procedure has been disclosed. Although details of many optical design/configuration possibilities have been disclosed in that co-pending patent application, the electronics control and data processing details for operating such a large diopter range sequential wavefront sensor have not been disclosed. Additional measurement capabilities of different subassemblies have not been discussed in detail. In the present disclosure, various features of the electronics control and driving aspects and the associated algorithm(s) for achieving various functions are disclosed.

In accordance with one or more embodiments of the present invention, a lock-in detection electronics system associated with related algorithms for achieving high precision wavefront measurement is disclosed. The electronics system obtains its electronic signal from an opto-electronic position sensing device/detector; it amplifies the analog signal with a composite trans-impedance amplifier, converts the analog signal to a digital signal via an A/D converter, amplifies the digital signal via a digital amplifier, and processes the data via a data processing unit. The electronics system is connected to some or all of those electronically active devices of the wavefront sensor module to achieve different functionalities. Examples of these active devices include a light source such as a superluminescent diode (SLD) for generating the object wavefront to be measured, a SLD beam focusing and/or steering module, a wavefront scanning/shifting device such as a MEMS scan mirror, an eye pupil transverse position and distance sensing/measurement device, an eye fixation target, various focus variable active lenses, one or more data processing and storage device(s), an end-user enabled input device(s), and a display device.

Figure 2:
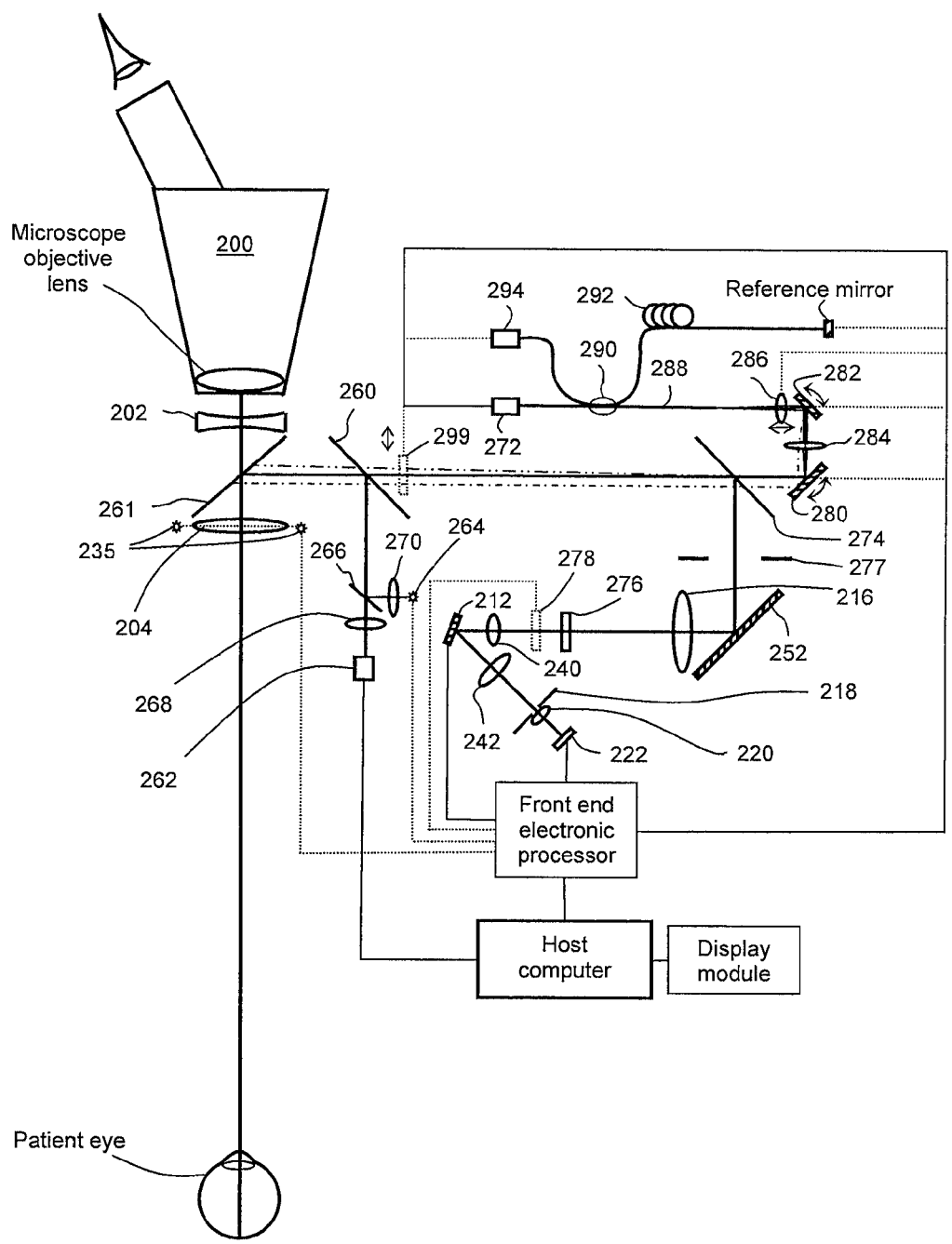
FIG. 2 shows one example embodiment of electronics interfacing with the optics of the wavefront sensor in FIG. 1 with those potentially active devices connected to the electronic control circuit.

FIG. 1 shows one example embodiment of the optical configuration of a large diopter range real time sequential wavefront sensor integrated with a surgical microscope and FIG. 2 shows the electronics connection version the wavefront sensor configuration of FIG. 1 with those potentially active devices connected to the electronics system.

In the embodiment of FIGS. 1 and 2, the first lens 104/204 of an 8-F wavefront relay is arranged at the very first optical input port of the wavefront sensor module. The first lens 104/204 is shared by the surgical microscope and the wavefront sensor module. The benefit of arranging this first lens 104/204 of the 8-F wavefront relay as close as possible to the patent eye is that the designed focal length of this first lens can be the shortest per the requirement of an 8-F wavefront relay and accordingly the overall optical path length of the wavefront sensor can be made the shortest. This combined with the folding of the wavefront relay beam path can make the wavefront sensor module compact. In addition, a larger diopter measurement range of the wavefront from the eye can be achieved when compared to a lens of the same diameter but arranged further downstream of the optical beam path. Furthermore, since there is always a need for the wavefront sensor to have an optical window at this location, the lens therefore can serve the dual purpose of both the window and the first lens for the wavefront relay system as well as for the microscope. However, it should be noted that the first lens 104/204 can also be arranged after the dichroic or short pass beam splitter 161/261.

The dichroic or short pass beam splitter 161/261 as shown in FIGS. 1 and 2 is used to reflect/deflect with high efficiency the near infrared wavefront relay beam (covering at least the optical spectral range of the superluminescent diode or SLD 172/272) to the rest of the wavefront sensor module while allowing most (for example ~85%) of the visible light to pass through. The dichroic or short pass beam splitter 161/261 can be designed to also allow a portion of the visible and/or near infrared light outside the SLD spectrum range to be reflected/deflected so that a clear live image of the anterior of the patient eye can be captured by an image sensor 162/262.

The compensating lens 102/202 above the dichroic or short pass beam splitter 161/261 is used to fulfill several functions. Firstly, to ensure that the surgical view to be formed and presented to the surgeon by the surgical microscope is not affected because of the use of the first lens 104/204 of the 8-F wavefront relay, this compensating lens 102/202 can be designed to compensate the effect of the first lens 104/204 to the microscopic view. Secondly, the compensating lens 102/202 can serve as the upper optical window which can be needed for sealing the wavefront sensor module. A third function of the compensating lens 102/202 is to direct the illumination beam from the surgical microscope away from the optical axis so that when the illumination beam hits the lens 104/204, specular reflections from the lens 104/204 are not directed back into the two stereoscopic viewing paths of the surgical microscope to interfere with the surgeon's viewing of the surgical scene. Finally, the compensating lens 102/202 can also be coated to allow only the visible spectrum of light to transmit through and to reflect and/or absorb the near infrared and ultraviolet spectrum of light. In this manner, the near infrared spectral portion of light that corresponds to the SLD spectrum from the microscope illumination source will not land on the patient eye to create any eye returned near infrared background light that can enter the wavefront sensor module to either saturate the position sensing device/detector or to create background noise. Meanwhile, the coating can also reject or absorb any ultraviolet light from the illumination source of the microscope. However, it should be noted that if the first lens is arranged after the dichroic or short pass beam splitter 161/261, there will then be no need for the compensation lens and a window with certain wavelength filtering function will be sufficient.

In FIGS. 1 and 2, the wavefront from the eye is relayed to a wavefront sampling image plane 8-F downstream at which a wavefront sampling aperture 118/218 is disposed. The wavefront relay is accomplished using two cascaded 4-F relay stages or an 8-F wavefront relay comprising, in addition to the first lens 104/204, a second lens 116/216, a third lens 140/240, and a fourth lens 142/242. The wavefront relay beam path is folded by a polarization beam splitter (PBS) 174/274, a mirror 152/252 and a MEMS beam scanning/shifting/deflecting mirror 112/212 to make the wavefront sensor module compact. Along the wavefront relay beam path, a band pass filter 176/276 can be arranged anywhere between the dichroic or short pass beam splitter 161/261 and the quadrant detector 122/222 to filter out any light outside the SLD spectrum to reduce background noise. In addition, an aperture 177/277 can be arranged at the first Fourier transform plane between the PBS 174/274 and the mirror 152/252 to serve the function of limiting the cone angle of the light rays from the eye and hence the diopter measurement range of the wavefront from the eye to a desired range as well as to prevent light from landing outside the mirror surface area of the MEMS scanner 112/212 that is disposed at the second Fourier transform plane.

The MEMS scan mirror 112/212 is disposed at the second Fourier transform plane of the 8-F wavefront relay to angularly scan the object beam so that the relayed wavefront at the final wavefront image plane can be transversely shifted relative to the wavefront sampling aperture 118/218. The wavefront sampling aperture 118/218 can be a fixed size or an active variable aperture. The sub-wavefront focusing lens 120/220 behind the aperture 118/218 focuses the sequentially sampled sub-wavefront onto a position sensing device/detector (PSD) 122/222 (such as a quadrant detector/sensor or a lateral effect position sensing detector). It should be noted that the electronics system can at least be connected to the SLD 172/272, the wavefront shifting MEMS scan mirror 112/212, and the PSD 122/222 to pulse the SLD, scan the MEMS mirror and collect the signal from the PSD in synchronization such that lock-in detection can be realized.

At this point, it should be noted that although in FIGS. 1 and 2, the first lens of the wavefront relay is arranged at the input port location of the wavefront sensor module or enclosure, this does not have to be the case. The first lens 104/204 can be arranged after the dichroic or short pass beam splitter 161/261 and a glass window can be arranged at the input port location. Accordingly, the rest of the wavefront relay can be redesigned and the optical function of the compensating lens or window 102/202 can be modified to ensure that good microscopic image is presented to the surgeon.

In addition to the folded wavefront relay beam path, three more optical beam paths are shown in FIGS. 1 and 2, one for imaging the eye, one for directing a fixation target to the eye, and one for launching a superluminescent diode (SLD) beam to the eye for the creation of the wavefront relay beam from the eye that carries the eye wavefront information.

An imaging beam splitter 160/260 directs at least some of the imaging light returned from the eye and reflected by the dichroic or short pass beam splitter 161/261 to an image sensor 162/262, such as a 2D pixel array CCD/CMOS sensor, via a lens or set of lenses 168/268. The image sensor 162/262 can be a black/white or color CMOS/CCD image sensor connected to the electronics system. The image sensor 162/262 provides a coplanar video or static image of a subject eye and can be focused to image either the anterior or the posterior of the eye. Further, a fixation/imaging beam splitter 166/266 directs the image of a fixation target 164/264, formed by a lens or set of lenses 170/270 together with the first lens 104/204, along a reverse path to the patient eye. The lens 168/268 in front of the image sensor 162/262 can be designed to work with the first lens 104/204 to provide a desired optical magnification for the live image of the anterior or posterior of the patient eye on a display (not shown in FIGS. 1 and 2) and be used to adjust focus either manually or automatically if needed to ensure that the image sensor plane is conjugate with, for example, the eye pupil plane so that a clear eye pupil image can be obtained. In the automatic focusing case, the lens 168/268 needs to be connected to the electronics system.

The lens 170/270 in front of the fixation target 164/264 can be designed to provide the patient eye with a comfortable fixation target of the right size and brightness. It can also be used to adjust focus to ensure that the fixation target is conjugate with the retina of the eye, or to fixate the eye at different distances, orientations, or even to fog the eye. In doing so, the lens 170/270 needs to be made active and be connected to the electronics system. The fixation light source 164/264 can be driven by the electronics system to flash or blink at a rate desired to differentiate it from, for example, the illumination light of a surgical microscope. The color of the fixation light source 164/264 can also change. The fixation target can be a micro-display with its displayed patterns or spot(s) variable to the desire of a surgeon/clinician. In addition, a micro-display based fixation target can also be used to guide the patient to gaze at different directions so that a 2D array of eye aberration map can be measured and generated, which can be used to assess the visual acuity of a patient's peripheral vision.

The fixation target 164/264 can be a red or green or yellow (or any color) light emitting diode (LED) with its output optical power dynamically controllable by the electronics system based on different background lighting conditions. For example, when a relatively strong illumination beam from a surgical microscope is turned on, the brightness of the fixation light source 164/264 can be increased to enable the patient to easily find the fixation target and fixate on it. A variable diaphragm or aperture (not shown in FIG. 1 or FIG. 2) can also be arranged in front of the lens 168/268 before the image sensor and connected to the electronics system to control the depth of field of the live image of the anterior or posterior of the eye. By dynamically changing the aperture size, the degree of blurriness of the eye image when the eye is axially moved away from the designed distance can be controlled, and the relationship between the blurriness of the eye image and the eye axial location as a function of the diaphragm or aperture size can be used as a signal to determine the axial distance of the eye. As an alternative, the eye distance can also be measured through well known means such as triangulation based on cornea scattered/reflected image spot locations of one or more near infrared illumination sources. Low coherence interferometry based eye distance measurement as will be disclosed below can also be employed.

A ring or multiple rings of LEDs (or arrays) (135/235) can be arranged encircling around the input port of the wavefront enclosure to serve multiple functions. One function is to simply provide flood illumination light within a wavelength spectral range so that eye returned light within this spectrum can reach the image sensor (162/262). In this way, if there is no illumination from the surgical microscope or if the illumination light from the surgical microscope has been filtered to only allow visible light to reach the eye, the contrast of the eye image as captured by the image sensor (162/262) can be kept to within a desired range. As one example, the image sensor is a monochrome UI-1542LE-M which is an extremely compact board-level camera having 1.3 Megapixel resolution (1280×1024 pixels). An NIR band pass filter can be disposed along the imaging path so that only the flood illumination light will reach the image sensor to maintain a relatively constant contrast of the live eye image.

A second function of the LEDs (135/235) is to create specular reflection image spots returned from the optical interfaces of the cornea and/or the eye lens (natural or artificial) so that Purkinje images of the LEDs (135/235) can be captured by the image sensor (162/262). Through image processing of these Purkinje images, the transverse position of the patient eye can be determined. In addition, the top and/or bottom surface profile or the topograph of the cornea and/or the eye lens (natural or artificial) can be figured out in the same way as a corneal topographer and/or a keratometer/keratoscope does. This information obtained can be used to determine change(s) in the cornea shape or even some other eye biometric/anatomic parameters. The measured change can then be used to set a targeted or expected refraction during or right after the refractive surgery so that when the incision or wound made in the cornea of the eye is completely healed, the final refraction of the eye will be as desired.

A third function of the LEDs (135/235) can be that some can be selectively turned on and projected onto the white of the eye to create light spots that can be captured by the image sensor (162/262) to realize eye distance measurement using the principle of optical triangulation. The change in the centroid position of the imaged light spots can be processed to figure out the eye distance.

In addition to providing a live eye pupil/iris or cornea image and to image the flood illumination effects, the image sensor signal can also be used for other purposes. For example, the live image can be used to detect the size, distance from the first lens (104/204), and transverse position of the eye pupil. When it is found that the size of the pupil is small, the wavefront sampling area can be correspondingly reduced. In other words, the pupil size information can be used in a closed loop manner for the automatic and/or dynamic adjustment and/or the scaling of wavefront sensing area per the pupil size.

One embodiment of this disclosure is the correction of wavefront measurement error as a result of eye position change within certain position range. The correction can be applied to both eye transverse position change as well as eye axial position change. In one embodiment, when it is found that the eye or pupil is not centered well enough, i.e. aligned well enough with respect to the optical axis of the wavefront sensor, the amount of transverse movement of the eye or the pupil relative to the wavefront sensor module is determined and used to either correct for the measured wavefront error that would be introduced by such an eye or pupil position transverse movement, or to adjust the drive signal of the wavefront sampling scanner so that the same area on the cornea is always sampled.

The transverse position of the eye or the pupil can be determined using the live eye image or other means. For example, the limbus can provide a reference to where eye is; the border between the pupil and the iris can also provide the reference to where the eye is. In addition, specularly reflected flood illumination light from the cornea anterior surface captured by the live eye camera as bright light spots or detected by additional position sensing detectors can also be used to provide the information on the transverse position of the eye. Furthermore, specularly reflected SLD light from the cornea anterior surface can also be captured by the live eye camera as bright light spots or detected by additional position sensing detectors to determine the transverse position of the eye. The SLD beam can also be scanned in two dimensions to search for the strongest cornea apex specular reflection and to determine the eye transverse position.

Figure 3:
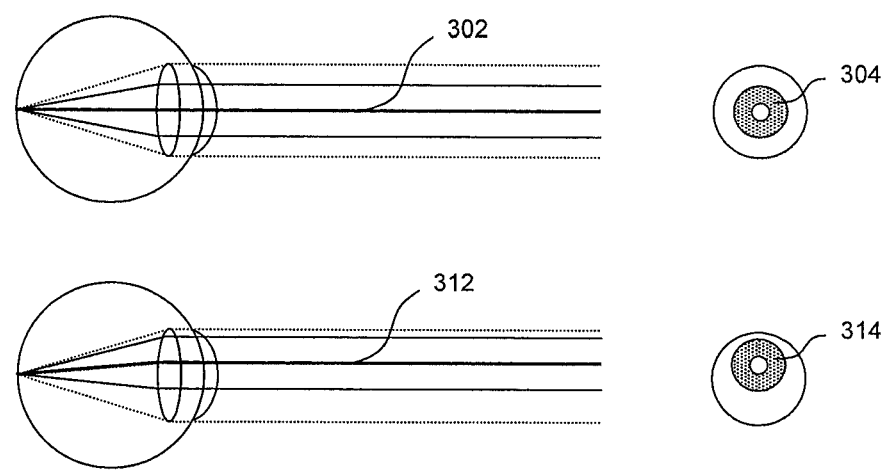
FIG. 3 shows what would happen to the wavefront sampling area on the cornea plane if the eye is transversely moved and there is no corresponding change made to the wavefront sampling scheme.

FIG. 3 shows what would happen to the wavefront sampling area on the cornea plane if the eye is transversely moved and there is no corresponding change made to the wavefront sampling scheme. Assume that the SLD beam is coaxial with and fixed in space relative to the wavefront sensor optical axis and the wavefront sensor is sampling around a radially or rotationally symmetric annular ring with respect to the optical axis of the wavefront sensor on the corneal plane. When the eye is well aligned, the SLD beam 302 would enter the eye through the apex of the cornea and the center of the pupil, land on the retina near the fovea. The returned wavefront would therefore be sampled within a radially or rotationally symmetric annular ring centered with respect to the apex of the cornea or the center of the eye pupil as shown by the annular ring 304 of the cross-sectional corneal plane view on the right. Now imagine if the eye is transversely moved downward with respect to the SLD beam and the wavefront sensor. The SLD beam 312 would now enter the eye off-centered, but still land on the retina near the fovea, although the exact location may be slightly different depending on the aberration of the eye. Since the wavefront sampling area is fixed relative to the SLD beam, on the corneal plane the sampled annular ring would, therefore, be shifted upward relative to the apex of the cornea or the center of the eye pupil as shown by the annular ring 314 of the cross-sectional corneal plane view on the right. This non-radially or non-rotationally symmetric wavefront sample would therefore cause wavefront measurement errors. In one embodiment of the present disclosure, with the information on the transverse position of the eye or the pupil, the wavefront measurement errors are corrected using software and data processing.

In one embodiment of the present disclosure, with the information on the transverse position of the eye or the pupil, the SLD beam can be scanned to follow or track the eye or the pupil so that the SLD beam will always enter the cornea from the same cornea location as designed (such as a position slightly off the apex of the cornea), to, for example, prevent specularly reflected SLD beam returned by the cornea from entering the wavefront sensor's PSD. The live eye image can also be used to determine the presence of the eye, and to turn on or off the SLD/wavefront detection system accordingly. To ensure that the SLD beam always enters the eye at a desired cornea location and is not blocked partially or fully by the iris as a result of eye transverse movement (within a certain eye movement range), a scan mirror 180/280 for scanning the SLD beam as shown in FIGS. 1 and 2 can be positioned at the back focal plane of the first wavefront relay lens 104/204. In this case, an angular scan of the scan mirror 180/280 will cause a transverse scan of the SLD beam with respect to the cornea plane. The image sensor captured live image of the eye or other eye transverse position detection means can be used to figure out the transverse position of the eye center and to provide a feedback signal to drive the scan mirror 180/280 to enable the SLD beam to follow the eye movement or track the eye.

In another embodiment of the present disclosure, the wavefront beam scanner 112/212 is driven with a proper DC offset to follow the eye transverse movement or to track the eye so that wavefront sampling is always done over the same area of the eye pupil. For example, the sampling can be done over an annular ring that is radially or rotationally symmetric with respect to the center of the eye pupil. In order to see how this is possible, let us recall that the wavefront beam scanner is located at the second Fourier transfer plane of the 8-F wavefront relay configuration. When the eye is transversely moved, at the 4-F wavefront image plane, the image of the wavefront will also be transversely moved with a proportional optical magnification or de-magnification depending on the focal length ratio of the first and second lenses. If the wavefront beam scanner does not do any scanning and there is no DC offset, when this transversely moved wavefront at the intermediate wavefront image plane is further relayed to the final wavefront sampling image plane, it will also be transversely displaced with respect to the sampling aperture. As a result, when the wavefront beam scanner does an angular rotational scan. The effective scanned annular ring area on the corneal plane will be de-centered as shown by the lower portion of FIG. 3.

Figure 4:
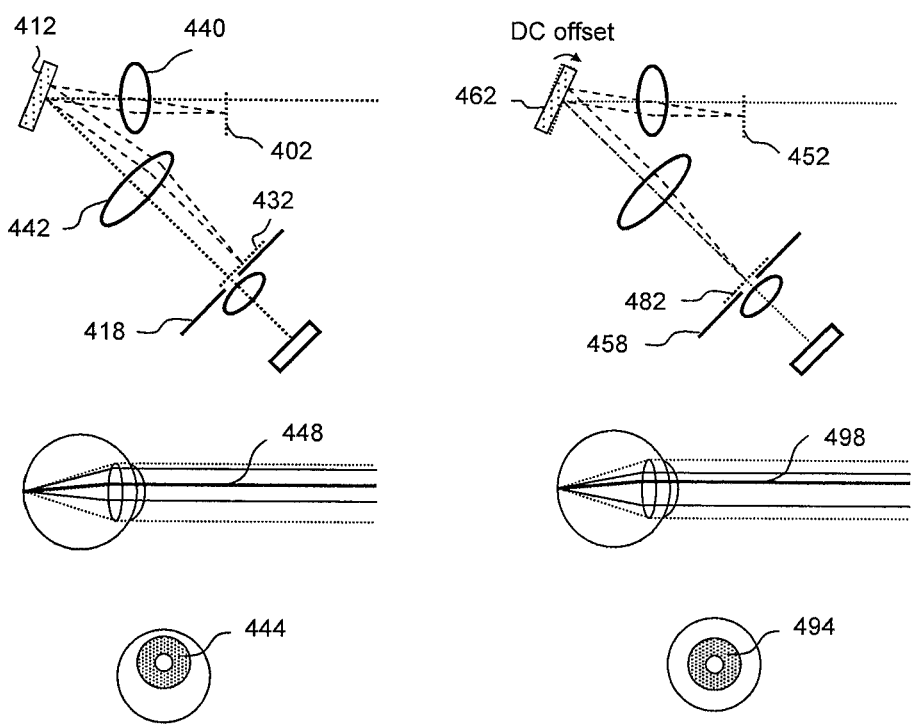
FIG. 4 shows how, by DC offsetting the wavefront beam scanner, one can compensate the transverse movement of the eye and hence continue to scan the same properly centered annular ring even though the eye is transversely moved.

FIG. 4 shows how, by DC offsetting the wavefront beam scanner, one can compensate the transverse movement of the eye and hence continue to scan the same properly centered annular ring even though the eye is transversely moved. As can be seen in FIG. 4, when there is a transverse movement of the eye, the SLD beam 448 would enter the eye off-centered and the wavefront at the cornea plane as an object to be relayed by the 8-F relay is also off-axis. The intermediate wavefront image 402 is therefore transversely displaced and if there is no DC offset of the wavefront beam scanner, without the scanning of the wavefront beam at the second Fourier transform image plane, the intermediate wavefront image would be relayed to the final wavefront sampling plane as a transversely displaced wavefront image 432 as well. In this case, if the wavefront beam scanner scans in the form of circular angular rotation relative to a zero DC offset angle, the sampled wavefront will then be a non-radially or non-rotationally symmetric annular ring with respect to the center of the eye as shown by the annular ring 444. However, if the wavefront beam scanner 462 as shown on the right side of FIG. 4 has a certain DC offset properly determined based on the transverse displacement of the eye, then the final wavefront image 482, when relayed to the final wavefront sampling image plane, can be transversely displaced to be re-centered with respect to the wavefront sampling aperture 458. In this case, the SLD beam 498 would still enter the eye off-centered, the wavefront at the cornea plane as an object to be relayed by the 8-F relay is off-axis when passing through the first, second and third lenses, but after the wavefront scanner, the relay is corrected by the wavefront scanner and is now on-axis. Accordingly, further angular rotational scanning of the wavefront beam scanner relative to this DC offset angle would result in the sampling of a radially or rotationally symmetric annular ring 494 with respect to the center of the eye.

One embodiment of the present disclosure is therefore to control the DC offset of the wavefront scanner in response to the transverse movement of the eye that can be determined by the live eye camera or other means. Owing to the fact that along the wavefront relay path, the wavefront imaging is done not on-axis but off-axis along some of the imaging path, there can therefore be other optical aberrations introduced, including, for example, coma and prismatic tilt. These additional aberrations introduced as a result of off-axis wavefront relaying can be taken care of through calibration and be treated as if there is inherent aberration of an optical imaging or relay system and hence can be subtracted using calibration and data processing.

Figure 5:
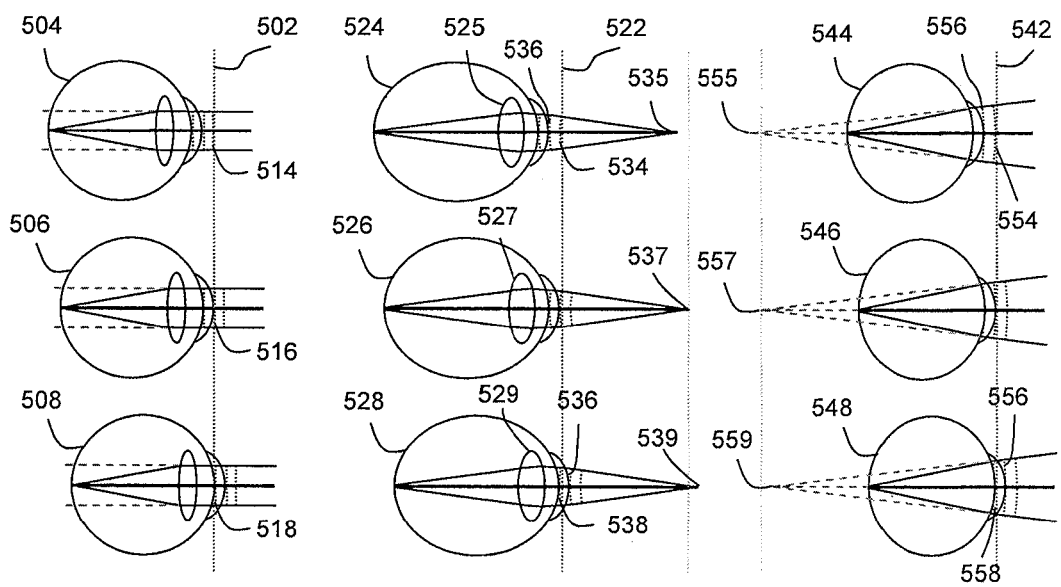
FIG. 5 illustrates what happens to the wavefront or refractive error being measured if the eye is axially moved from the designed position.

In another embodiment of the present disclosure, when it is found that the eye is not axially positioned at the designed distance from the object plane of the wavefront sensor, the amount of axial displacement of the eye relative to the designed axial position is determined and the information is used to correct for the measured wavefront error that would be introduced by such an eye axial movement. FIG. 5 illustrates what happens to the wavefront or refractive error being measured if the eye is axially moved from the designed position.

On the left column of FIG. 5, three emmetropic eyes are shown with the top one 504 moved further away from the wavefront sensor, with the middle one 506 at the designed axial location of the wavefront sensor and the bottom one 508 moved towards the wavefront sensor. As can be seen, since the wavefront emerging from this emmetropic eye is planar, at the designed object plane 502 from which the wavefront will be relayed to the final wavefront sampling plane, the wavefronts 514, 516 and 518 are all planar for the three cases. Therefore, when the eye is emmetropic, if the eye is slightly displaced axially from the designed position, the wavefront measurement result will not be affected.

However, if the eye is myopic as shown by the middle column of FIG. 5 where the crystalline lens (525, 527, 529) of the eye is shown as thicker and the eye (524, 526, 528) is also drawn as longer, the wavefront emerging from the eye will converge to a point (535, 537, 539) and the dioptric value of the wavefront at the corneal plane is determined by the distance from the corneal plane of the eye to the convergent point. In this case, if the eye is moved slightly further away from the wavefront sensor, as shown by the top example of the middle column, the wavefront at the object plane 522 of the wavefront sensor is not the same as the wavefront at the corneal plane of the eye. In fact, the convergent radius of curvature of the wavefront at the object plane of the wavefront sensor is smaller than that at the corneal plane. Therefore, when this wavefront 534 at the object plane of the wavefront sensor is measured by the wavefront sensor, the measured result will be different from the wavefront 536 at the corneal plane as the radius of curvature of the wavefront 534 is smaller than the radius of curvature of the wavefront 536. If, on the other hand, the eye is moved closer towards the wavefront sensor as shown by the bottom example of the middle column, the wavefront 538 at the object plane 522 of the wavefront sensor is again not the same as the wavefront 536 at the corneal plane of the eye. In fact the radius of curvature of the wavefront 538 at the object plane of the wavefront sensor is now larger than the wavefront 536 at the corneal plane. As a result, the measured wavefront result at the wavefront object plane will again be different from that at the corneal plane of the eye.

When the eye is hyperopic as shown by the right column of FIG. 5 where the crystalline lens of the eye is removed and the eye (544, 546, 548) is also drawn as shorter than normal to simulate a short aphakic eye, the wavefront emerging from the eye will be divergent and by extending the divergent light rays backward, one can find a virtual focus point (555, 557, 559) from which the light rays originate. The hyperopic dioptric value of the wavefront at the corneal plane is determined by the distance from the corneal plane of the eye to the virtual focus point. In this case, if the eye is moved further away from the wavefront sensor, as shown by the top example of the right column, the wavefront 554 at the object plane 542 of the wavefront sensor is again not the same as the wavefront 556 at the corneal plane of the eye. In fact, the divergent radius of curvature of the wavefront 554 at the object plane of the wavefront sensor is now larger than the divergent radius of curvature of the wavefront 556 at the corneal plane. Therefore, when this wavefront 554 at the object plane of the wavefront sensor is measured by the wavefront sensor, the measured result will again be different from the wavefront 556 at the corneal plane. If, on the other hand, the eye is moved closer towards the wavefront sensor as shown by the bottom example of the right column, the wavefront 558 at the object plane 542 of the wavefront sensor will still be different from the wavefront 556 at the corneal plane of the eye. In fact, the radius of curvature of the divergent wavefront 558 at the object plane of the wavefront sensor will now be smaller than the wavefront 556 at the corneal plane. As a result, the measured wavefront result at the wavefront object plane will again be different from that at the corneal plane of the eye.

In one embodiment of the present disclosure a real time means to detect the axial position of the eye under test is incorporated and in real time the information on the amount of axial movement of the eye relative to the wavefront sensor module's object plane is used to correct for the measured wavefront error that would be introduced by such an eye axial movement. As will be discussed later, the eye axial position measurement means include optical triangulation and optical low coherence interferometry as is well known to those skilled in the art. A calibration can be done to determine the relationship between the axial position of the eye, and the true wavefront aberration of the eye versus the wavefront aberration at the object plane of the wavefront sensor as measured by the wavefront sensor. A look up table can then be established and used in real time to correct for the wavefront measurement errors. In the case of a cataract surgery, the surgical microscope, when fully zoomed-out, can generally present to a surgeon a relatively sharp-focused view of the patient eye within an axial range of the order of about ±2.5 mm. So when the surgeon focuses a patient eye under a surgical microscope, the variation in the patient eye's axial position should be within a range of about ±2.5 mm. Therefore, the calibration can be done over such a range and the look-up table can be established also over such a range.

In one example embodiment of the present disclosure, when it is found that the eye is being irrigated with water/solution, or there are optical bubbles, or the eye lid is in the optical path, or facial skin, or a surgeon's hand, or a surgical tool or instrument, is in the image sensor's view field and is blocking the wavefront relay beam path partially or fully, the wavefront data can be abandoned/filtered to exclude the "dark" or "bright" data and at the same time, the SLD 172/272 can be turned off. In another example embodiment of the present disclosure, the wavefront sensor is used to figure out if the eye is dry and a reminder in the form of video or audio signal can be sent to the surgeon or clinician to remind him/her when to irrigate the eye. Moreover, the signal from the image sensor 162/262 can also be used to identify if the patient eye is in a phakic, or aphakic or pseudo-phakic state and accordingly, the SLD pulses can be turned on during only the needed period. These approaches can reduce the patient's overall exposure time to the SLD beam and thus possibly allow higher peak power or longer on-duration SLD pulses to be used to increase the wavefront measurement signal to noise ratio. Additionally, an algorithm can be applied to the resultant eye image to determine optimal distance to the eye through the effective blurriness of the resultant image, and/or in tandem with triangulation fiducials.

In FIGS. 1 and 2, a large size polarization beam splitter (PBS) 174/274 is used for launching the SLD beam to the patient eye. The reason for using a large window size is to ensure that the wavefront relay beam from an eye over a desired large diopter measurement range is not partially, but fully, intercepted by the PBS 174/274. In the example embodiment, the beam from the SLD 172/272 is preferably p-polarized so that the beam substantially transmits through the PBS 174/274 and is launched to the eye for creating the eye wavefront. The SLD beam can be pre-shaped or manipulated so that when the beam enters the eye at the cornea plane, it can be either collimated or focused or partially defocused (either divergently or convergently) at the cornea plane. When the SLD beam lands on the retina as either a relatively small light spot or a somewhat extended light spot, it will be scattered over a relatively large angular range, and the returned beam thus generated will have both the original polarization and an orthogonal polarization. As is well known to those skilled in the art, for ophthalmic wavefront sensor applications, only the orthogonal polarization component of the wavefront relay beam is used for eye wavefront measurement. This is because in the original polarization direction, there exist relatively strongly reflected SLD light waves from the cornea and the eye's lens which can introduce errors to the wavefront measurement. So another function of the large PBS 174/274 is to only allow the orthogonally polarized wavefront relay beam to be reflected by the PBS 174/274 and to direct the returned light waves polarized in the original direction to be transmitted through the PBS 174/274 and absorbed or used for other purpose such as to monitor if there is specular reflection of the SLD beam by the cornea or eye lens back into the wavefront sensor module.

In FIGS. 1 and 2, a band pass filter 176/276 is arranged in the wavefront relay beam path to reject any visible light and/or ambient background light, and to only allow the desired relatively narrow spectrum of the wavefront relay beam light that the SLD generates to enter the rest of the wavefront sensor module.

In addition to the fact that the SLD beam can be scanned to follow eye transverse movement, the SLD beam can also be scanned to land over a small scanned area on the retina with the control from the electronics system which includes the front end electronic processor and the host computer. In one example embodiment, to ensure that the SLD beam always enters the eye at a desired cornea location and is not blocked partially or fully by the iris as a result of eye movement (within a certain eye movement range), a scan mirror 180/280 for scanning the SLD beam as shown in FIGS. 1 and 2 can be positioned at the back focal plane of the first wavefront relay lens 104/204. In this case, an angular scan of the scan mirror 180/280 will cause a transverse scan of the SLD beam with respect to the cornea plane but still allow the SLD beam to land on the same retina location if the eye is emmetropic. The image sensor captured live image of the eye pupil can be used to figure out the transverse position of the eye pupil center and to provide a feedback signal to drive the scan mirror 180/280 and to enable the SLD beam to follow the eye movement or track the eye.

In one example embodiment, to enable the SLD beam to land and also scan around a small area on the retina, another scan mirror 182/282 as shown in FIGS. 1 and 2 can be positioned conjugate to the cornea plane at the back focal plane of a SLD beam shape manipulation lens 184/284. Another lens 186/286 can be used to focus or collimate or shape the SLD beam from the output port of, for example, a single mode optical fiber (such as a polarization maintaining (PM) single mode fiber) 188/288, onto the scan mirror 182/282. The scanning of the SLD beam over a small area on the retina can provide several benefits; one is to reduce speckle effects resulting from having the SLD beam always landing on the same retina spot area, especially if the spot size is very small; another benefit is to divert the optical energy over a slightly larger retinal area so that a higher peak power or longer on-duration pulsed SLD beam can be launched to the eye to increase the signal to noise ratio for optical wavefront measurement; and still another benefit is to enable the wavefront measurement to be averaged over a slightly larger retinal area so that wavefront measurement errors resulting from retinal topographical non-uniformity can be averaged out or detected and/or quantified. As an alternative, by controlling the focusing and de-focusing of the SLD beam using the lens 186/286 (or 184/284), the SLD beam spot size on the retina can also be controlled to achieve similar goals.

It should be noted that the scanning of the SLD beam relative to the cornea and the retina can be performed independently, simultaneously, and also synchronized. In other words, the two SLD beam scanners 180/280 and 182/282 can be activated independently of each other but at the same time. In addition, it should be noted that a laser beam as an eye surgery light beam (not shown In FIGS. 1 and 2) can be combined with the SLD beam and delivered to the eye through the same optical fiber or through another free space light beam combiner to be delivered to the same scanner(s) for the SLD beam or other scanners so that the eye surgery laser beam can be scanned for performing refractive surgery of the eye such as limbal relaxing incision (LRI), or other corneal sculpting. The SLD and the eye surgery laser can have different wavelengths and be combined using optical fiber based wavelength division multiplexing couplers or free space dichroic beam combiners.

An internal calibration target 199/299 can be moved into the wavefront relay beam path when a calibration/verification is to be made. The SLD beam can be directed to be coaxial with the wavefront relay optical beam path axis when the internal calibration target is moved in place. The calibration target can be made from a material that will scatter light in a way similar to an eye retina with maybe some desired attenuation so that a reference wavefront can be generated and measured by the sequential wavefront sensor for calibration/verification purpose. The generated reference wavefront can be either a nearly planer wavefront or a typical aphakic wavefront, or a divergent or convergent wavefront of any other degree of divergence/convergence.

Although for eye wavefront measurement, only the beam returned from the retina with an orthogonal polarization is used, this does not mean that those returned light waves from the cornea, the eye's lens, and the retina with the original polarization are useless. On the contrary, these returned light waves with the original polarization can provide very useful information. FIG. 1 and 2 show that the eye returned light waves with the original polarization can be used for the measurement of eye distance from the wavefront sensor module, the location of the eye's lens (either natural or implanted) in the eye (i.e. effective lens position), the anterior chamber depth, the eye length and other eye anterior and/or posterior biometric or anatomic parameters. In FIGS. 1 and 2, the returned light waves that pass through the PBS 174/274 is collected with a low coherence fiber optic interferometer as is typically employed for optical low coherence interferometry (OLCI) or optical coherence tomography (OCT) measurements. The SLD output fiber 188/288 can be single mode (SM) (and polarization maintaining (PM) if desired) and can be connected to a normal single mode (SM) fiber (or a polarization maintaining (PM) single mode optical fiber) coupler so that one portion of the SLD light is sent to the wavefront sensor and another portion of the SLD light is sent to a reference arm 192/292. The optical path length of the reference arm can be roughly matched to that corresponding to optical path length of the light waves returned from the eye.

The light wave returned from different parts of the eye can be made to recombine with the reference light wave returned through the reference fiber arm 192/292 at the fiber coupler 190/290 to result in optical low coherence interference. This interference signal can be detected by the detector 194/294 as shown in FIGS. 1 and 2. Note that although in FIGS. 1 and 2, the same fiber coupler 190/290 is used for both splitting and recombining the light waves in a Michelson type of optical interferometer configuration, other well known fiber optic interferometer configurations can all be used as well, one example is a Mach-Zehnder type configuration using two fiber couplers with a fiber circulator in the sample arm to efficiently direct the sample arm returned light wave to the recombining fiber coupler.

Various OLCI/OCT configurations and detection schemes, including spectral domain, swept source, time domain, and balanced detection, can be employed. In order to keep the wavefront sensor module (to be attached, for example, to a surgical microscope or a slit lamp bio-microscope) compact, the detection module 194/294, the reference arm 192/292 (including the reference mirror plus the fiber loop), and even the SLD 172/272 and the fiber coupler 190/290, can be located outside the wavefront sensor enclosure. The reason for doing this is that the detection module 194/294 and/or the reference arm 192/292 and/or the SLD source 172/272 can be bulky depending on the scheme being used for the OLCI/OCT operation. The electronics for operating the OLCI/OCT sub-assembly can be located either inside the wavefront sensor enclosure or outside the wavefront sensor enclosure. For example, when a balanced detection scheme is employed as discussed in U.S. Pat. No. 7,815,310, a fiber optic circulator (not shown) may need to be incorporated in the SLD fiber arm. When time domain detection is employed, the reference arm 192/292 may need to include an optical path length scanner or a rapid scanning optical delay line (not shown), which needs to be controlled by the electronics. When spectral domain detection scheme is employed, the detection module may need to include an optical spectrometer and a line scan camera (not shown), which needs to be controlled by the electronics. When swept source detection scheme is employed, the light source may need to include a wavelength scanner (not shown), which needs to be controlled by the electronics.

In one example embodiment, in order to ensure that a relatively strong OLCI/OCT signal can be collected, the scan mirror(s) 180/280 (and/or 182/282) can be controlled by the electronics system to specifically let relatively strong specular reflections from, for example, the cornea, the eye's lens (natural or artificial) and the retina, to return to the optic fiber interferometer so that axial distance of the optical interfaces of these eye components with respect to the wavefront sensor module or relative to each other can be measured. This operation can be sequentially separated from the eye wavefront measurement as in the latter case, specular reflection should perhaps be avoided. Alternatively, two different wavelength bands can be used and spectral separation can be employed. On the other hand, the OLCI/OCT signal strength can be used as an indication on whether specular reflection is being collected by the wavefront sensor module and if yes, the wavefront sensor data can be abandoned.

In another example embodiment, the SLD beam can be scanned across the anterior segment of the eye or across a certain volume of the retina and biometric or anatomic structure measurement of the various parts of the eye can be made. One particularly useful measurement is the cornea surface and thickness profile.

In one example embodiment, the beam scanner 112/212 used for shifting/scanning the wavefront and those (180/280, 182/282) used for scanning the SLD beam can also have a dynamic DC offset to bring additional benefits to the present disclosure. For example, the scanner 112/212 used for shifting and/or scanning the wavefront can be utilized to provide compensation to potential misalignment of the optical elements as a result of environmental changes such as temperature to ensure that wavefront sampling is still rotationally symmetric with respect to the center of the eye pupil. Meanwhile, the reference point on the position sensing device/detector (PSD) can also be adjusted if needed per the compensated image spot locations through a calibration. If there is any angular DC offset of the sampled image spots relative to the PSD reference point, this can be taken care of through calibration and data processing. We mentioned that the scanner 180/280 used for scanning the SLD beam can be employed to follow eye transverse movement within a certain range through a feedback signal from the image sensor 162/262. With the eye moved relative to the wavefront sensor module, even though the SLD beam can be made to enter the eye through the same cornea location at the same angle as it would when the eye is centered well relative to the wavefront sensor module, the returned wavefront beam from the eye will be transversely displaced relative to the optical axis of the wavefront sensor module. As a result, the relayed wavefront at the wavefront sampling image plane will also be transversely displaced. In this case, the DC offset of the scanner 112/212 used for shifting the wavefront can be employed to compensate for this displacement and still make the scanned wavefront beam rotationally symmetric with respect to the wavefront sampling aperture 118/218. In this case, there can be coma or prismatic tilt or other additional aberration introduced, these can be taken care of through calibration and data processing. In doing so, any wavefront measurement error induced by the change in the eye position/location can be compensated or corrected.

With the combination of information provided by the image sensor, the wavefront sensor, the specular reflection detector and/or the low coherence interferometer, it is possible to combine some or all the information to realize an auto selection of the correct calibration curve and/or the correct data processing algorithm. Meanwhile, a data integrity indicator, or a confidence indicator, or a cataract opacity degree indicator, or an indicator for the presence of optical bubbles can be shown to the surgeon or clinician through audio or video or other means, or connected to other instruments in providing feedback. The combined information can also be used for intraocular pressure (IOP) detection, measurement and/or calibration. For example, a patient heart beat generated or an external acoustic wave generated intraocular pressure change in the anterior chamber of the eye can be detected by the wavefront sensor and/or the low coherence interferometer in synchronization with an oximeter that monitors the patient heart beat signal. A pressure gauge equipped syringe can be used to inject viscoelastic gel into the eye to inflate the eye and also measure the intraocular pressure. The combined information can also be used to detect and/or confirm the centering and/or tilt of an implanted intraocular lens (IOL) such as a multi-focal intraocular lens. The combined information can also be used for the detection of the eye status, including phakia, aphakia and pseudophakia. The wavefront sensor signal can be combined with the OLCI/OCT signal to measure and indicate the degree of optical scattering and/or opacity of the eye lens or the optical media of the ocular system.

The wavefront sensor signal can also be combined with the OLCI/OCT signal to measure tear film distribution over the cornea of the patient eye.

One requirement for real time ophthalmic wavefront sensor is a large diopter measurement dynamic range that can be encountered during a cataract surgery, such as when the natural eye lens is removed and the eye is aphakic. Although the optical wavefront relay configuration has been designed to cover a large diopter measurement dynamic range, the sequential nature has eliminated the cross talk issue, and the lock-in detection technique can filtered out DC and low frequency 1/f noises, the dynamic range can still be limited by the position sensing device/detector (PSD). In one embodiment, the optics is optimally designed so that over the desired the diopter coverage range, the image/light spot size on the PSD is always within a certain range such that its centroid can be sensed by the PSD. In another embodiment, a dynamic wavefront/defocus offsetting device 178/278 as shown in FIGS. 1 and 2 is disposed at the intermediate wavefront image plane, i.e. the 4-F plane which is conjugate to both the cornea plane and the wavefront sampling plane. The dynamic wavefront/defocus offsetting device 178/278 can be a drop-in lens, a focus variable lens, a liquid crystal based transmissive wavefront manipulator, or a deformable mirror based wavefront manipulator. In the case that the PSD becomes the limiting factor for measuring a large diopter value (positive or negative), the electronics system can activate the wavefront/defocus offsetting device 178/278 to offset or partially/fully compensate some or all of the wavefront aberrations. For example, in the aphakic state, the wavefront from the patient's eye is relatively divergent, a positive lens can be dropped into the wavefront relay beam path at the 4-F wavefront image plane to offset the spherical defocus component of the wavefront and therefore to bring the image/light spot landing on the PSD to within the range such that the PSD can sense/measure the centroid of sequentially sampled sub-wavefronts.

In other cases like high myopia, high hyperopia, relatively large astigmatism or spherical aberrations, the wavefront/defocus offsetting device 178/278 can be scanned and deliberate offsetting can be applied to one or more particular aberration component(s) in a dynamic manner. In this way, some lower order aberrations can be offset and information on other particular higher order wavefront aberrations can be highlighted to reveal those clinically important feature(s) of the remaining wavefront aberrations that need to be further corrected. In doing so, the vision correction practitioner or surgeon can fine tune the vision correction procedure and minimize the remaining wavefront aberration(s) in real time.

Figure 6:
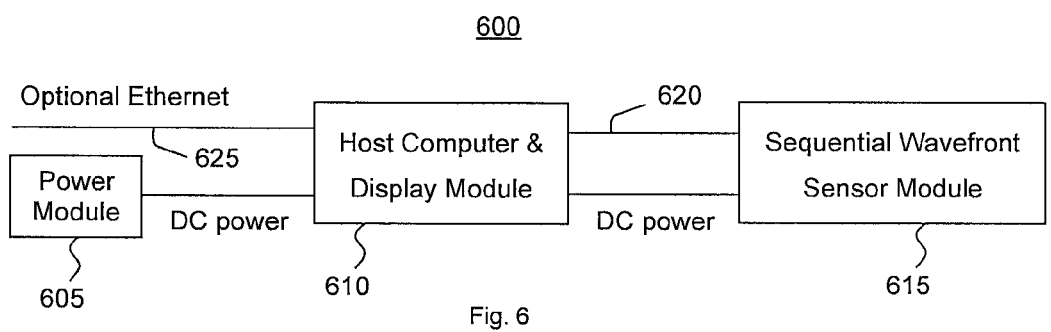
FIG. 6 shows an overall block diagram of one example embodiment of an electronics system that controls and drives the sequential wavefront sensor and the associated devices shown in FIGS. 1 and 2.

FIG. 6 shows an overall block diagram of one example embodiment of the electronics system 600 that controls and drives the sequential wavefront sensor and other associated active devices as shown in FIGS. 1 and 2. In this embodiment, a power module 605 converts AC power to DC power for the entire electronics system 600. The wavefront data and the images/movies of the eye can be captured and/or recorded in synchronization in a stream manner. The host computer & display module 610 provides back-end processing that includes synchronizing a live eye image with the wavefront measurement result, and a visible display to the user with the wavefront information overlaid on or displayed side-by-side with the live image of the patient eye. The host computer & display module 610 can also convert the wavefront data into computer graphics which are synchronized and blended with the digital images/movies of the eye to form a composite movie and display the composite movie on the display that is synchronized to real-time activity performed during a vision correction procedure.

The host computer & display module 610 also provides power and communicates with the sequential wavefront sensor module 615 through serial or parallel data link(s) 620. The optics as shown in FIGS. 1 and 2 reside together with some front-end electronics in the sequential wavefront sensor module 615. In one embodiment of the present disclosure, the host computer & display module 610 and sequential wavefront sensor module 615 communicate through a USB connection 620. However any convenient serial, parallel, or wireless data communication protocol will work. The host computer & display module 610 can also include an optional connection 625 such as Ethernet to allow downloading of wavefront, video, and other data processed or raw onto an external network (not shown in FIG. 6) for other purposes such as later data analysis or playback.

It should be noted that the display should not be limited to a single display shown as combined with the host computer. The display can be a built-in heads up display, a semi-transparent micro display in the ocular path of a surgical microscope, a back-projection display that can project information to overlay on the live microscopic view as seen by a surgeon/clinician, or a number of monitors mutually linked among one another. In addition to overlaying the wavefront measurement data onto the image of the patient eye, the wavefront measurement result (as well as the other measurement results such as those from the image sensor and the low coherence interferometer) can also be displayed adjacently on different display windows of the same screen or separately on different displays/monitors.

Compared with prior art wavefront sensor electronics systems, the present electronics system is different in that the host computer & display module 610 is configured to provide back-end processing that includes synchronizing a live eye image with the sequential wavefront measurement data and at the same time, displays the synchronized information by overlaying the wavefront information on the live eye image or displaying the wavefront information side-by-side next to the live eye image. In addition, the front-end electronics (as will be discussed shortly) inside the sequential wavefront sensor module 615 operates the sequential real time ophthalmic wavefront sensor in lock-in mode, and is configured to send the front-end processed wavefront data to be synchronized with the live eye image data to the host computer and display module 610.

Figure 7:
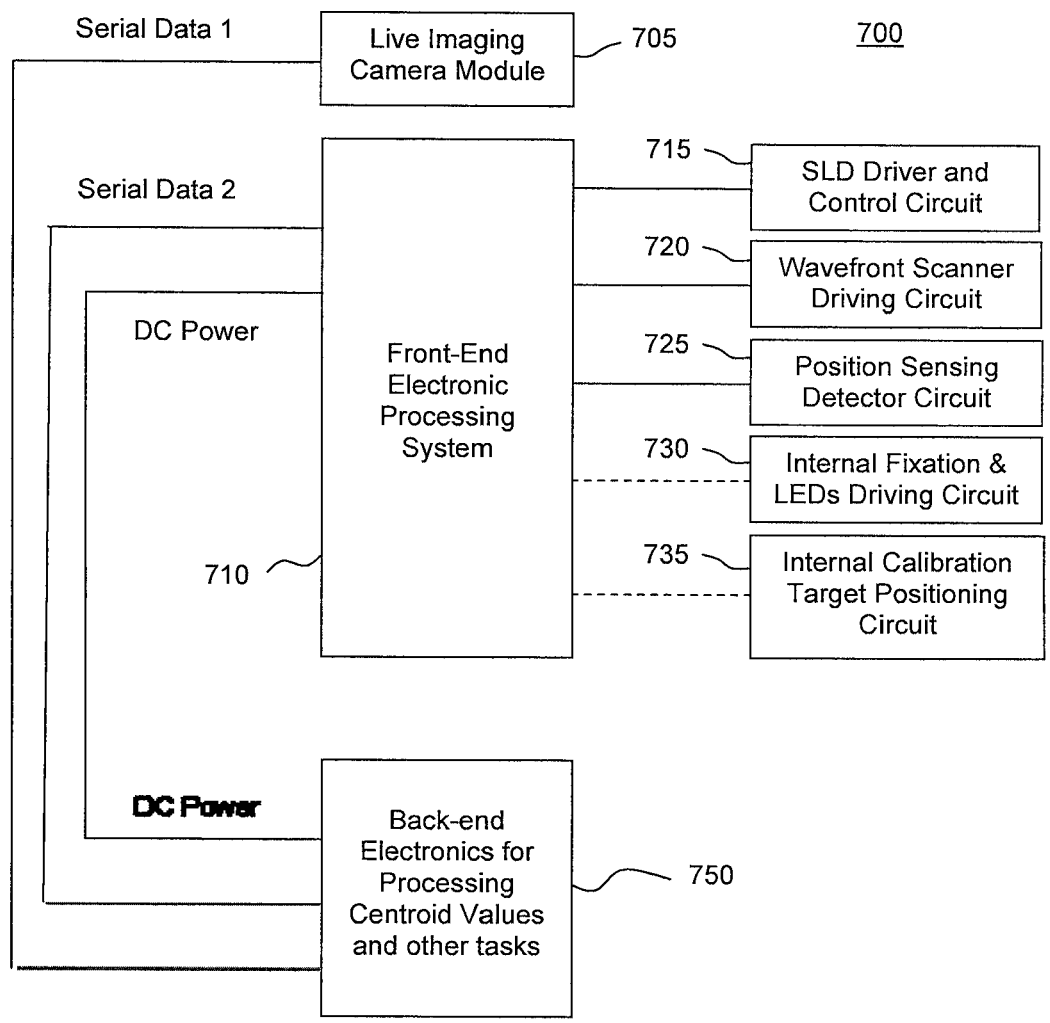
FIG. 7 shows a block diagram of one example embodiment of the front-end electronic processing system and the live imaging camera that resides within the sequential wavefront sensor module and the back-end electronic processing system that resides in the host computer and display module shown in FIG. 6.

FIG. 7 shows a block diagram of one example embodiment of the front-end electronic processing system 700 that resides within the wavefront sensor module 615 shown in FIG. 6. In this embodiment, a live imaging camera module 705 (such as a CCD or CMOS image sensor/camera) provides a live image of the patient eye, the data of which is sent to the host computer and display module 610 as shown in FIG. 6 so that the wavefront data can be overlaid on the live image of the patient's eye. A front-end processing system 710 is electronically coupled to the SLD drive and control circuit 715 (which, in addition to pulsing the SLD, may also perform SLD beam focusing and SLD beam steering as has been discussed before with regard to FIGS. 1 and 2), to the wavefront scanner driving circuit 720, and to the position sensing detector circuit 725. Compared to prior art wavefront sensor electronics systems, the presently disclosed front-end electronic processing system has a number of features that when combined in one way or another make it different and also advantageous for real time ophthalmic wavefront measurement and display, especially during eye refractive cataract surgery. The light source used for creating the wavefront from the eye is operated in pulse and/or burst mode. The pulse repetition rate or frequency is higher (typically in or above the kHz range) than the typical frame rate of a standard two dimensional CCD/CMOS image sensor (which is typically about 25 to 30 Hz (generally referred to as frames per second)). Furthermore, the position sensing detector is two dimensional with high enough temporal frequency response so that it can be operated in lock-in detection mode in synchronization with the pulsed light source at a frequency above the 1/f noise frequency range. The front-end processing system 710 is at least electronically coupled to the SLD drive and control circuit 715, the wavefront scanner driving circuit 720, and the position sensing detector circuit 725. The front-end electronics is configured to phase-lock the operation of the light source, the wavefront scanner, and the position sensing detector.

In addition, the front-end processing system 710 can also be electronically coupled to an internal fixation and LEDs driving circuit 730, and an internal calibration target positioning circuit 735. In addition to driving the internal fixation as discussed before with reference to FIGS. 1 and 2, the LEDs driving circuit 730 can include multiple LED drivers and be used to drive other LEDs, including indicator LEDs, flood illumination LEDs for the eye live imaging camera, as well as LEDs for triangulation based eye distance ranging. The internal calibration target positioning circuit 735 can be used to activate the generation of a reference wavefront to be measured by the sequential wavefront sensor for calibration/verification purpose.

The front-end and back-end electronic processing systems include one or more digital processors and non-transitory computer readable memory for storing executable program code and data. The various control and driving circuits 715-735 may be implemented as hard-wired circuitry, digital processing systems or combinations thereof as is know in the art.

Figure 8:
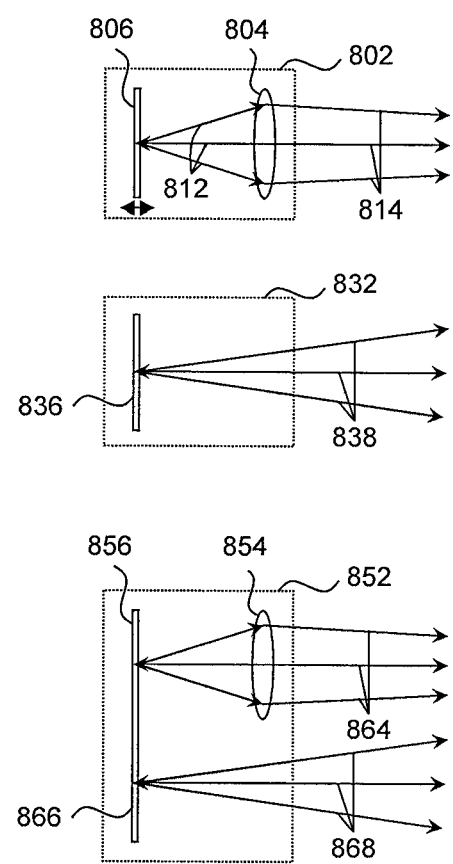
FIG. 8 shows an example internal calibration target that can be moved into the wavefront relay beam path to create one or more reference wavefront(s) for internal calibration and/or verification.

FIG. 8 shows an example internal calibration and/or verification target 802/832/852 that can be moved into the wavefront relay beam path to create one or more reference wavefront(s) for internal calibration and/or verification. In one embodiment, the internal calibration and/or verification target comprises a lens (such as an aspheric lens) 804 and a diffusely reflective or scattering material such as a piece of spectralon 806. The spectralon 806 can be positioned a short distance in front of or beyond the back focal plane of the aspheric lens 804. The aspheric lens 804 can be anti-reflection coated to substantially reduce any specular reflection from the lens itself.

When the internal calibration and/or verification target 802 is moved into the wavefront relay beam path, it would be stopped by, for example, a magnetic stopper (not shown), such that the aspheric lens 804 is centered and coaxial with the wavefront relay optical axis. The SLD beam would then be intercepted by the aspheric lens with minimum specular reflection and the SLD beam would be focused, at least to some extent, by the aspheric lens to land on the spectralon 806 as a light spot. Since the spectralon is designed to be highly diffusely reflective and/or scattering, the returned light from the spectralon will be in the form of a divergent cone 812 and after travelling backward through the aspheric lens, it will become a slightly divergent or convergent beam of light 814.

The position of the internal calibration target as shown in the FIGS. 1 and 2 is somewhere between the first lens 104/204 and the polarization beam splitter 174/274, therefore a somewhat slightly divergent or convergent beam there propagating backward would be equivalent to a beam coming from a point source in front of or behind the object plane of the first lens 104/204. In other words, the internal calibration and/or verification target created reference wavefront is equivalent to a convergent or divergent wavefront coming from an eye under test.

In one embodiment, the actual axial position of the spectralon relative to the aspheric lens can be designed such that the reference wavefront can be made to resemble that from an aphakic eye. In another embodiment, the actual axial position of the spectralon can be designed such that the reference wavefront thus created can be made to resemble that from an emmetropic or a myopic eye.

It should be noted that although we used an aspheric lens here, a spherical lens and any other type of lens, including cylindrical plus spherical lens or even a tilted spherical lens can be used to create a reference wavefront with certain intended wavefront aberrations for calibration and/or verification. In one embodiment, the position of the spectralon relative to the aspheric lens can also be continuously varied so that the internally created wavefront can have continuously variable diopter values to enable a complete calibration of the wavefront sensor over the designed diopter measurement range.

In another embodiment, the internal calibration target can simply be a bare piece of spectralon 836. In this case, the requirement on the stop position of the piece of spectralon 836 can be lessened as any part of a flat spectralon surface, when moved into the wavefront relay beam path, can intercept the SLD beam to generate substantially the same reference wavefront assuming that the topographic property of the spectralon surface is substantially the same. In this case, the emitted beam from the bare piece of spectralon will be a divergent beam 838.

In still another embodiment, the internal calibration and/or verification target comprises both a bare piece of spectralon 866 and also a structure with an aspheric lens 854 and a piece of spectralon 856, where the spectralon (866 and 856) can be a single piece. The mechanism to move the internal calibration and/or verification target 852 into the wavefront relay beam path can have two stops, an intermediate stop that does not need to be very repeatable and a final magnetic stopping position that is high repeatable. The intermediate stopping position can be used to enable the bare piece of spectralon to intercept the SLD beam and the highly repeatable stopping position can be used to position the aspheric lens plus spectralon structure so that the aspheric lens is centered well and coaxial with the wavefront relay beam optical axis. In this way, one can obtain two reference wavefronts (864 and 868) and hence use the internal calibration target to check if the system transfer function behaves as designed or if there is any need to compensate for any misalignment of the wavefront relay optical system.

Due to the difference in the amount of light returned from a real eye versus that returned from a piece of spectralon, an optical attenuation means, such as a neutral density filter and/or a polarizer, can be included in the internal calibration and/or verification target and be disposed either in front of or behind the aspheric lens to attenuate the light so that it is about the same as that from a real eye. Alternatively, the thickness of the spectralon can be properly selected to only enable a desired amount of light to be diffusely back scattered and/or reflected and the transmitted light can be absorbed by a light absorbing material (not shown in FIG. 8).

One embodiment of the present invention is to interface the front-end processing system 710 with the position sensing detector circuit 725 and the SLD driver and control circuit 715. As the position sensor detector is likely a parallel multiple channel one in order for it to have high enough temporal frequency response, it can be a quadrant detector/sensor, a lateral effect position sensing detector, a parallel small 2D array of photodiodes, or others. In the case of a quadrant detector/sensor or a lateral effect position sensing detector, there are typically 4 parallel signal channels. The front-end processing system computes ratio-metric X and Y values based on signal amplitudes from each of the 4 channels (A, B, C and D) as will be discussed later. In addition to the standard practice, the front-end processing system can (upon user discretion) automatically adjust SLD output and the gain of the variable gain amplifier either independently for each of the channels or together for all the channels so that the final amplified outputs of the A, B, C and D values for all sequentially sampled sub-wavefront image spots landing on the position sensing detector are optimized for optimal signal-to-noise ratio. This is needed because the optical signal returned from a patient eye can vary depending on the refractive state (myopic, emmetropic and hyperopic), the surgical state (phakic, aphakic and pseudo-phakic), and degree of cataract of the eye.

Figure 9A:
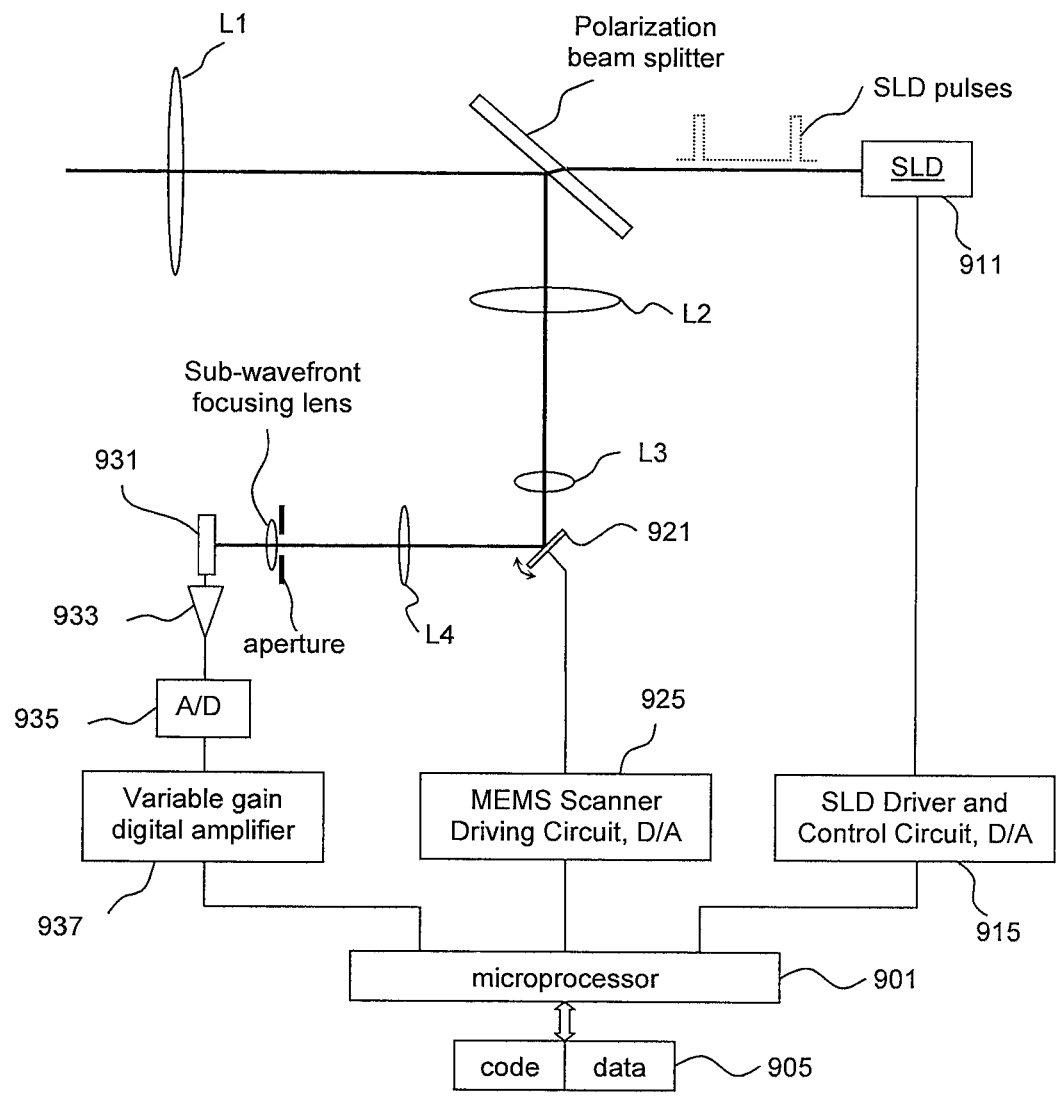
FIG. 9A shows an embodiment of an electronics block diagram that accomplishes the task of automatic SLD index and digital gain control in order to optimize the signal to noise ratio.
Figure 9B:
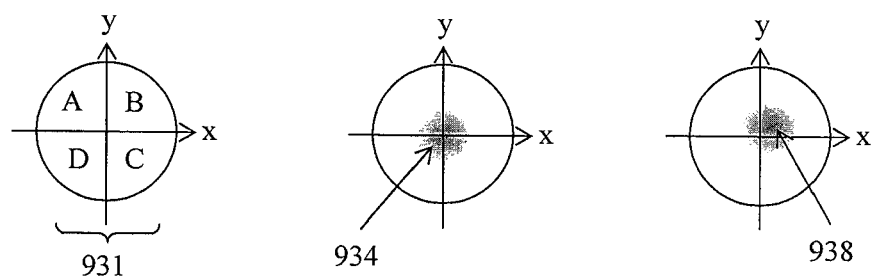
FIG. 9B shows a quadrant detector with firstly a light image spot landing at the center and secondly landing slightly away from the center.
Figure 10:
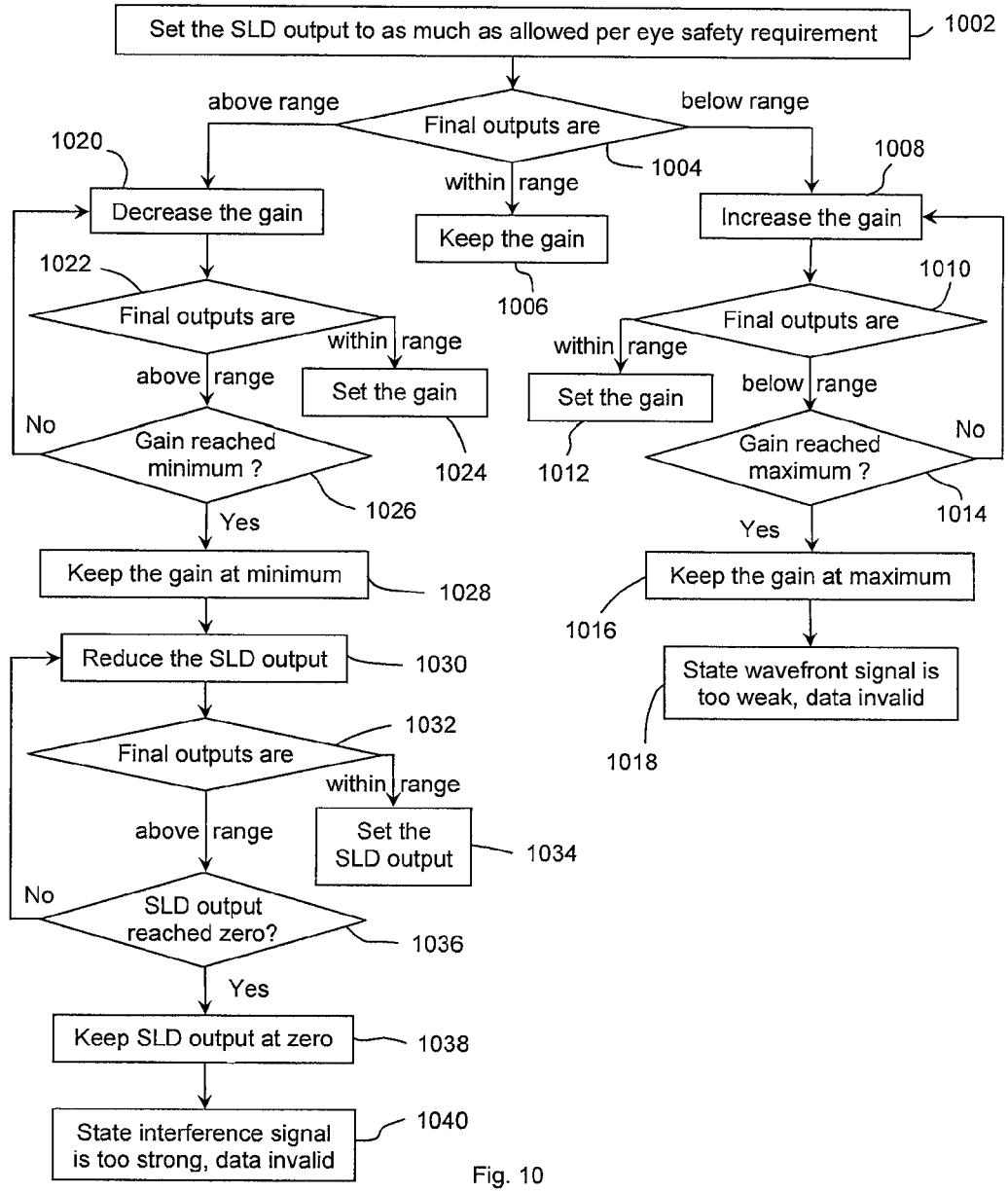
FIG. 10 shows one example process flow block diagram in optimizing the signal to noise ratio by changing the gain of the variable gain amplifier and the SLD output.

FIGS. 9A and 9B show an embodiment of an electronics block diagram that accomplishes the task of automatic SLD index and digital gain control through a servo mechanism in order to optimize the signal to noise ratio, and FIG. 10 shows an example embodiment in the form of a process flow block diagram.

Referring to FIG. 9A, the microprocessor 901 is coupled to a memory unit 905 that has code and data stored in it. The microprocessor 901 is also coupled to the SLD 911 via a SLD driver and control circuit with digital to analog conversion 915, the MEMS scanner 921 via a MEMS scanner driving circuit with digital to analog conversion 925, and the PSD 931 via a composite transimpedance amplifier 933, an analog to digital converter 935 and a variable gain digital amplifier 937.

It should be noted that the PSD in this example is a quadrant detector with four channels that lead to four final amplified digital outputs A, B, C, and D, so correspondingly, there are four composite transimpedance amplifiers, four analog to digital converters and four variable gain digital amplifiers, although in FIG. 9A only one of each is drawn.

To illustrate the points, we will briefly repeat with reference to FIG. 9B what has been discussed in US7445335. Assume that a sequential wavefront sensor is used for wavefront sampling and a PSD quad-detector 931 with four photosensitive areas of A, B, C, and D is used to indicate the local tilt in terms of the centroid position of the sampled sub-wavefront image spot position as shown in FIG. 9B. If the sub-wavefront is incident at a normal angle with respect to the sub-wavefront focusing lens in front of the quad-detector 931, the image spot 934 on the quad-detector 931 will be at the center and the four photosensitive areas will receive the same amount of light, with each area producing a signal of the same strength. On the other hand, if the sub-wavefront departs from normal incidence with a tilting angle (say, pointing toward the right-upper direction), the image spot on the quad-detector will then be formed away from the center (moved towards the right-upper quadrant as shown by the image spot 938).

The departure (x, y) of the centroid from the center (x=0, y=0) can be approximated to a first order using the following equation:

$$x = \frac{(B+C)-(A+D)}{A+B+C+D} \quad (1)$$

$$y = \frac{(A+B)-(C+D)}{A+B+C+D}$$

where A, B, C and D stand for the signal strength of each corresponding photosensitive area of the quad-detector and the denominator (A+B+C+D) is used to normalize the measurement so that the effect of optical source intensity fluctuation can be cancelled. It should be noted that Equation (1) is not perfectly accurate in calculating the local tilt in terms of the centroid position, but it is a good approximation. In practice, there may be a need to further correct the image spot position errors that can be induced by the equation using some mathematics and a built-in algorithm.

Referring to FIG. 10, at the beginning step 1002, the front end microprocessor 901 preferably sets the SLD initially to an output level as much as allowed per eye safety document requirement. The gain of the variable gain digital amplifier 937 at this moment can be initially set at a value determined at the last session or at an intermediate value as would normally be selected.

The next step (1004) is to check the variable gain digital amplifier final outputs A, B, C and D. If the amplified final outputs of A, B, C and D values are found to be within the desired signal strength range, which can be the same for each channel, the process flow moves to the step 1006 at which the gain of variable gain digital amplifier is kept at the set value. If any or all of the final outputs are below the desired signal strength range, the gain can be increased as shown by step 1008 and the final outputs are then checked as shown by step 1010. If the final outputs are within the desired range, the gain can be set as shown by step 1012 at a value slightly higher than the current value to overcome fluctuation induced signal variations that can cause the final outputs to go outside the desired range again. If the final outputs are still below the desired signal strength range and the gain has not reached its maximum as shown to be checked by step 1014, the process of increasing the gain per step 1008 and checking the final outputs per step 1010 can be repeated until the final outputs fall within the range and the gain is set as shown by step 1012. One possible exceptional scenario is that the final outputs are still below the desired range when the gain is already increased to its maximum as shown by step 1014. In this case, the gain will be set at its maximum as shown by step 1016 and data can still be processed, but a statement can be presented to the end user to inform him/her that the wavefront signal is too weak so the data might be invalid as shown by step 1018.

On the other hand, if any of the final outputs A, B, C and D are above the desired signal strength range, the gain of the variable gain digital amplifier can be decreased as shown by step 1020 and the final outputs are checked as shown by step 1022. If all of the final outputs are within the desired range, the gain can be set as shown by step 1024 at a value slightly lower than the current value to overcome fluctuation induced signal variations that can cause the final outputs to go outside the desired range again. If any of the final outputs is still above the desired signal strength range and the gain has not reached its minimum as checked at step 1026, the process of decreasing the gain per step 1020 and checking the final outputs per step 1022 can be repeated until the final outputs all fall within the range and the gain is set as shown by step 1024.

However, there is a possibility that the gain has reached its minimum when checked at step 1026 and one or more of the final outputs A, 13, C and D is(are) still above the desired signal strength range. In this case, the gain is kept at its minimum as shown at step 1028 and the SLD output can be decreased as shown by step 1030. The final outputs A, B, C and D are checked at step 1032 after the SLD output is decreased and if it is found that the final A, B, C and D outputs are within the desired range, the SLD output is then set as shown by step 1034 at a level slightly lower than the current level to overcome fluctuation induced signal variations that can cause the final outputs to go outside the desired range again. If one or more of the final outputs A, B, C and D is(are) still above the desired range and the SLD output has not reached zero per the checking step of 1036, the process of decreasing the SLD output as shown by step 1030 and checking the final A, B, C and D outputs as shown by step 1032 can be repeated until they reach the desired range and the SLD output is set as shown by step 1034. The only exception is that the SLD output has reached zero and one or more of the final A, B, C and D outputs is(are) still above the desired range. This means that even if there is no SLD output; there is still a strong wavefront signal. This can only happen when there is either electronic or optical interference or cross talk. We can keep the SLD output at zero as shown by step 1038 and send the end user a message that there is strong interference signal so data is invalid as shown by step 1040.

In addition to the above, as an alternative, the end user can also manually control the SLD output and the gain of the variable gain digital amplifier until he/she feels that the real wavefront measurement result is satisfactory.

It should be noted that the example embodiment given in FIGS. 9A and 9B and FIG. 10 is only one of many possible ways to achieve the same goal of improving the signal to noise ratio, so it should be considered as illustrating the concept. For example, at the beginning step, there is no absolute need to set the SLD output to the level as much as allowed per eye safety document requirement. The SLD output can be initially set at any arbitrary level and then adjusted together with amplifier gain until the final outputs A, B, C and D fall within the desired range. The advantage of setting the SLD output initially to a relatively high level is that in the optics or photonics domain, the optical signal to noise ratio before any opto-electronic conversion can be maximized. However, this does not mean that other choices would not work. In fact, the SLD output can even be initially set at zero and gradually increased together with the adjustment of the amplifier gain until the final A, B, C and D outputs fall within the desired range. In this case, there will be a corresponding change to the sequence and details of the process flow. These variations should be considered as within the scope and spirit of the present disclosure.

Figure 11:
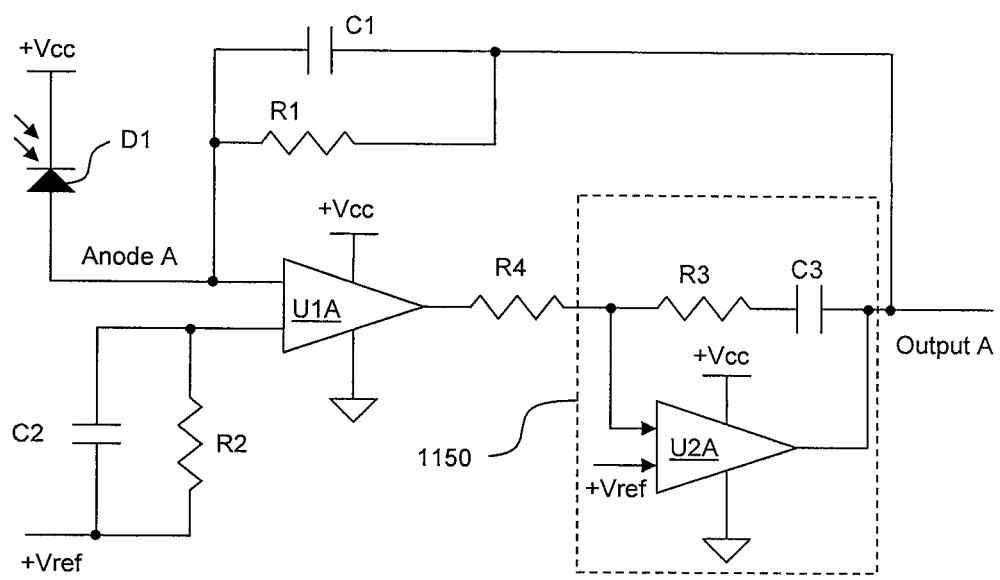
FIG. 11 shows one example embodiment of a composite transimpedance amplifier with lock-in detection that can be used to amplify the signal from any one of the four quadrant photodiodes, as is used in the position sensing detector circuit of FIG. 9.

Another embodiment of the present disclosure is to use a composite transimpedance amplifier to amplify the position signal of a sequential ophthalmic wavefront sensor. FIG. 11 shows one example embodiment of a composite transimpedance amplifier that can be used to amplify the signal from any one quadrant (for example, D1) of the four quadrant photodiodes of a quadrant detector. The circuit is used in the position sensing detector circuit as shown in FIG. 9A. In this composite transimpedance amplifier, the current-to-voltage conversion ratio is determined by the value of the feedback resistor R1 (which, for example, can be 22 MegOhms) and is matched by resistor R2 to balance the inputs of the op-amp U1A. The shunt capacitors C1 and C2 could be either parasitic capacitance of resistors R1 and R2 or small capacitors added to the feedback loop. The transimpedance amplifier's stability and high-frequency noise reduction comes from the low-pass filter formed by resistor R3, capacitor C3 and op-amp U2A inside the feedback loop 1150. In this circuit, +Vref is some positive reference voltage between ground and +Vcc. Since the output signal (Output A) is proportional to R1, but noise is proportional to the square root of RE the signal-to-noise ratio therefore increases proportionally to the square root of R1 (since it is dominated by the Johnson noise of R1).

Note that prior art high-bandwidth wavefront sensors generally only use standard transimpedance amplifier(s) rather than composite transimpedance amplifier(s) (see, for example, S. Abado, et. al. "Two-dimensional High-Bandwidth Shack-Hartmann Wavefront Sensor: Design Guidelines and Evaluation Testing", Optical Engineering, 49(6), 064403, June 2010.). In addition, prior art wavefront sensors are not purely sequential but parallel in one way or another. Furthermore, they do not face the same weak but synchronized and pulsed optical signal challenge as the present sequential ophthalmic wavefront sensor faces. Features that, when combined in one way or another, are uniquely associated with the presently disclosed composite transimpedance amplifier in terms of its application to the amplification of the optical signal in a sequential ophthalmic wavefront sensor include the following: (1) In order to improve the current to voltage conversion precision, the selected feedback resistor value of R1 that is substantially matched by resistor R2 is very high; (2) In order to reduce the noise contribution from the large resistance value of R1 and R2 while maintaining adequate signal bandwidth, the two shunt capacitors C1 and C2 have very low capacitance values; (3) The low-pass filter formed by R3, C3 and U2A inside the feedback loop substantially improves the stability and also substantially reduces the high-frequency noise of the transimpedance amplifier; (4) To achieve lock-in detection, the positive reference voltage+ Vref is a properly scaled DC signal phase-locked to the drive signal of the SLD and the MEMS scanner, and it is between ground and +Vcc. Furthermore, to achieve optimal signal to noise ratio, a quadrant sensor with minimal terminal capacitance is preferably selected; and to avoid any shunt conductance between any two of the four quadrants, good channel isolation between the quadrants is preferred.

Figure 12:
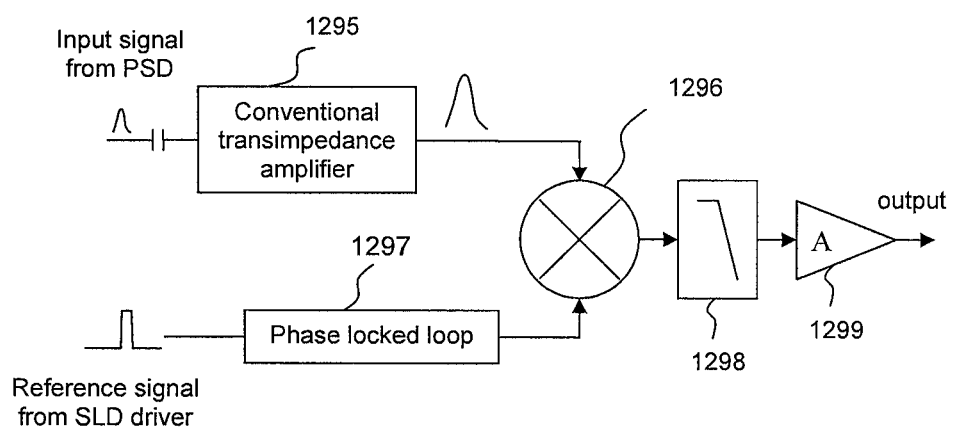
FIG. 12 shows one example embodiment of the combination of a conventional transimpedance amplifier with a lock-in detection circuit.

In addition to the above circuit, the optical signal converted to an analog current signal by the position sensing detector can also be AC coupled to and amplified by a conventional transimpedance amplifier, and then combined with a standard lock-in detection circuit to recover small signals which would otherwise be obscured by noises that can be much larger than the signal of interest. FIG. 12 shows one example embodiment of such a combination. The output signal from the transimpedance amplifier 1295 is mixed at a mixer 1296 with (i.e. multiplied by) the output of a phase-locked loop 1297 which is locked to the reference signal that drives and pulses the SLD. The output of the mixer 1296 is passed through a low-pass filter 1298 to remove the sum frequency component of the mixed signal and the time constant of the low-pass filter is selected to reduce the equivalent noise bandwidth. The low-pass filtered signal can be further amplified by another amplifier 1299 for analog to digital (A/D) conversion further down the signal path.

An alternative to the above lock-in detection circuit is to activate the A/D conversion just before the SLD is illuminated to record a "dark" level, and activate the A/D conversion just after the SLD is illuminated to record a "light" level. The difference can then be computed to remove the effects of interference. Yet another embodiment is to activate the A/D conversion just after the SLD is illuminated or record a "light" level while ignoring the "dark" levels if interference effects are minimal.

In addition to the optical signal detection circuit, the next critical electronically controlled component is the wavefront scanner/shifter. In one embodiment, the wavefront scanner/ shifter is an electromagnetic MEMS (Micro-Electro-Mechanical System) analog steering mirror driven by four D/A converters controlled by the microprocessor. In one example, two channels of D/A converters output sinusoids 90 degrees apart in phase, and the other two channels output X and Y DC-offset voltages to steer the center of the wavefront sampling annular ring. The amplitude of the sine and cosine electronic waveforms determines the diameter of the wavefront sampling annular ring, which can be varied to accommodate various eye pupil diameters as well as to deliberately sample around one or more annular ring(s) of the wavefront with a desired diameter within the eye pupil area. The aspect ratio of the X and Y amplitude can also be controlled to ensure that a circular scanning is done when the mirror reflects the wavefront beam sideways.

FIGS. 13A to 13F illustrate how synchronizing the MEMS scanner and SLD pulses create the same result as if the wavefront were sampled by multiple detectors arrayed in a ring.

Figure 13A:
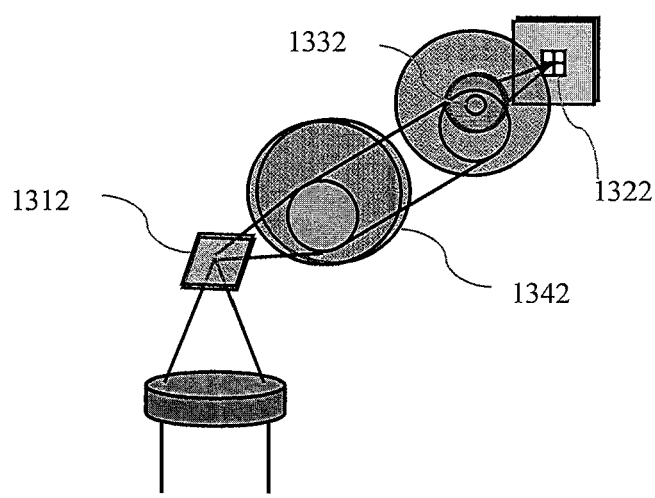
FIG. 13A shows the case when the MEMS scan mirror is oriented so that the entire wavefront is shifted downward as the SLD pulse is fired. In this case the aperture samples a portion at the top of the circular wavefront section.
Figure 13B:
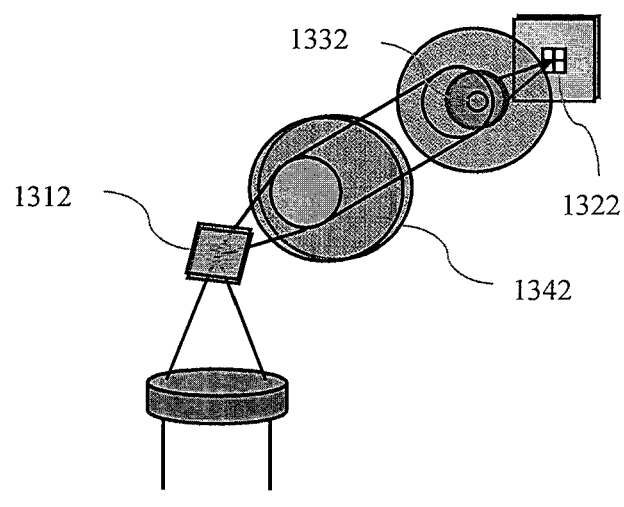
FIG. 13 B shows the case when the wavefront shifted leftward as the SLD pulse is fired so that the aperture samples a portion at the right of the of the circular wavefront section.
FIG. 13C shows that case when the wavefront is shifted upward as the SLD pulse is fired so that the aperture samples a portion at the bottom of the of the circular wavefront section.
FIG. 13D shows the case when the wavefront is shifted rightward as the SLD pulse is fired so that the aperture samples a portion at the left of the of the circular wavefront section.
FIG. 13E depicts the equivalence of the sequential scanning sequence of four pulses per cycle to sampling the wavefront section with four detectors arranged in a ring.
FIG. 13F shows the positions of 8 SLD pulse firing relative to the X and Y axes of the MEMS scanner with 4 odd or even numbered pulses of the 8 pulses aligned with the X and Y axes of the MEMS scanner and the other 4 pulses arranged midway on the ring between the X and Y axes.

In FIG. 13A the MEMS 1312 is oriented so that the entire wavefront is shifted downward when the SLD pulse is fired. In this case the aperture 1332 samples a portion at the top of the circular wavefront section.

Figure 13C:
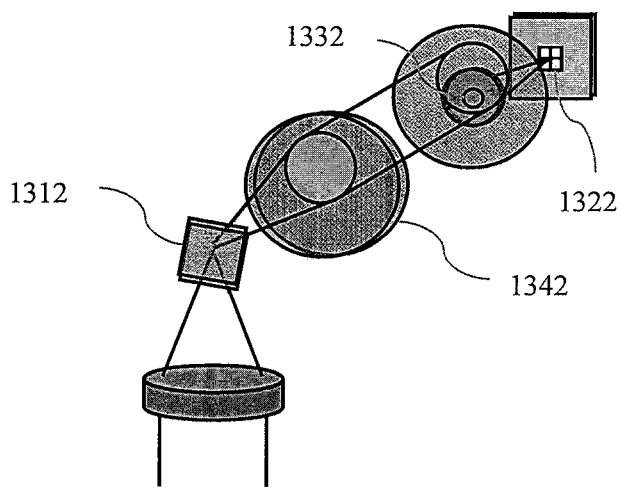
Figure 13D:
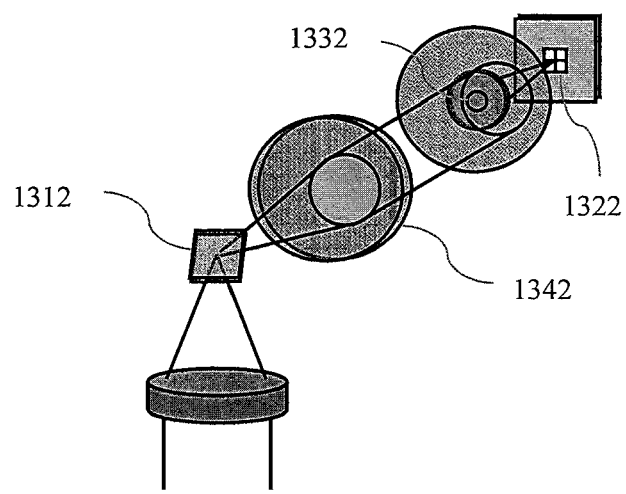

In FIG. 13 B the wavefront shifted leftward so that the aperture samples a portion at the right of the of the circular wavefront section, in FIG. 13C the wavefront is shifted upward so that the aperture samples a portion at the bottom of the of the circular wavefront section and in FIG. 13D the wavefront is shifted rightward so that the aperture samples a portion at the left of the of the circular wavefront section.

Figure 13E:
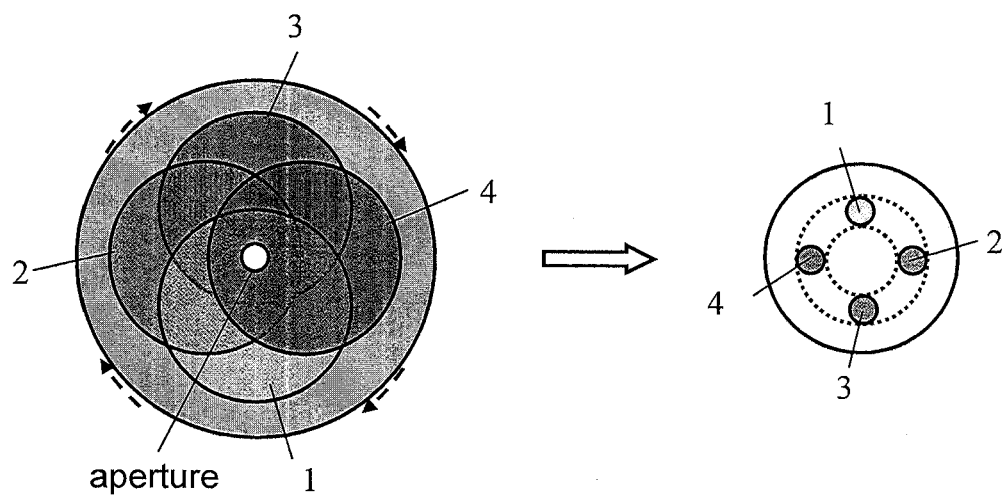

FIG. 13E depicts the equivalence of the sequential scanning sequence of four pulses per cycle to sampling the wavefront section with four detectors arranged in a ring.

Figure 13F:
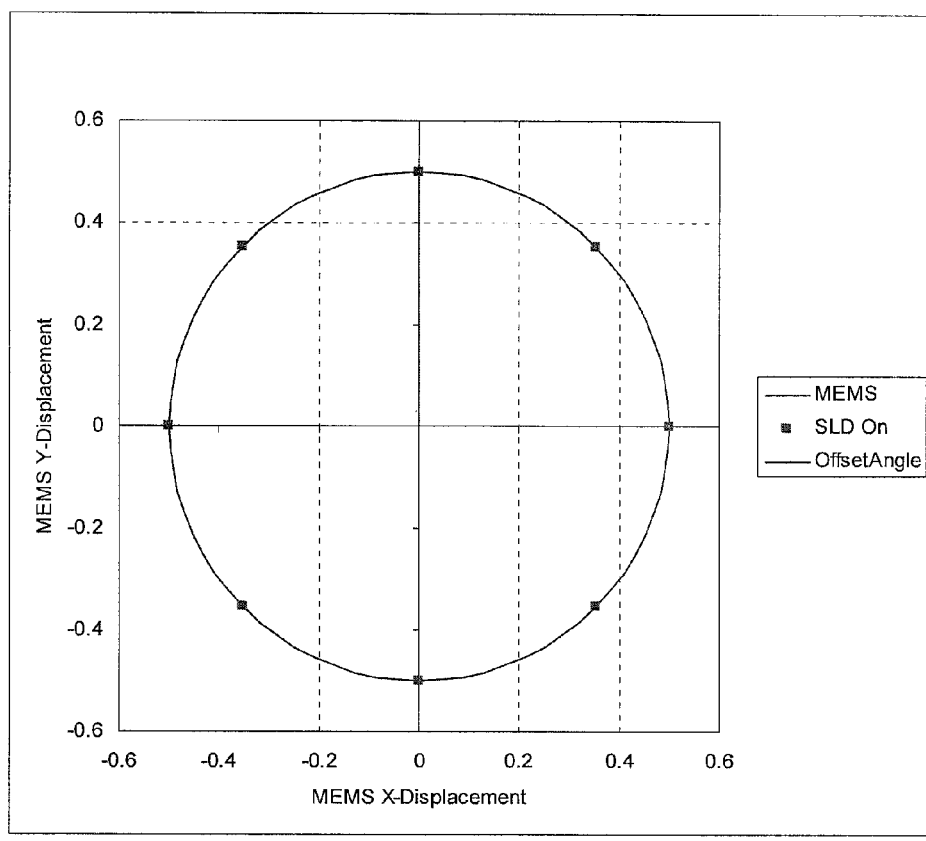

In another example, the SLD can be synchronized with the MEMS scanner and 8 SLD pulses can be fired to allow 8 sub-wavefronts to be sampled per each MEMS scanning rotation and hence each wavefront sampling annular ring rotation. The SLD pulse firing can be timed such that 4 odd or even numbered pulses of the 8 pulses are aligned with the X and Y axes of the MEMS scanner and the other 4 pulses are arranged midway on the ring between the X and Y axes. FIG. 13F shows the resulting pattern of the MEMS scanning rotation and the relative SLD firing positions. It should be noted that the number of SLD pulses does not need to be restricted to 8 and can be any number, the SLD pulses do not need to be equally spaced in time, and they do not have to be aligned with the X and Y axes of the MEMS scanner.

Figure 14:
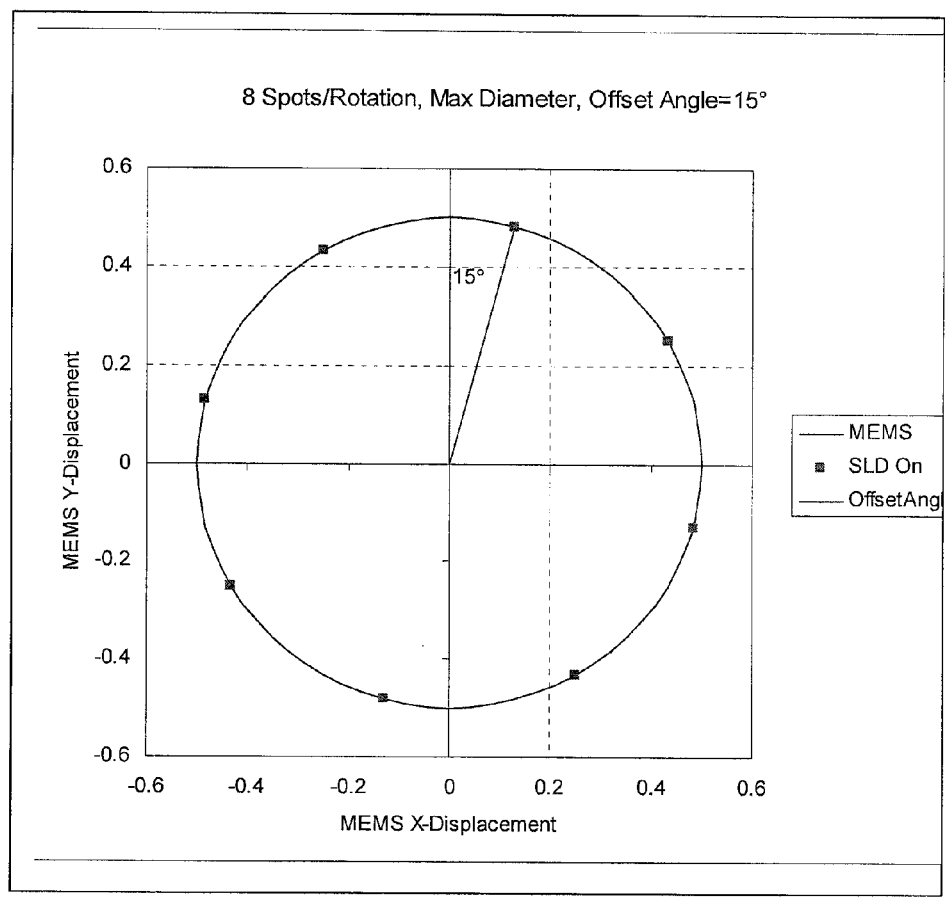
FIG. 14 shows an example in which the 4 SLD pulse firing positions initially aligned with the X and Y axes of the wavefront scanner as shown in FIG. 13F are shifted 15° away from the X and Y axes by slightly delaying the SLD pulses.

As an alternative, for example, by changing the relative timing and/or the number of pulses of SLD firing with respect to the driving signal of the MEMS scanner, we can shift the wavefront sampling positions along the wavefront sampling annular ring to select the portion of the wavefront to be sampled and also to achieve higher spatial resolution in terms of sampling the wavefront. FIG. 14 shows an example in which the 8 wavefront sampling positions are shifted 15° away from those shown in FIG. 13F by slightly delaying the SLD pulses.

Figure 15:
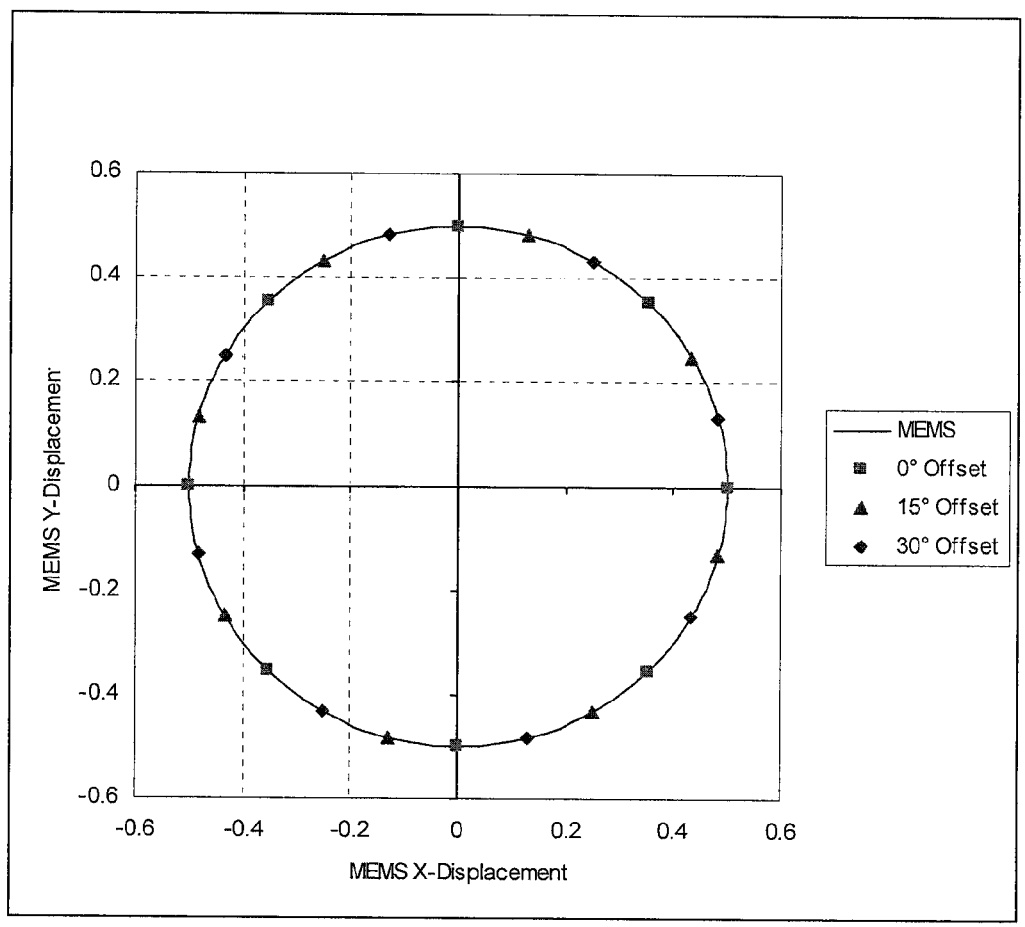
FIG. 15 shows the collective effect of sampling a wavefront with offset angle at 0° on the first frame, 15° on the second frame, and 30° on the third.

As another alternative, if we sample the wavefront with offset angle at 0° on the first frame, 15° on the second frame, and 30° on the third frame and repeat this pattern, we can sample the wavefront with increased spatial resolution when data from multiple frames are collectively processed. FIG. 15 shows such a pattern. Note that this frame-by-frame gradual increase in the initial firing time of the SLD can be implemented with any desired but practical timing precision to achieve any desired spatial resolution along any annular wavefront sampling ring. In addition, by combining the change in the amplitude of the MEMS scanner's sinusoidal and co-sinusoidal drive signals, we can also sample different annular rings with different diameters. In this way, sequential sampling of the whole wavefront can be achieved with any desired spatial resolution in both the radial and also angular dimension of a polar coordinate system. It should be noted that this is only one example of many possible sequential wavefront scanning/sampling schemes. For example, a similar approach can be applied to the case of raster scanning.

As described above, with reference to FIG. 9B, in terms of interpreting the centroid position of different sequentially sampled sub-wavefront image spots landing on the position sensing device/detector (PSD), standard well known ratiometric equations can be used. It is preferred that a quadrant detector or lateral-effect position sensing detector is used as the PSD and its X-Y axis is aligned in orientation to that of the MEMS scanner so that they have the same X and Y axis, although this is not absolutely required. In the case of, for example, a quadrant detector, the ratiometric X and Y values of a sequentially sampled sub-wavefront image spot can be expressed based on the signal strength from each of the four quadrants, A, B, C, and D as:

$$X=(A+B-C-D)/(A+B+C+D)$$

$$Y=(A+D-B-C)/(A+B+C+D)$$

In general, these ratiometric values of X and Y do not directly give highly accurate transverse displacement or position of the centroids, because the response of, for example, a quadrant detector is also a function of gap distance, the image spot size which is dependent on a number of factors, including the local average tilt and the local divergence/convergence of the sampled sub-wavefront, as well as the sub-wavefront sampling aperture shape and size. One embodiment of the present invention is to modify the relationship or equation so that the sampled sub-wavefront tilt can be more precisely determined.

Figure 16:
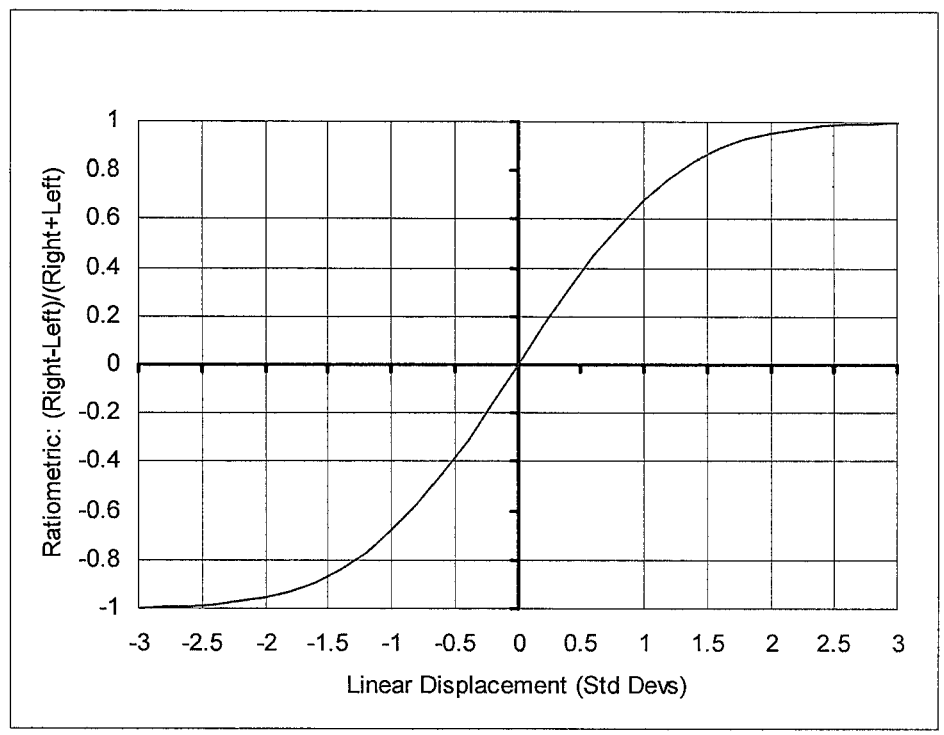
FIG. 16 shows one example of a theoretically determined relationship between the PSD ratiometric estimate and the actual centroid displacement or position along either the X or the Y axis.

In one embodiment, the relationship between the ratiometric measurement result and the actual centroid displacement is theoretically and/or experimentally determined and the ratiometric expression is modified to more accurately reflect the centroid position. FIG. 16 shows one example of a theoretically determined relationship between the ratiometric estimate and the actual centroid displacement or position along either the X or the Y axis.

Because of this non-linearity, an approximate inverse of the effect can be applied to the original equation to result in a modified relationship between the ratiometric (X, Y) and the actual centroid position (X', Y'). Below is just one example of such an inverse relationship.

$$X'=\text{Prime}A*X/(1-X^2/\text{Prime}B)$$

$$Y'=\text{Prime}B*Y/(1-Y^2/\text{Prime}B)$$

where PrimeA and PrimeB are constants.

It should be noted that the relationship or equation shown above is illustrative, it is not intended to be a limitation to the possible approaches that can be used to achieve the same goal. In fact, the above modification is for the centroid position of a sampled sub-wavefront of a certain intensity profile when its image spot is displaced along only the X or Y axis. If the image spot is displaced in both X and Y, further modification will be required, especially if higher measurement precision is desired. In one example embodiment, an experimentally determined relationship in the form of data matrix or matrices between the quadrant detector reported ratiometric result in terms of (X, Y) and the actual centroid position (X', Y') can be established, and a reversed relationship can be established to convert each (X, Y) data point to a new centroid (X', Y') data point.

Figure 17:
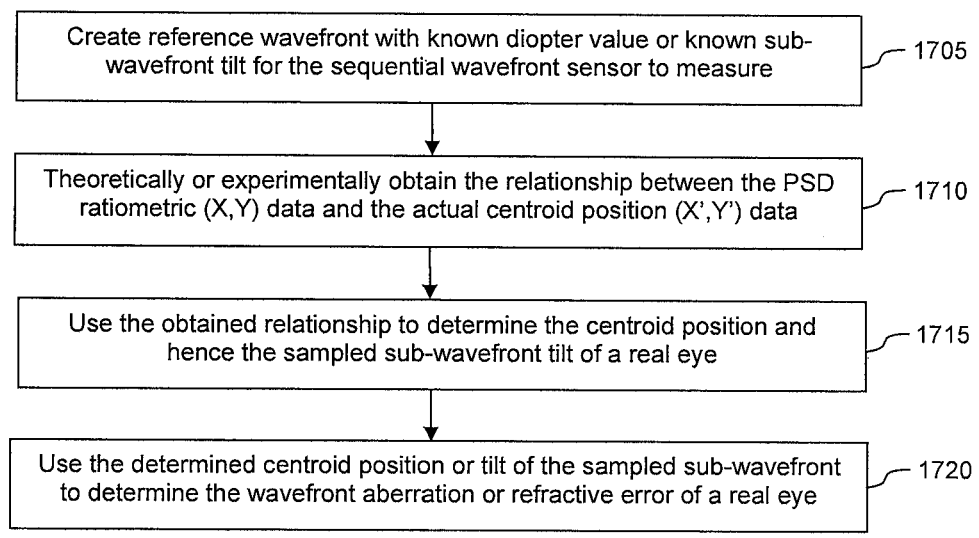
FIG. 17 shows an example flow diagram that illustrates how calibration can be performed to obtain a modified relationship and to result in more accurate wavefront aberration measurement.

FIG. 17 shows an example flow diagram that illustrates how calibration can be performed to obtain a modified relationship and to result in more accurate wavefront aberration measurement. In the first step 1705, a wavefront can be created using various means such as from an eye model or from a wavefront manipulator like a deformable mirror that can produce different wavefront such as with different divergence and convergence or with different wavefront aberrations. In the second step 1710, the real centroid position (X', Y') of different sampled sub-wavefronts can be compared to the experimentally measured ratiometric values (X, Y) to obtain the relationship between (X', Y') and (X, Y). Meanwhile, the calibrated wavefront tilt and hence dioptric value versus the centroid data point position can be obtained. In the third step 1715, a measurement can be made of a real eye and the obtained relationship can be used to determine the centroid position and hence the sampled sub-wavefront tilts from the real eye. In the fourth step 1720, the determined centroid position or tilt of the sampled sub-wavefront can be used to determine the wavefront aberration or refractive errors of the real eye.

It should be noted that the first and second calibration related steps can be executed once for each built wavefront sensor system and the third and fourth steps can be repeated for as many real eye measurements as one likes. However, this does not mean that the calibration steps should be done only once. In fact it is beneficial to periodically repeat the calibration steps.

As one embodiment of the present disclosure, the calibration steps or a partial calibration can be repeated as often as the manufacturer or an end user prefers using an internal calibration target driven by the microprocessor as shown in FIG. 9A. For example, an internal calibration target can be moved into the optical wavefront relay beam path temporarily every time the system is powered up or even before each real eye measurement automatically or manually as desired by the end user. The internal calibration does not need to provide all the data points as a more substantially comprehensive calibration would or can provide. Instead, the internal calibration target only needs to provide some data points. With these data points, one can experimentally confirm if the optical alignment of the wavefront sensor is intact or if any environmental factor such as temperature change and/or mechanical impact has disturbed the optical alignment of the wavefront sensor. Accordingly, this will determine if a completely new comprehensive calibration needs to be conducted or if some minor software based correction will be sufficient to ensure an accurate real eye wavefront measurement. Alternatively, the measured reference wavefront aberration using an internal calibration target can figure out the inherent optical system aberration that the wavefront sensor optical system has and the real eye wavefront aberration can be determined by subtracting the optical system induced wavefront aberration from the measured overall wavefront aberration.

As another embodiment of the present disclosure, a calibration target (internal or external) can also be used to determine the initial time delay between the SLD firing pulse and the MEMS mirror scanning position, or the offset angle between the sub-wavefront sampling position and the MEMS mirror scanning position along a certain wavefront sampling annular ring. The same calibration steps can also be used to determine if the SLD firing time is accurate enough with respect to the MEMS scan mirror position, and if there is any discrepancy from a certain desired accuracy, either an electronics hardware based correction or a pure software based correction can then be implemented to fine tune the SLD firing time or the MEMS scanning drive signal.

As still another embodiment of the present disclosure, if the calibration (internal or external) detects that the optical alignment is off or if in a real eye measurement case that the eye is found not positioned at the best position, but within a range that wavefront measurement can still be done with software correction, then software based adjustment can be performed to cater for such a misalignment as explained with reference to FIG. 4.

In another example embodiment, if 8 sub-wavefronts are sampled around an annular ring of a wavefront produced from either a calibration target or from a real eye and it is found that there is a centroid trace center offset of the 8 measured sub-wavefront tilts as a result of, for example, a PSD transverse position shift or a prismatic wavefront tilt of the wavefront from the patient eye (X'(i), Y'(i)), where i=0, 1, 2, . . . , 7, then a translation of the (X', Y') Cartesian coordinate can be performed so that the 8 data points are given a new Cartesian coordinate (Xtr,Ytr) and are expressed as a new set of data points (Xtr(i), Ytr(i)), where i=0, 1, 2, . . . , 7, with the cluster center of the centroid data points now centered at the new origin (Xtr=0, Ytr=0). In this way, any effect that leads to the appearance of an overall prismatic wavefront tilt resulting, for example, from a misalignment between the sub-wavefront sampling aperture and the position sensing detector/device, can be filtered out from the measured wavefront. As a result, the rest of the data processing can be focused on figuring out the refractive errors and/or the higher order aberrations of the wavefront.

Note that sequential wavefront sampling has the inherent advantage that it can correlate where we are sampling on an annular ring to the displacement of each individually sampled sub-wavefront centroid position.

Figure 9C:
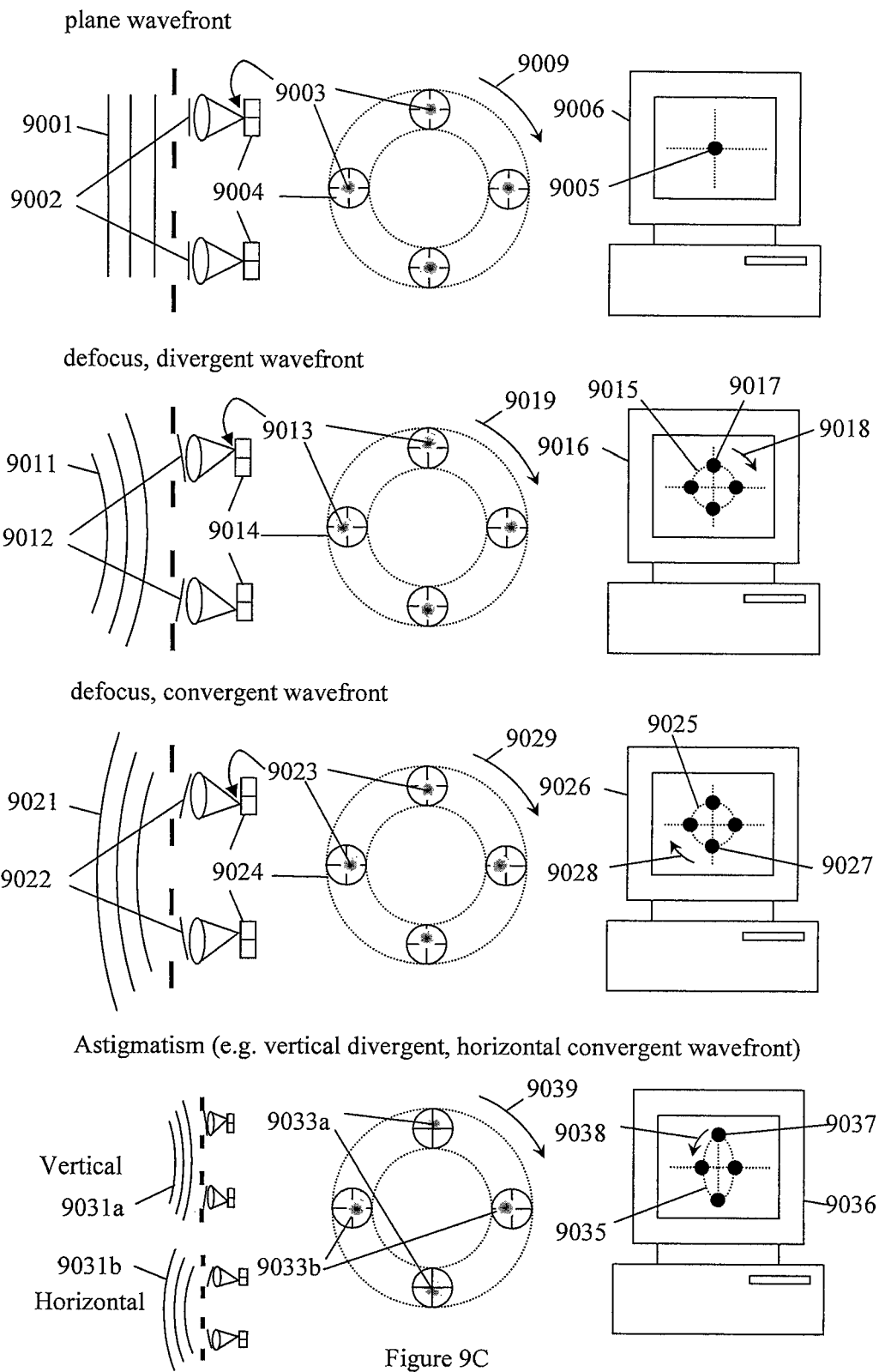
FIG. 9C shows a number of representative cases of planar wavefront, defocus and astigmatism, the associated image spot position on a quad-detector behind a subwavefront focusing lens, as well as the sequential movement of the corresponding centroid positions when displayed as a 2D data point pattern on a monitor.

As described above, the displacements of the centroids of the sampled wavefront portions are determined using the ratiometric X and Y values calculated from the output signals generated by the PSD. The positions of these output values form geometric patterns that can be analyzed by the front-end or backend electronic processing system to determine ophthalmic characteristics of a subject eye. The formation and analysis of these patterns are illustrated in FIG. 9C. In FIG. 9C the displacements are depicted as if they were displayed on monitor. However, in other example embodiments the displacements are processed by algorithms executed as software by the front end processing system and are not necessarily displayed to a user.

FIG. 9C shows a number of representative cases of planar wavefront, defocus and astigmatism, the associated image spot position on the quad-detector behind the sub-wavefront focusing lens, as well as the sequential movement of the corresponding centroid positions when displayed as a 2D data point pattern on a monitor. Note that instead of drawing a number of shifted wavefronts being sampled and projected as different sub-wavefronts onto the same sub-wavefront focusing lens and the quad-detector, we have taken the equivalent representation, described above with reference to FIGS. 13A-E, such that a number of sub-wavefronts are drawn around the same annular ring and accordingly, a number of quad-detectors are drawn around the same annular ring to represent the case of scanning different portions of a wavefront to a single sub-wavefront focusing lens and a single quad-detector.

Assume that we start the scan around the wavefront annular ring from the top sub-wavefront and move in a clockwise direction to the second sub-wavefront on the right and so forth as indicated by the arrow 9009. It can be seen from FIG. 9C that when the wavefront is a plane wave 9001, all the sub-wavefronts (for example, 9002) will form an image spot 9003 at the center of the quad-detector 9004 and as a result, the centroid trace 9005 on a monitor 9006 will also be always at the origin of the x-y coordinate.

When the input wavefront is divergent as shown by 9011, the center of the image spot 9013 of each sub-wavefront 9012 will be on the radially outward side from the wavefront center with an equal amount of departure from the center of the quad-detector 9014, and as a result, the trace 9015 on the monitor 9016 will be a clockwise circle as indicated by the arrow 9018 starting from the top position 9017. If, on the other hand, the input wavefront is convergent as shown by 9021, the center of the image spot 9023 of each sub-wavefront 9022 will be on the radially inward side relative to the center of the wavefront with an equal amount of departure from the center of the quad-detector 9024. As a result, the centroid trace 9025 on the monitor 9026 will still be a circle but will start from the bottom position 9027 and will still be clockwise as indicated by the arrow 9028. Hence when a sign change for both the x-axis centroid position and the y-axis centroid position is detected, it is an indication that the input wavefront is changing from a divergent beam to a convergent beam or the other way round. Furthermore, the starting point of the centroid trace can also be used as a criterion to indicate if the input wavefront is divergent or convergent.

It can also be seen from FIG. 9C that when the input wavefront is astigmatic, it can happen that the wavefront can be divergent in the vertical direction as shown by 9031a and convergent in the horizontal direction as shown by 9031b. As a result, the centroid position of the vertical sub-wavefronts 9033a will be located radially outward with respect to the center of the input wavefront, and the centroid position of the horizontal sub-wavefronts 9033b will be located radially inward with respect to the center of the input wavefront. Consequently, the centroid trace 9035 on the monitor 9036 will start from the top position 9037 but move anti-clockwise as indicated by arrow 9038, hence the centroid trace rotation is now reversed.

Using a similar argument, it is not difficult to figure out that if the input wavefront is astigmatic but all the sub-wavefronts are either entirely divergent or entirely convergent, the rotation of the centroid trace will be clockwise (i.e. not reversed), however, for the astigmatic case, the trace of the centroid on the monitor will be elliptic rather than circular since the sub-wavefronts along one astigmatic axis will be more divergent or convergent than those along the other axis.

For a more general astigmatic wavefront, either the centroid trace will rotate in the reversed direction with the trace either elliptical or circular, or the centroid trace will rotate in the normal clockwise rotation direction but the trace will be elliptical. The axis of the ellipse can be in any radial direction relative to the center, which will indicate the axis of the astigmatism. In such a case, 4 sub-wavefronts around an annular ring may not be enough in precisely determining the axis of the astigmatism and more sub-wavefronts (such as 8, 16 or 32 instead of 4) can be sampled around an annular ring.

To summarize, for a divergent spherical wavefront versus a convergent spherical wavefront coming, for example, from a human eye, the sequentially sampled sub-wavefronts around an annular ring of the eye pupil will result in the sequential centroid data points being arranged around a circle, but with each data point landing at different opposing locations depending on whether the wavefront is divergent or convergent. In other words, for a divergent wavefront, for example, if we expect a certain data point (e.g. i=0) to be at a certain location (e.g. (Xtr(0), Ytr(0))=(0, 0.5); then for a convergent wavefront of the same of spherical radius but a different sign, we expect the same data point to be at an opposing location (e.g. (Xtr(0), Ytr(0))=(0, −0.5). On the other hand, if the original wavefront has both spherical and cylindrical component, the centroid data points will trace out an ellipse that can be a normal rotation ellipse, a straight line, an abnormal or reverse rotation ellipse, and an abnormal or reverse rotation circle. These scenarios have been discussed in detail in co-assigned U.S. Pat. No. 7,445,335 and co-assigned U.S. Pat. No. 8,100,530.

One embodiment of the present disclosure is to use both positive and negative values of major and minor axes to describe the centroid data points as an equivalent ellipse. For example, an overall divergent wavefront can be defined as having a positive major and minor axis and an overall convergent wavefront can be defined as producing a "negative" major and mirror axis.

Figure 18:
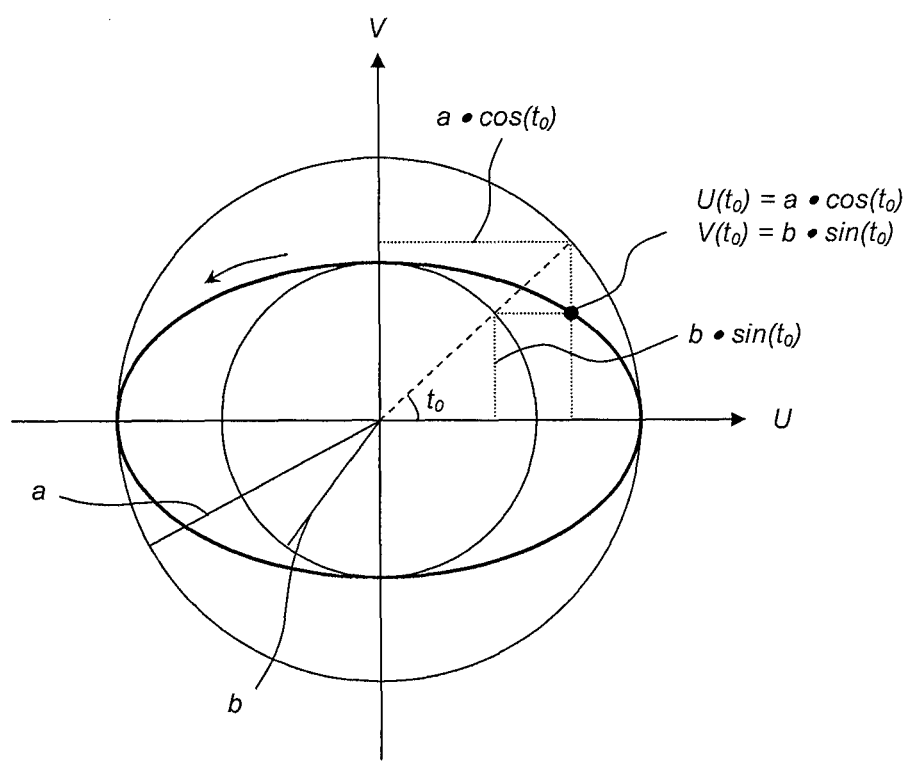
FIG. 18 shows a graphical representation of a sequential ellipse using trigonometry expressions, where $U(t)=a \cdot \cos(t)$ and $V(t)=b \cdot \sin(t)$, $a>b>0$, resulting in an ellipse that rotates counter-clockwise with the point $(U(t_0), V(t_0))$ in the first quadrant of the U-V Cartesian coordinate.

FIG. 18 shows a graphical representation of a sequential ellipse using trigonometry expressions, where $U(t)=a \cdot \cos(t)$, $V(t)=b \cdot \sin(t)$, a is the radius of the bigger circle and b is the radius of the smaller circle. As can be seen, with $a>b>0$ i.e. both a and b are positive, the ellipse rotates counter-clockwise. Thus the points on the ellipse can represent the sequentially calculated centroid displacements of an overall divergent wavefront with both spherical and cylindrical refractive error components where the degree of divergence is different for the horizontal and vertical directions. If $a=b$, the ellipse would represent a divergent spherical wavefront where the degree of divergence is the same for the horizontal and vertical directions. Assume a $t_0$ value of $0<t_0<\pi/2$, the point $(U(t_0), V(t_0))$ will be in the first quadrant of the U-V Cartesian coordinate.

Figure 19:
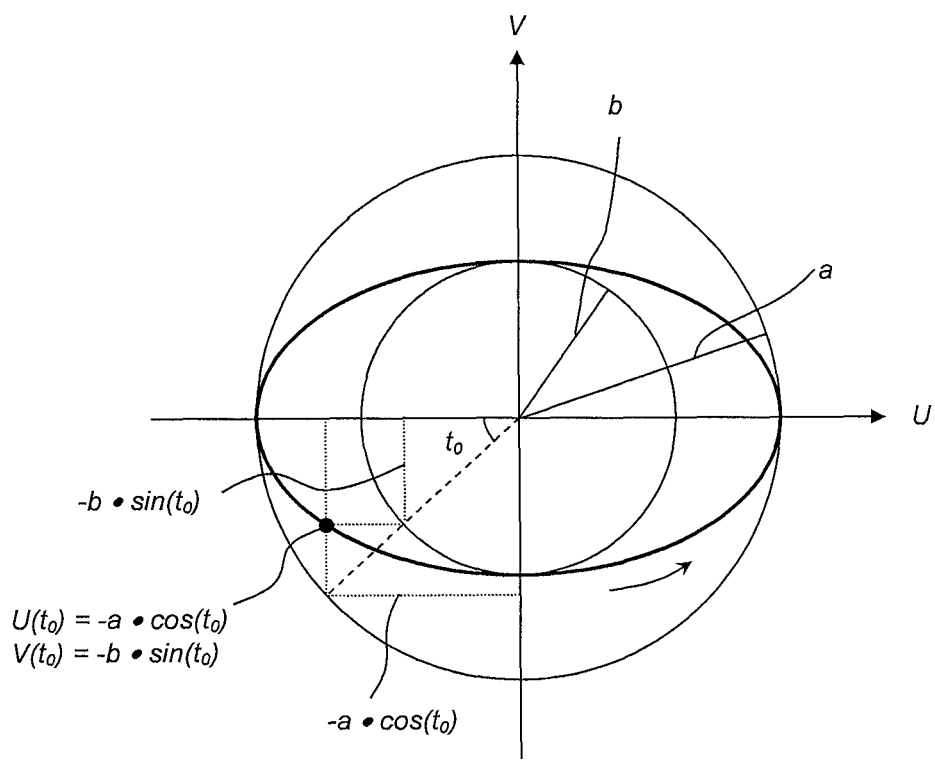
FIG. 19 shows a corresponding graphical representation of a similar sequential ellipse using trigonometry expression, where $U(t)=-a \cdot \cos(t)$, $V(t)=-b \cdot \sin(t)$, $a>b>0$, resulting in an ellipse that rotates counter-clockwise with the point $(U(t_0), V(t_0))$ in the third quadrant of the U-V Cartesian coordinate.
Figure 20:
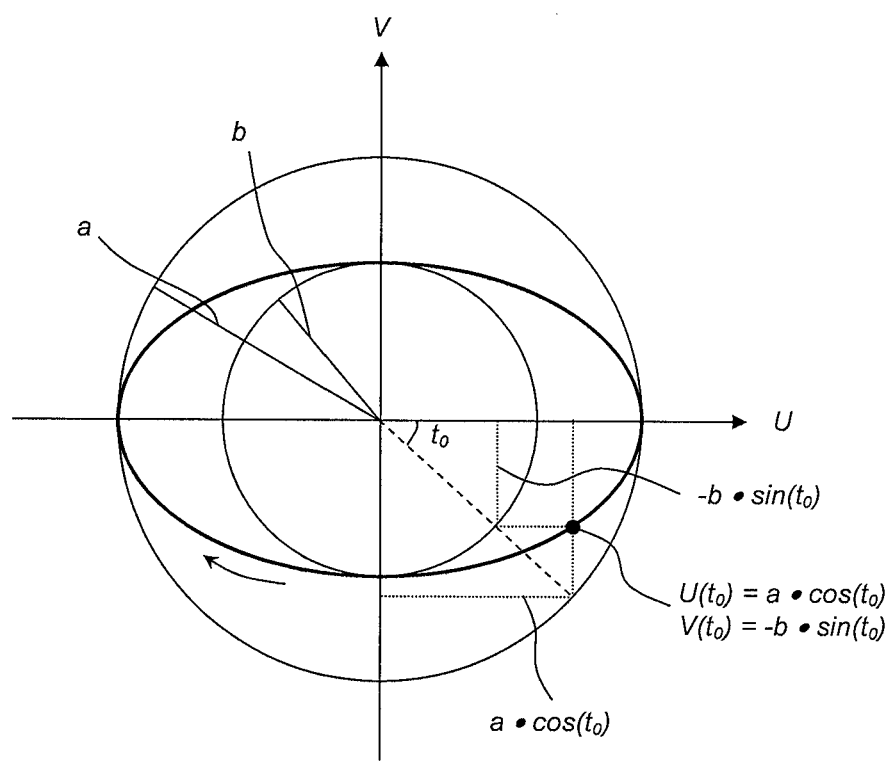
FIG. 20 shows a corresponding graphical representation of a similar sequential ellipse using trigonometry expression, where $U(t)=a \cdot \cos(t)$, $V(t)=-b \cdot \sin(t)$, $a>b>0$, resulting in an ellipse that rotates clockwise with the point $(U(t_0), V(t_0))$ in the fourth quadrant of the U-V Cartesian coordinate.
Figure 21:
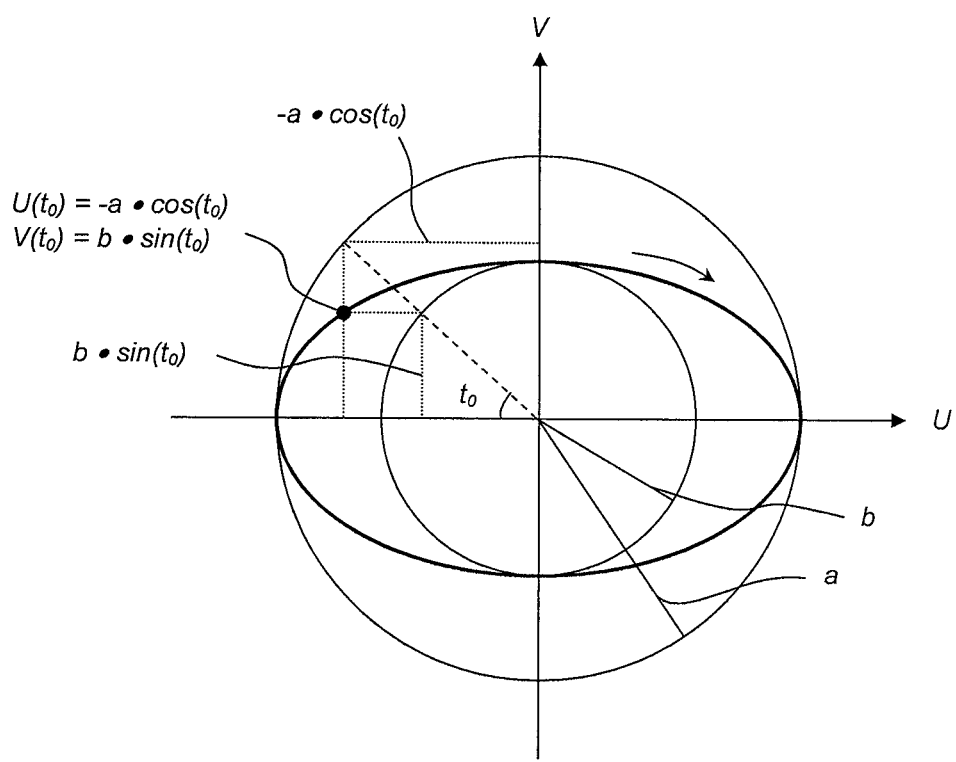
FIG. 21 shows a corresponding graphical representation of a similar sequential ellipse using trigonometry expression, where $U(t)=-a \cdot \cos(t)$, $V(t)=b \cdot \sin(t)$, $a>b>0$, resulting in an ellipse that rotates clockwise with the point $(U(t_0), V(t_0))$ in the second quadrant of the U-V Cartesian coordinate.

Note that in this particular example of FIG. 18, as well as in FIGS. 19, 20 and 21, we have assumed that the Cartesian coordinate axes U and V are aligned with the quadrant detector axis x and y, and at the same time, we have also assumed that the astigmatic axis is along the x or y axis as well. Therefore the ellipse as shown in FIGS. 18 to 21 is oriented horizontal or vertical.

If the major and minor axes are both negative, we can express them as −a and −b. In this case as shown in FIG. 19, the corresponding sequential ellipse is expressed by $U(t)=-a \cdot \cos(t)$, $V(t)=-b \cdot \sin(t)$, with $a>b>0$, both −a and −b negative. This will result in an ellipse that still rotates counter-clockwise. This can be considered as representing an overall convergent wavefront with both spherical and cylindrical refractive error components where the degree of convergence is different for the horizontal and vertical directions. If $a=b$, it would represent a convergent spherical wavefront where the degree of convergence is the same for the horizontal and vertical directions. With a $t_0$ value of $0<t_0<\pi/2$, the point $(U(t_0), V(t_0))$ will now be in the third quadrant of the U-V Cartesian coordinate, on the opposite side of the coordinate origin as compared to that of FIG. 18.

If the major axis is positive and the minor axis is negative, we can express them as a and −b. In this case as shown in FIG. 20, the corresponding sequential ellipse is expressed by $U(t)=a \cdot \cos(t)$, $V(t)=-b \cdot \sin(t)$, with $a>b>0$, a positive, and −b negative. This will result in an ellipse that rotates clockwise starting from the fourth quadrant. This can be considered as representing a horizontally divergent and vertically convergent wavefront with both spherical and cylindrical refractive error components where the degree of horizontal divergence and vertical convergence are different. If $a=b$, it would represent a horizontally divergent and vertically convergent cylindrical wavefront where the degree of horizontal divergence and vertical convergence are the same. With a $t_0$ value of $0<t_0<\pi/2$, the point $(U(t_0), V(t_0))$ will now be in the fourth quadrant of the U-V Cartesian coordinate.

If the major axis is negative and the minor axis is positive, we can express them as $-a$ and $b$. In this case as shown in FIG. 21, the corresponding sequential ellipse is expressed by $U(t)=-a\cdot\cos(t), V(t)=b\cdot\sin(t)$, with $a>b>0$, $-a$ negative, and b positive. This will result in an ellipse that rotates clockwise starting from the second quadrant. This can be considered as representing a horizontally convergent and vertically divergent wavefront with both spherical and cylindrical refractive error components where the degree of horizontal convergence and vertical divergence are different. If $a=b$, it would represent a horizontally convergent and vertically divergent cylindrical wavefront where the degree of horizontal convergence and vertical divergence are the same. With a $t_0$ value of $0<t_0<\pi/2$, the point $(U(t_0), V(t_0))$ will now be in the second quadrant of the U-V Cartesian coordinate, on the opposite side of the coordinate origin as compared to that of FIG. 20.

Figure 22:
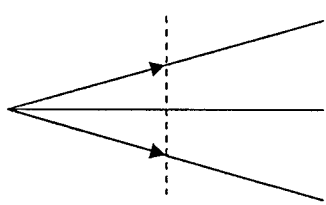
FIG. 22 shows an example of the sequential centroid data points expected from a divergent spherical wavefront and the resulting data point position and polarity.
Figure 22:
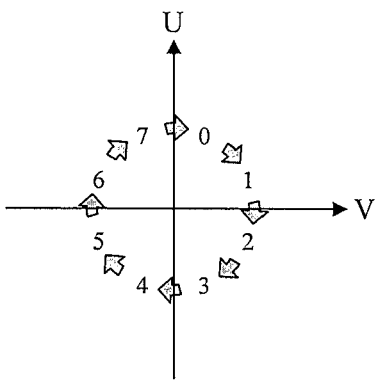
Figure 23:
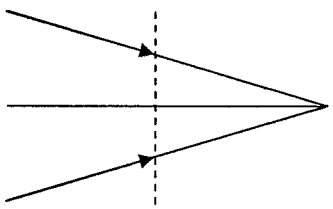
FIG. 23 shows another example of the sequential centroid data points expected from a convergent spherical wavefront and the resulting data point position and polarity.
Figure 23:
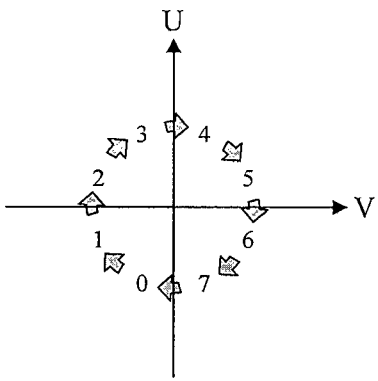

Note that the assignment of divergent wavefront to "positive" versus "negative" axis is arbitrary and can be reversed, as long as we distinguish between them. The positive direction of the axes can also be swapped. For example, the U axis can be pointing upward instead of pointing to the right and the V axis can be pointing to the right instead of pointing upward. In this case, as shown in FIG. 22, the sequential centroid data points expected from a divergent spherical wavefront sampled at the plane represented by the dashed line will be a clockwise circle with the resulting data point position and polarity as indicated by the numbers and the arrows in FIG. 22. Note that the sequential rotation direction is changed as compared to that of FIG. 18 due to a different assignment of the axis polarity. Similarly, in the same case, the sequential centroid data points expected from a convergent spherical wavefront sampled at the plane represented by the dashed line as shown in FIG. 23 will be a clockwise circle with the resulting data point position and polarity as indicated by the numbers and the arrows in FIG. 23. Note the swapping of the numbered data points from the original position in FIG. 22 to the opposite position in FIG. 23 when the sampled wavefront changes from being divergent to being convergent.

One embodiment of the present disclosure is to use a calibration (internal or external) to determine the initial offset angle of the data point vector(s) relative to the Xtr or Ytr axes. Another embodiment of the present disclosure is to rotate the Cartesian coordinate (Xtr, Ytr) to another Cartesian coordinate (U, V) by the offset angle so that at least one of the calibration centroid data point, for example, the i=0 data point $(U(0), V(0))$, is aligned on either the U or the V axis of the new Cartesian coordinate U-V. In this manner, the measured sub-wavefront tilts, now expressed as data points $(U(i), V(i))$, where $i=0, 1, 2, \ldots, 7$, with at least one of the data points aligned on either the U or V axis, can be easily correlated to an ellipse and/or averaged as if they are on a correlated ellipse, with the ellipse parameters correlated to the spherical and cylindrical diopter values of the sampled wavefront and with the major and/or minor axis direction correlated to the cylinder axis of the sampled wavefront.

Figure 24:
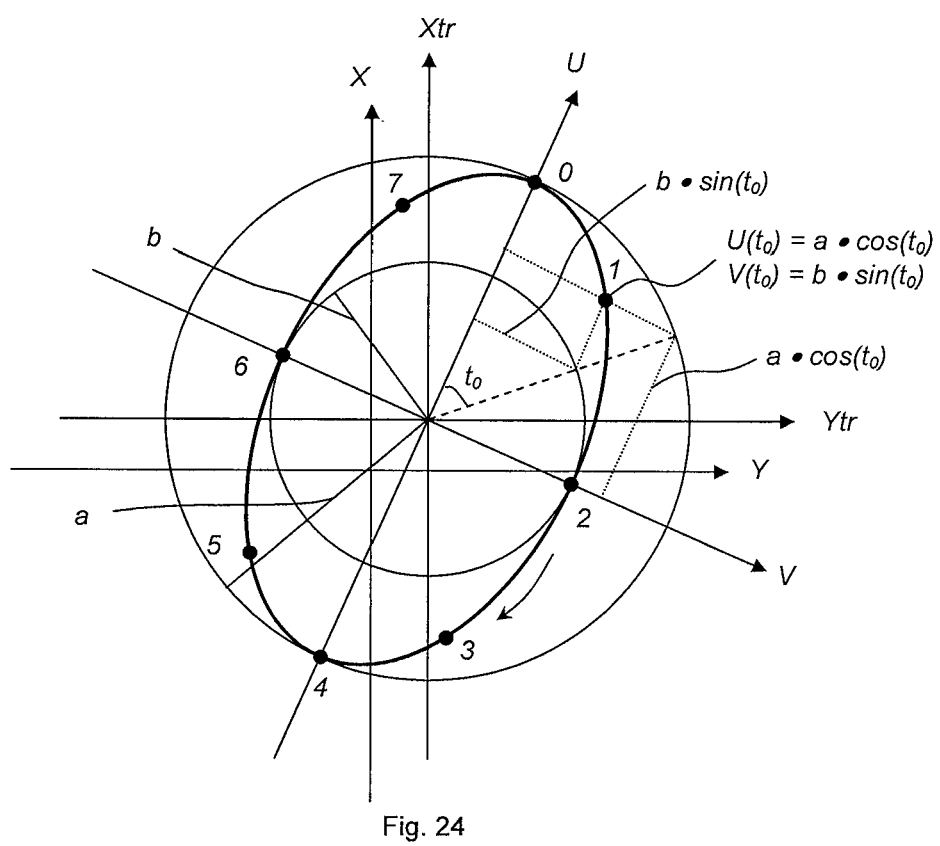
FIG. 24 shows the Cartesian coordinate translation and rotation from the original X-Y coordinate to the translated Xtr-Ytr coordinate and further rotated to the U-V coordinate of 8 sequentially sampled centroid data points that are fitted to a sequential ellipse.

FIG. 24 shows the Cartesian coordinate translation and rotation from the original X-Y coordinate to the translated Xtr-Ytr coordinate and further rotated to the U-V coordinate of 8 sequentially sampled centroid data points that are fitted to a sequential ellipse. Note that for an overall divergent wavefront and the shown coordinate axes selection, the sequential rotation direction is clockwise. In this example, the center of the 8 sequentially obtained data points is firstly determined and the X-Y coordinate is translated to the Xtr-Ytr coordinate where the origin of the Xtr-Ytr coordinate is the center of the 8 sequentially obtained data points. Then the major and minor axes of the fitted ellipse (with their corresponding axis polarity as discussed before) are obtained through digital data processing and coordinate rotation is performed by aligning the major or minor axis of the fitted ellipse to the U or V axis of the U-V coordinate that has the same origin as the Xtr-Ytr coordinate. Note that in this example, the first data point (point 0) is already aligned with or located on the U axis. In a more general situation, this may not be the case. However, if aligning the first data point (point 0) with the U axis helps data processing, the firing time of the SLD relative to the driving signal of the MEMS scanner can be adjusted to enable this alignment and the phase delay between the two signals can be used for the simplification of data processing.

The presently disclosed wavefront sampling example around an annular ring, the coordinate transformation, and the associated data processing have the benefit that the sphero-cylinder diopter values can be simply expressed analytically as a function of the $(U(i), V(i))$ data point values and as such, the data processing can be substantially simplified and executed extremely fast. In other words, the data points $(U(i), V(i))$ can now be easily fitted to an ellipse in canonical position (center at origin, major axis along the U axis) with the expression $U(t)=a\cdot\cos(t)$ and $V(t)=b\cdot\sin(t)$, where a and b are the major axis and the minor axis respectively and can have positive or negative values.

This algorithm enables real time high precision measurement of eye wavefront over a large dynamic range. When the U, V axes are rotated to fit the ellipse to the canonical position the orientation of the ellipse indicates the axis of astigmatism. Further, the magnitudes of a and b indicate the relative magnitudes of the divergent and convergent astigmatic components and the direction of rotation helps identifies which component is divergent and which component is convergent. As a result, real time titration of a surgical vision correction procedure can be performed. In particular, the real time wavefront measurement results can be used to direct, and/or align, and/or guide the operation of limbal relaxing incision (LRI) and/or astigmatic keratotomy (AK), as well as toric IOL (intraocular lens) rotation titration.

Figure 25:
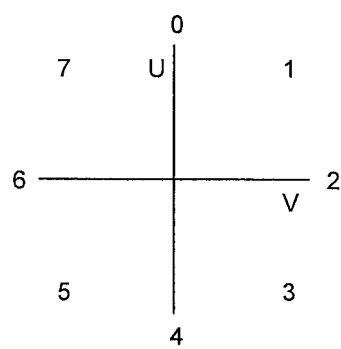
FIG. 25 shows the result of coordinate rotation transformation and 8 centroid data points on the U-V coordinate, with the left side corresponding to a divergent spherical wavefront having positive major and minor axes, and with the right side corresponding to a convergent spherical wavefront, having negative major and minor axes.
Figure 25:
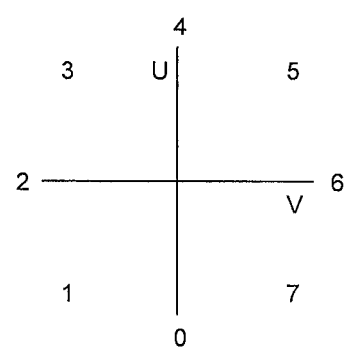

FIG. 25 shows a special case of FIG. 24, the result of coordinate rotation transformation and 8 centroid data points on the U-V coordinate, with the left side corresponding to a divergent spherical wavefront having equal positive major and minor axes, and with the right side corresponding to a convergent spherical wavefront, having equal negative major and minor axes. Note again the swapping of the numbered data points from the original position to the opposite position when the sampled wavefront changes from being divergent to being convergent.

When there is an astigmatic component superimposed onto a spherical component, a number of centroid data point trace scenarios occur, depending on the degree of the astigmatic wavefront tilt compared to that of the spherical wavefront tilt as has been discussed in co-assigned U.S. Pat. No. 7,445,335 and co-assigned U.S. Pat. No. 8,100,530. With the above-mentioned Cartesian coordinate transformations, the centroid data points can trace out a pattern centered at the origin of the U-V coordinate with at least one of the data points aligned with either the U or the V axis, but with different elliptic shapes and orientations. The shapes of the pattern include a normal rotation ellipse with both positive major and positive minor axes, a straight line with a positive or negative major axis or with a positive or negative minor axis, an abnormal or reverse rotation ellipse with a negative major axis and positive minor axis or with a positive major axis and a negative minor axis, and an abnormal or reverse rotation circle with either a positive major axis and a negative minor axis or with a negative major axis and a positive minor axis.

Since we are measuring a sequential wavefront, in the circular trace case, we can distinguish between three different circular trace patterns (divergent spherical circle, convergent spherical circle, and the astigmatic reverse rotation circle) because axis polarity is determined by the order in which the wavefront samples are collected. In fact, the astigmatic reverse rotation circle is effectively correlated to an ellipse since one axis (major or minor) has a different sign or polarity than the other axis (minor or major). The orientation of the ellipse or straight line or the reverse rotation circle can be determined from the major or minor axis direction and can be at any angle between 0 and 180 degree, which is also the practice well accepted by optometrists and ophthalmologists. It should be noted that the assignment of the major and/or minor axis is arbitrary so there is no need for the absolute length of the major axis to be longer than that of the minor axis. The assignment is only meant to facilitate the calculation of refractive errors associated with a wavefront from an eye.

It should also be noted that in addition to sampling the wavefront around one annular ring, multiple annular rings of different diameters or multiple concentric annular rings of the wavefront can be sampled. In doing so, a 2D wavefront map can be obtained and presented to an end user. By dynamically changing the annular ring sampling size of the wavefront sensor, one can also confirm the aphakic condition of a subject throughout the entire corneal visual field.

In yet another embodiment, the MEMS scanning mirror can be operated to sample sub-wavefronts in a spiral pattern or concentric rings of varying radii, allowing the detection of higher-order aberrations. Zernike decomposition can be performed to extract all the wavefront aberration coefficients, including high order aberrations such as trefoil, coma, and spherical aberration. For example, coma can be determined by detecting a lateral shift of the wavefront as the scan radius is increased or decreased. If the number of samples per annular ring is evenly divisible by 3, then trefoil can be detected when the dots form a triangular pattern that inverts when the scan radius is increased or decreased.

The effective spacing between any two wavefront sampling points can be controlled by controlling the SLD firing time and the drive signal amplitude of the MEMS scan mirror. In addition to reducing the size of the sub-wavefront sampling aperture which can be achieved by the front end processing system if the aperture is electronically variable, higher spatial precision/resolution sampling of the wavefront can also be achieved by precisely controlling the SLD firing time and also reducing the SLD pulse width as well as increasing the precision in the control of the MEMS scan mirror amplitude or position. In this respect, the MEMS scan mirror can be operated in closed-loop servo mode with the MEMS mirror scan angle monitor signal being fed-back to the microprocessor and/or the electronics control system to control the scan angle drive signal to achieve better scan angle control precision. On the other hand, more averaging can be achieved by increasing the size of the sub-wavefront sampling aperture or even increasing the pulse width of the SLD. Therefore, another embodiment of the present disclosure is to use the electronics to control the SLD and the wavefront shifter/scanner to achieve either higher precision/resolution in spatial wavefront sampling or more averaging in spatial wavefront sampling. Higher precision/resolution spatial wavefront sampling is desired for high order aberration measurement and more averaged spatial wavefront sampling is desired for measuring the refractive errors of the wavefront in terms of the spherical and cylindrical dioptric values and the axis of cylinder or astigmatism.

It should be noted that the above mentioned Cartesian coordinate translation and rotation is only one of many possible coordinate system transformations that can be employed to facilitate the calculation of refractive errors and wavefront aberrations. For example, non-Cartesian coordinate such as polar coordinate or non-perpendicular axis based coordinate transformations can be used. Therefore, the scope of the concept of using coordinate transformation to facilitate the calculation of wavefront aberrations and refractive errors should not be limited to Cartesian coordinates. The transformation can even be between Cartesian coordinate and polar coordinate.

In practice, a wavefront from a patient eye can contain higher order aberrations in addition to sphere and cylinder refractive errors. However, for most vision correction procedures such as cataract refractive surgery, generally only the sphere and cylinder refractive errors are corrected. Therefore, the need for averaging is desired so that the best sphere and cylinder correction dioptric values and cylinder axis angle can be found and prescribed. The present disclosure is extremely suitable for such an application as by averaging and correlating the centroid trace(s) to one or more ellipse(s) over one or more annular rings, together with the polarity of major and minor axis taken into consideration when correlating the centroid data points to the ellipse(s), the resultant prescription given in terms of the sphere and the cylinder dioptric values as well as the cylinder axis has already included averaging the effect of higher order aberrations. On the other hand, the algorithm and data processing can also tell the end user how much higher order aberration there is in the wavefront by calculating how close the correlation of the centroid data points to the ellipse(s) is.

Figure 26:
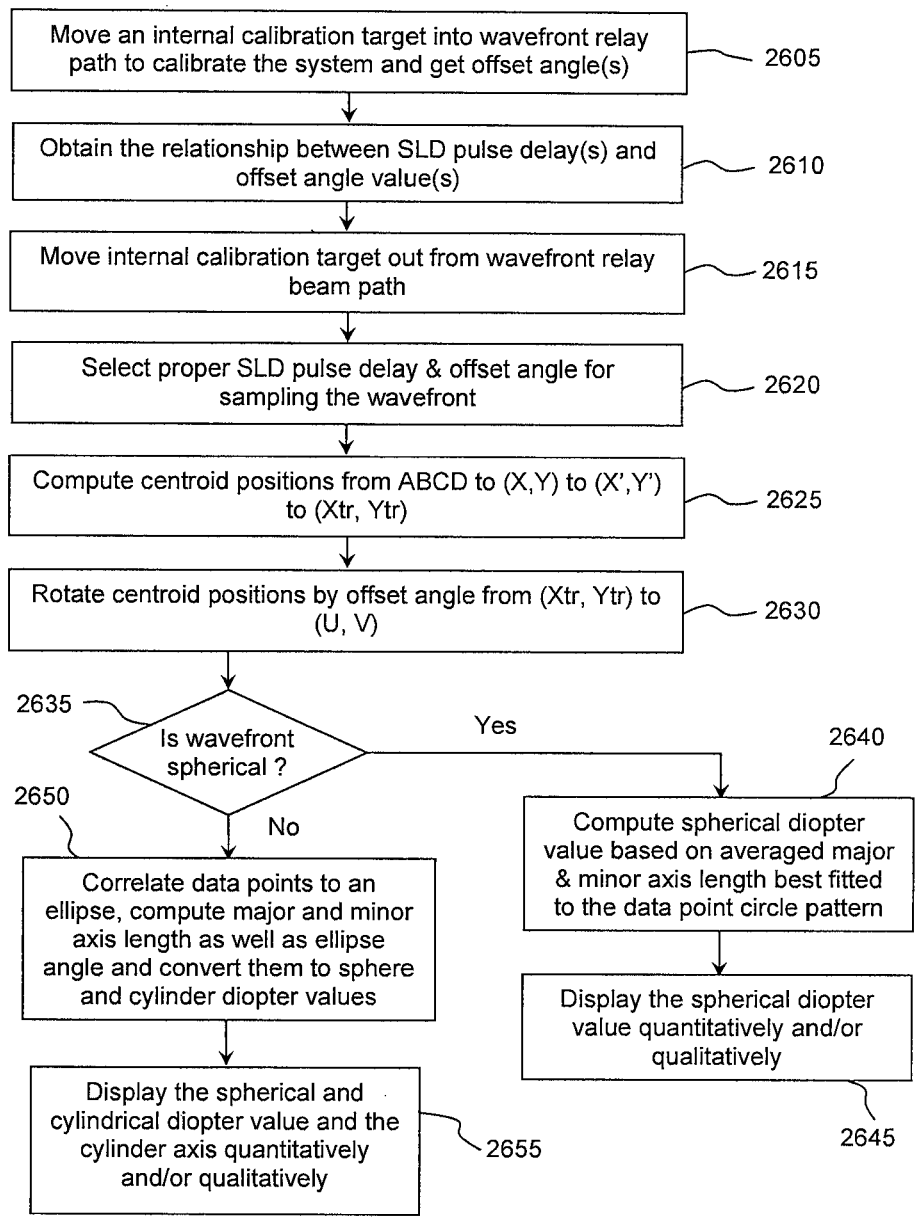
FIG. 26 shows the process flow diagram of one example embodiment in decoding the sphere and cylinder diopter values and the cylinder axis angle.

FIG. 26 shows the process flow diagram of one example embodiment in decoding the sphere and cylinder dioptric values and the cylinder axis angle. The calibration steps, including the step 2605 of moving an internal calibration target into the wavefront relay path to calibrate the system and getting the offset angle(s), the step 2610 of obtaining the relationship between SLD pulse delay(s) and the offset angle value(s), and the step 2615 of moving the internal calibration target out from wavefront relay beam path, can be performed once for many real eye measurements such as once per day before any measurement, or multiple times such as once before each eye measurement, as discussed before.

Once the offset angle information is obtained, there is an optional step 2620 to change or adjust the offset angle(s), which can be achieved by changing the SLD pulse delay or the initial phase of the sinusoidal and co-sinusoidal drive signal sent to the MEMS scan mirror. For example, with a spherical reference wavefront, the offset angle can be adjusted such that one of the centroid data point is aligned with the X or Y axis and in this case, there is no need to further conduct the coordinate rotation transformation. This can reduce the burden on data processing.

In the next step 2625, the centroid data point positions can be computed as discussed before from A, B, C, D values to ratiometric (X, Y) values, to modified centroid position values (X', Y'), and to translated centroid position values (Xtr, Ytr). The following step 2630, which involves coordinate rotation transformation from (Xtr, Ytr) to (U, V), can be optional if the SLD pulse delay relative to the MEMS mirror scanning can be controlled so that one of the centroid data point is already on the Xtr or Ytr axis.

In the next step 2635 in determining if the wavefront is spherical, we can compare the magnitude or length of some (such a perpendicular pair) or all the centroid data point vectors relative to the (Xtr=0, Ytr=0) or (U=0, V=0) origin in different ways. For example, if the standard deviation of all vector magnitudes or lengths is below a predetermined criteria value (for example, a value that corresponds to less than 0.25D cylinder), we can treat the wavefront to be spherical. Alternatively, we can compare the vector magnitudes of some or all the data point vectors and if their magnitudes are substantially equal and their difference is below a predetermined criteria value, then the wavefront can be considered as spherical.

In such a spherical wavefront case, as a following step 2640 as shown in FIG. 26, we can still correlate the data points to an ellipse, but in addition to calculating the major or minor axis length which will be substantially equivalent, we can average the major and minor axis length, and depending on the sign or polarity of the major and minor axis which can be both positive or negative, output an averaged positive or negative spherical diopter value. Note that the relationship between the dioptric value and the major or minor axis length can be and should have been obtained during the comprehensive calibration stage as has been discussed before.

An optional follow-up step 2645 is to display the computed spherical dioptric value quantitatively as a number and/or qualitatively as circle, with the circle diameter or radius representing the absolute spherical dioptric value, and with the sign of the sphere being shown using for example a different color or line pattern for the circle.

On the other hand, if the wavefront is found not spherical, we can assume that there is an astigmatic component. As a follow-up step 2650, we can correlate the data points to an ellipse and calculate the major and minor axis length with polarity as the value can be positive or negative, as well as an ellipse angle which can be either the major or minor axis angle. Having calculated the ellipse angle, the major and minor axis lengths, we can compute sphere and cylinder dioptric values using the experimentally obtained calibration relationship or a look-up table. It is preferred that the diopter values are monotonically related to the major and minor axis length (with polarity or sign information included) so that there are only unique solutions for a certain ellipse. As in the case of spherical wavefront, an optional follow-up step 2655 is to display the computed spherical and cylindrical dioptric values and the cylinder axis quantitatively as a set of numbers and/or qualitatively as a circle plus a straight line, with the circle diameter representing the sphere dioptric value, with the straight line length representing the cylinder dioptric value, and with the straight line orientation angle which can be indicated by a long thin or dashed line or an arrow, representing the cylinder axis angle. Alternatively, the qualitative display can also be in the form of an ellipse with either the major or the minor axis length representing the sphere dioptric value, with the difference in major and minor axis length (polarity considered) representing the cylinder dioptric value, and with the ellipse orientation angle representing the cylinder axis angle. Again, the sign of the sphere and cylinder dioptric value can be shown using, for example, a different color or a different line pattern for the circle-plus-straight-line representation or for the ellipse representation. One embodiment of the present disclosure is to allow user selection of an ellipse or a circle-plus-straight-line to represent the refractive errors of a patient eye.

It should be noted that there can be many other ways to qualitatively display the refractive errors. The above mentioned qualitative representations are only illustrative rather than comprehensive. For example, the representation can also be an ellipse with its major axis proportional to one independent cylinder diopter value and its minor axis proportional to another independent and perpendicular cylinder diopter value. In addition, the axis angle representing one cylinder or the other cylinder angle can be the original angle or shifted by 90°, as the cylinder axis angle can be either the major axis angle or the minor axis angle depending on whether the end user prefers a positive or negative cylinder prescription. Alternatively, the representation can also be two orthogonal straight lines with one straight line length proportional to one independent cylinder dioptric value and the other orthogonal straight line length proportional to the other independent and perpendicular cylinder dioptric value.

As mentioned before, one embodiment of the present disclosure is the overlay, on the live video image of the patient's eye, of the wavefront measurement result in a qualitative and/or quantitative way. The displayed ellipse or straight-line angle can also be dependent on the orientation of the surgeon/clinician relative to the patient's eye (superior or temporal), and if temporal, which of the patient's eyes is being imaged (right or left). For cataract surgery, it is preferred that the cylinder axis presented to a cataract surgeon is aligned with the steeper axis of the cornea so that the surgeon can conduct LRI (Limbal Relaxing Incision) based on the presented axis direction.

The live eye image can be processed with a pattern recognition algorithm to achieve eye registration for supine or vertical patient position and/or to determine the axis of an implanted tonic IOL referenced to iris landmarks such as crypt. In addition, the live image can also be used to identity particular lens (natural or artificial) registrations for alignment and/or comparison of optical signals (from, for example, wavefront and/or OLCI/OCT measurement) to physical features of the eye lens or iris.

Also note that the conversion from the correlated ellipse major and minor axis length to the diopter values can be done in different ways depending on the preference of the end user. As is well known to those skilled in the art, there are three ways to represent the same refractive error prescription. The first is to represent it as two independent perpendicular cylinders, the second one is to represent it as sphere and a positive cylinder, and the third one is to represent it as a sphere and a negative cylinder. In addition, the representation can be with respect to either prescription or the actual wavefront. Our correlated ellipse actually directly provides the dioptric values of the two independent perpendicular cylinders. As for the conversion from one way of representation to another, it is well known to those skilled in the art. What needs to be emphasized is that one embodiment of the present disclosure is the use of both positive and negative values to represent the major and minor axis of the correlated ellipse and the calibration approach to correlate the major and minor axis length, which can be either positive or negative, to the two independent perpendicular cylinder dioptric values which can also be positive or negative.

Note that optometrists, ophthalmologists, and optical engineers may represent the same wavefront at the cornea or pupil plane of a patient eye using different ways. For example, an optometrist generally prefers a prescription representation which is the lens(se) to be used to cancel out the wavefront bending to make it planer or flat; an ophthalmologist tends to prefer a direct representation which is what the wavefront at the eye cornea plane is in terms of sphere and cylinder dioptric values and cylinder axis; while an optical engineer would generally not use dioptric values but a wavefront map that shows the 2D deviation of the real wavefront from a perfect planar or flat wavefront, or a representation using Zernike polynomial coefficients. One embodiment of the present disclosure is the mutual conversion between these different representations that can be carried out by the end user as the algorithm has been built in the device to do such conversion, so it is up to the end user to select the format of the representation.

In terms of further improving the signal to noise ratio and hence measurement accuracy and/or precision, the ellipse or circle-plus-straight-line correlation can be done for one frame (or set) of data points or multiple frames (or sets) of data points. Alternatively, the obtained sphere and cylinder dioptric values as well as the cylinder axis angle can be averaged over multiple captures. For example, the averaging can be accomplished simply by adding respectively a given number of sphere and cylinder dioptric values of multiple measurements and dividing by the given number. Similarly, the cylinder angle can also be averaged although it can be more involved because of the wrap-around problem near 0°, as we report angles from 0° to 180°. As one approach, we use trigonometric functions to resolve this wrap-around issue.

It should be noted that the front-end processing system as indicated in FIG. 7 also controls the international fixation target in addition to other LEDs. However, the internal fixation does not need to be limited to a single LED or a single image such as a back-illuminated hot air balloon. Instead, the internal fixation target can be a micro-display combined with an eye accommodation enabling optical element such as a focus variable lens. The patient eye can be made to fixate at different directions by lighting up different pixels of the micro-display so that peripheral vision wavefront information such as a 2D array of wavefront maps can be obtained. In addition, the patient eye can be made to fixate at different distances to enable the measurement of the accommodation range or amplitude. Furthermore, the fixation micro-display target can be controlled to flash or blink with various rates or duty cycles, and the micro-display can be a colored one to enable fixation target to change color and to light-up pattern or spots.

Figure 27:
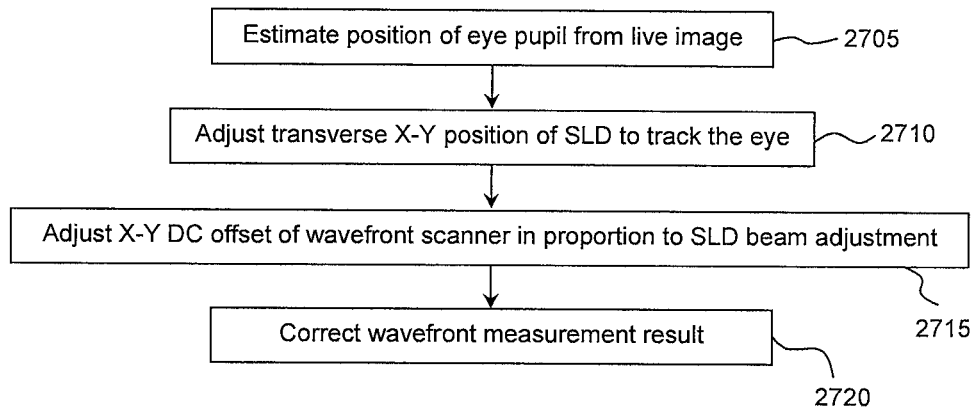
FIG. 27 shows an example process flow diagram of an eye tracking algorithm.

As mentioned before, one embodiment of the present disclosure is in tracking the eye. FIG. 27 shows an example process flow diagram of an eye tracking algorithm. The steps involved include step 2705 of estimating the position of the eye pupil using either the eye pupil position information from the live eye pupil or iris image or other means such as detecting specular reflection from the cornea apex by scanning the SLD beam in two dimensions; step 2710 of adjusting the SLD beam scanner to follow the eye movement; step 2715 of offsetting the DC drive component of the wavefront scanner/shifter in proportion to the SLD beam adjustment to compensate the eye pupil movement so that the same intended portions of the wavefront from the eye are always sampled regardless of the eye movement; and as an option, step 2720 of correcting the measurement of wavefront aberration. The live image camera provides a visual estimate of either (a) the center of the iris, or (b) the center of the corneal limbus. By correlating the SLD beam (X, Y) positions to the visual field of view, the SLD can be directed to the same position on the cornea. Typically for wavefront sensing, this position is slightly off the axis or apex of the cornea as in this way, specular reflection of the SLD beam will generally not be directly returned to the position sensing detector/device of the wavefront sensor. The center of the iris or the center of the limbus can be used as a reference point to directing the SLD beam.

Note that a unique feature of the presently disclosed algorithm is the step of offsetting the DC drive component of the wavefront scanner/shifter in proportion to the SLD beam adjustment. This is a critical step as it can ensure that the same portions of the wavefront (such as the same annular ring of the wavefront) from the eye are sampled. Without this step, as the eye is transversely moved, different portions of the wavefront from the eye will be sampled and this can cause significant wavefront measurement errors. The reason why the last step of correcting the measurement of wavefront aberration is optional is that with the compensation that can be provided by the wavefront scanner/shifter in proportion to the SLD beam adjustment, the consequence to the wavefront measurement is that there will be added astigmatism and/or prismatic tilt and/or other know aberration components to all the sampled portions of the wavefront which can be pre-determined and taken into consideration. We have shown that our refractive error decoding algorithm can automatically average the aberration to figure out compromised sphere and cylinder and to filter out the prismatic tilt through coordinate translation, so for refractive error measurements, there is no additional need for prismatic tilt correction. In spite of the fact that the amount of coordinate translation is already an indication of the prismatic tilt of the wavefront from the eye, for a complete wavefront measurement which should include the prismatic tilt, this additional astigmatism and/or prismatic tilt and/or other know aberration components caused by eye tracking should be subtracted out, so the last correction step might still be needed.

Another embodiment of the present disclosure is in adaptively selecting the diameter of the wavefront sampling annular ring so that while wavefront sampling is only performed within the eye pupil area, the slope sensitivity of the response curve as a function of the annular ring diameter can also be exploited to provide higher measurement sensitivity and/or resolution. In general, among all the dioptric values of different wavefront aberrations such as sphere, cylinder and trefoil, the sphere dioptric value generally requires the largest coverage range as it can vary a lot among different eyes as well as during a cataract surgery when the natural eye lens is removed (i.e. the eye is aphakic). On the other hand, when a cataract surgery is completed or near completion with an IOL (intraocular lens) implanted in the eye, the wavefront from the eye should be close to planar as the pseudo-phakic eye should in general be close to emmetropia. For a typical auto-refraction measurement, the wavefront from only the 3 mm diameter central area of the eye pupil is generally sampled. A wavefront sensor can therefore be designed to provide enough diopter measurement resolution (e.g. 0.1D) as well as enough diopter coverage range (e.g. −30D to +30D), over an effective wavefront sampling annular ring area that covers for example, a diameter range from 1 mm to 3 mm. Meanwhile, in order confirm emmetropia with higher sensitivity and/or wavefront measurement resolution, we can expand the wavefront sample annular ring to a diameter of, for example, 5 mm near the end of a cataract refractive surgery as long as the pupil size is large enough to more accurately measure the wavefront or refractive errors of a pseudo-phakic eye.

Figure 28:
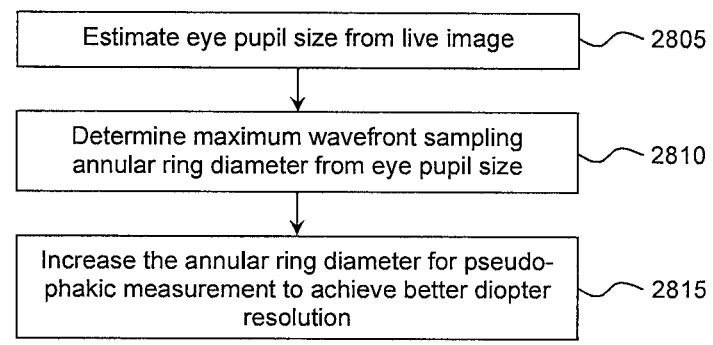
FIG. 28 shows an example process flow diagram illustrating the concept of using the live eye image to determine the maximum wavefront sampling annular ring diameter and to obtain better diopter resolution for pseudo-phakic measurement.

FIG. 28 shows an embodiment flow diagram of an algorithm that can implement this concept. The steps involved include the step 2805 of using the eye pupil information obtained from the live eye image to estimate the eye pupil size, the step 2810 of using the eye pupil size information to determine the maximum diameter of the wavefront sampling annular ring, and the step 2815 of increasing the annular ring diameter up to the maximum diameter as determined by step 2810 for pseudo-phakic measurement to achieve better diopter resolution. This "zoom in" feature could be user-selectable or automatic. In addition, we can also use the PSD ratiometric output to adaptively adjust the annular ring diameter for optimal dioptric resolution and dynamic range coverage.

Figure 29:
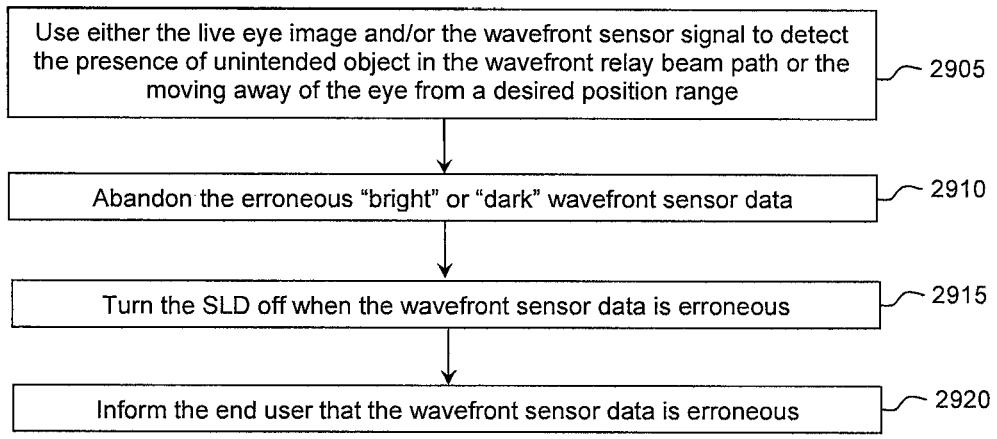
FIG. 29 shows an example process flow diagram illustrating the concept of using either the live eye image and/or the wavefront sensor signal to detect the presence of unintended object in the wavefront relay beam path or the moving away of the eye from a desired position range so that the SLD can be turned off and the erroneous "bright" or "dark" wavefront data can be abandoned.

One feature of the present disclosure is to combine the live eye image, with or without a pattern recognition algorithm, with the wavefront measurement data, to detect the presence of eye lids/lashes, iris, facial skin, surgical tool(s), surgeon's hand, irrigation water or the moving away of the eye from the designed range. In doing so, "dark" or "bright" data can be excluded and the SLD can be smartly turned on and off to save exposure time, which can enable higher SLD power to be delivered to the eye to increase the optical or photonic signal to noise ratio. FIG. 29 shows an example process flow diagram illustrating such a concept. The steps involved include the step 2905 of using either the live eye image and/or the wavefront sensor signal to detect the presence of unintended object in the wavefront relay beam path or the moving away of the eye from a desired position and/or range, the step 2910 of abandoning the erroneous "bright" or "dark" wavefront data, the step 2915 of turning the SLD off when the wavefront data is erroneous, and an optional step 2920 of informing the end user that the wavefront data is erroneous or invalid.

Another embodiment of the present disclosure is in scanning and/or controlling the incident SLD beam across a small area on the retina to remove speckles, do averaging, and also potentially allow an increase in the optical power within the safety limit that can be delivered into the eye, which can increase the optical signal to noise ratio. In addition, the SLD beam divergence/convergence and hence the size of the SLD beam spot size on the retina can also be dynamically adjusted using, for example, an axially movable lens or a focus variable lens or a deformable mirror so that the SLD spot size on the retina can be controlled to enable a more consistent and/or well calibrated measurement of the wavefront from the eye. Meanwhile, the SLD beam spot size and/or shape on the retina can also be monitored using, for example, the same live eye image sensor by adjusting its focus or a different image sensor solely dedicated to monitoring the SLD beam spot on the retina of an eye. With such a feedback and the incorporation of a closed loop servo electronics system, the static or scanned pattern of the SLD spot on the retina can be controlled.

Still another embodiment of the present disclosure is to include a laser as a surgery light source that can be combined with the SLD beam to be launched through the same optical fiber or another free space light beam combiner that can use the same the SLD beam scanner or a different scanner to scan the surgery laser beam for performing refractive correction of the eye such as LRI (limbal relaxing incision). The same laser or a different laser can also be used to "mark" the eye or "guide" the surgeon, i.e. "overlaying" on the eye so that the surgeon can see the laser mark(s) through the surgical microscope.

Another embodiment of the present disclosure is in measuring the eye distance while the eye wavefront is being measured and in correcting the measurement of the wavefront from the eye when the eye distance is changed. The information on eye distance from the wavefront sensor module is especially important for a cataract refractive surgery because when the natural lens of the eye is removed, i.e. the eye is aphakic, the wavefront from the eye is highly divergent, and as a result, a small axial movement of the eye relative to the wavefront sensor module can induce a relatively large change in the refractive error or wavefront aberration measurement. We have discussed how a correction to the wavefront can be done if the eye is transversely moved away from the designed position. A similar correction should also be made when the eye is axially moved away from its designed position. In doing the axial correction, either a low optical coherence interferometer (LOCI) or an optical coherence tomographer (OCT) can be included in the wavefront sensor module and be used to measure the eye axial distance. Alternatively, a simpler technique of using optical triangulation to measure the eye distance can also be employed. LOCI and OCT are preferred because in addition to eye distance, they can also do eye biometric/anatomic measurements. These measurements are especially valuable to eye refractive surgery as they can also reveal the effective lens (natural or artificial) position, if there is tilt in the lens, the anterior chamber depth, the thickness of the cornea and the lens and also the eye length. With transverse scanning as can be achieved by an OCT system, even the corneal and/or eye lens (natural or artificial) refractive power can be derived in tandem or independently, especially for the case of an aphakic eye.

Still another embodiment is to combine two or more of the measurement results obtained by the wavefront sensor, the eye imaging camera and the LOCl/OCT for other purposes. In one embodiment, the combined information can be used to detect optical scattering and/or opacity within the media of the ocular system, such as cataract opacity and the presence of optical bubbles in the eye, especially after the natural eye lens has been fractured by a femto-second laser. The combined information can also be used to detect the aphakic state of the eye and to calculate the IOL prescription needed for target refraction in real time in the operating room (OR) either on demand or right before the IOL is implanted, and/or to confirm the refraction, and/or to find out the effective lens position right after the IOL is implanted. Furthermore, the combined information can also be used to determine the alignment of the patient head, i.e. to determine if the eye of the patient is normal to the optical axis of the wavefront sensor module. In addition, the combined information can also be used to perform dry eye detection and to inform the surgeon when to irrigate the eye. Moreover, the combined information can also be displayed per the customization by the clinician/surgeon in order to present to him/her only the preferred information, such as eye refractive errors before surgery, IOL prescription at the aphakic state, and end point indicator to indicate for example, if a targeted eye refraction is reached at the end of a surgery, or if a multi-focal IOL is properly centered without significant tilt, or when a toric IOL is implanted, if it is centered and rotated to the correct axis angle. The display can also show a data integrity indicator or a confidence indicator.

The combined information can further be used to determine if the eye is aligned well, and if not, to include a directional guide in the display to tell a surgeon/clinician which way to move the patient eye or the microscope for better alignment. The information can also be used to indicate if the eye lid is closed, or if there is/are optical bubble(s) or remains of fractured/ruptured eye lens material inside the eye bag that may affect the wavefront measurement result, and to include confidence indicators in the display to indicate if the wavefront measurement is qualified.

Referring back to FIG. 2, it can be noted that the sub-wavefront focusing lens 220 can also be controlled by the electronics system. This lens can be a focus variable lens or an axially movable lens or even a deformable mirror. The purpose of making this lens active is to dynamically adjust its focal length in either an open loop or a closed control loop manner so that the image/light spot size formed by the sub-wavefront focusing lens can be controlled based on the local divergence or convergence of the sequentially sampled sub-wavefront. This is especially true when wavefront sampling is performed around an annular ring. For example, to achieve better response slope sensitivity for better wavefront tilt measurement in precision and/or accuracy, the image spot can be better focused on a the PSD (quadrant detector or lateral effect position sensing detector) that is used to determine the transverse movement of the image spot. Alternatively, the image spot of the sampled sub-wavefront landing on the PSD (quadrant detector or lateral effect position sensing detector) can also be controlled to a certain desired size. For example, one choice for the spot size is that of a single quadrant of a quadrant detector as is well known to those skilled in the art. Another possible choice is a size that produces a compromised high sensitivity and large dynamic response range. Still another choice is an image spot size about twice the gap size of the quadrant detector. These different image spot sizes can be dynamically varied depending on the averaged local divergence or convergence of the sequentially sampled sub-wavefront.

By dynamically compensating the wavefront or DC offsetting the defocus of the wavefront, the image spot can also be made to always land at or near the center of the quadrant detector. With this approach, one should be able to lock and null the image spot of each sampled sub-wavefront in size and position so that the highest sensitivity can be achieved. The drive signal for the wavefront compensating or defocus offsetting device, the wavefront shifter and the sub-wavefront focusing lens can be used to precisely determine the wavefront tilt of each sampled sub-wavefront.

It should be noted that the presently disclosed apparatus can accomplish a large number of additional tasks depending on the configuration of the host computer that processes the wavefront data, the eye image data, the eye distance data, the low coherence interferometer data, etc. For example, the host computer can be configured to analyze the wavefront data to obtain metrics such as refractive errors, to display the metrics qualitatively and/or quantitatively on the display, and to allow the surgeon/clinician to select the manner in which the qualitative and/or quantitative metrics is to be displayed. In terms of how the wavefront measurement should be displayed, the end user can opt for display of wavefront aberration versus refraction versus prescription, and/or positive cylinder versus negative cylinder, and/or end point indicator(s) such as emmetropia.

The host computer can also be configured to allow the surgeon/clinician to flip or rotate the live patient eye image/movie to a preferred orientation. In addition, the surgeon/clinician can also rewind and replay desired recorded segments of a composite movie that may include the eye image, the wavefront measurement result and even the low coherence interferometry measurement results, on demand during or after the surgery.

Most importantly, the present disclosure can guide a surgeon to titrate the vision correction procedure in real time to optimize the vision correction procedure outcome. For example, it can guide a surgeon in adjusting the IOL position in the eye in terms of centration, tilt and circumferential angular orientation positioning until the measurement confirms optimal placement of the IOL. Moreover, it can guide a surgeon in rotating an implanted toric intraocular lens (IOL) to correct/neutralize astigmatism. It can also guide a surgeon in conducting limbal/corneal relaxing incision or intrastromal lenticule laser (Flexi) to titrate and thus neutralize astigmatism.

The presently disclosed apparatus can also be used to indicate whether an implanted multi-focal IOL has the desired focusing range in addition to optimizing its positioning. It can also be used to measure whether an implanted AIOL (accommodating or accommodative IOL) can provide a desired accommodation range.

On the display, a real time guide can be provided on how a vision correction procedure should proceed in order to facilitate removal of remaining aberration(s), confirm the results, and document the value and sense of the aberrations. The real time information displayed can also be digitally "zoomed out" or "zoomed in" automatically or manually to alert a surgeon or vision correction practitioner that the correction procedure is going in the wrong or right direction. When a certain level of correction has been reached, the displayed information can turn into a highlighted form in terms of, for example, font size, boldness, style or color, to confirm intraoperatively that a refractive endpoint goal for a patient such as emmetropia has been reached.

In addition to visual feedback, audio feedback can also be used solely or in combination with video feedback. For example, audio information can be provided with or without video/graphic information to indicate which direction to move an IOL for proper alignment or which direction to rotate a toric lens to correct/neutralize astigmatism. Also a real-time audio signal can be generated to indicate the type of refractive error, magnitude of error, and change in error. The pitch, tone and loudness of the real-time audio signal can be varied to indicate improvement or worsening of applied corrections during the vision correction procedure. A specific pitch of the real-time audio signal can be created to identify the error as, for example, cylinder with a tone that indicates the magnitude of the cylinder error.

One very important application of the present disclosure is in helping a cataract surgeon in determining, at the aphakic state of a patient's eye, if the pre-surgery selected IOL power is correct or not. The real time aphakic wavefront measurement (preferably together with the eye biometry measurement such as that provided by a built-in low coherence interferometer) can more accurately determine the IOL power needed and thus confirm whether the IOL power selected pre-surgically is correct or not, especially for patients with post-op corneal refractive procedures for whom the pre-surgery IOL selection formulas do not deliver consistent results.

Another important application of the present disclosure is in monitoring and recording of the changes in the cornea shape and other eye biometric/anatomic parameters during the whole session of a cataract surgery while the wavefront from the patient eye is measured. The changes can be measured before, during, and after a cataract surgery in the OR (operating room) and can be in corneal topography and thickness as can be measured with keratometry and pachymetry, anterior chamber depth, lens position and thickness, as a result of various factors that can cause a change in the wavefront from the patient eye. These factors include, for example, topical anesthesia, eye lid speculum, incision/wound made in the cornea, anterior chamber filling material, intra-ocular pressure, water/solution irrigation onto the cornea, wound sealing, even wound healing effect and surgeon induced wavefront change effect resulting from surgeon specific cataract surgery practice.

The data on the change in the eye biometric/anatomic parameters can be used to compensate for the effects induced by the various factors. The wavefront outcome after the healing of the incision/wound can thus be predicted and be used to set certain desired target eye refraction for the cataract surgery. The right-before-surgery and right-after-surgery cornea shape and other eye biometric/anatomic parameters can be measured using the built-in OCT and eye camera and a built-in or external corneal topographer/keratometer that can be attached either to a surgical microscope or the presently disclosed apparatus. The right-before-surgery measurement can be done in the OR when the patient is in the supine position before and after topical anesthesia is applied, before and after an eye lid speculum is engaged to keep the eye lids open. The during-surgery measurements can be done in the OR after incision(s) is(are) made in the cornea, after the cataract lens is removed and the anterior chamber is filled with a certain gel (OVD, Ophthalmic Viscosurgical Device) before an artificial intraocular lens is implanted, after an IOL is implanted but before the incision wound is sealed. The right-after-surgery measurement can be done in the OR as well when the patient is still in the supine position right after the surgeon has sealed the incision/wound but before the eye lid speculum is removed, and after the eye lid speculum is removed.

The data thus obtained on the changes in the cornea shape and other eye biometric/anatomic parameters can be combined with the ocular wavefront measurement data and be saved in a data base. Another round of measurements can be done after the incision(s)/wound has/have completely healed weeks or months after the surgery and the difference or change in the ocular wavefront and the cornea shape and/or the eye biometry parameters can also be collected. A nominal data base can therefore be established and processed to figure out the target refraction right after a cataract surgery that needs to be set in order to result in a final desired vision correction outcome after the wound has completely healed. In this way, all the effects, including even surgeon-induced aberrations such as astigmatism resulting, for example, from a particular personalized cornea incision habit, would have been taken into consideration.

The presently disclosed wavefront sensor can be combined with a variety of other ophthalmic instruments for a wide range of applications. For example, it can be integrated with a femto-second laser or an excimer laser for LASIK, or eye lens fracturing, or for alignment and/or guidance on "incision", or for close loop ablation of eye tissues. The live eye image, OLCI/OCT data, and the wavefront data can be combined to indicate if optical bubble(s) is/are present in the eye lens or anterior chamber before, during and after an eye surgical operation. Alternatively, the wavefront sensor can also be integrated with or adapted to a slit lamp bio-microscope.

The present invention can also be integrated or combined with an adaptive optics system. A deformable mirror or LC (liquid crystal) based transmissive wavefront compensator can be used to do real time wavefront manipulation to compensate some or all of the wavefront errors partially or fully.

In addition, the presently disclosed wavefront sensor can also be combined with any other type of intra-ocular pressure (IOP) measurement means. In one embodiment, it can even be directly used to detect IOP by measuring the eye wavefront change as a function of a patient's heart beat. It can also be directly used for calibrating the IOP.

These embodiments could also be deployed to measure optics, spectacles and/or glasses, IOL and/or guide the cutting/machining devices that create the optics. These embodiments could also be adapted to microscopes for cell and/or molecular analysis or other metrology applications. The present invention can also be used for lens crafting, spectacle confirmation, micro-biology applications etc.

Although various embodiments that incorporate the teachings of the present invention have been shown and described in detail herein, those skilled in the art can readily devise many other varied embodiments that still incorporate these teachings.

What is claimed is:

1. A wavefront sensor comprising:
   a light source configured to output a light beam to illuminate a subject eye;
   a light source driver circuit coupled to the light source, configured to output a light source drive signal at a first pulsing frequency;
   a position sensitive detector having a plurality of detector elements configured to output a plurality of detector output signals indicating signal strength of incident light on each detector element;
   a beam deflecting element configured to intercept a wavefront beam returned from a subject eye when the subject eye is illuminated by the light source and configured to direct a portion of the wavefront beam from the subject eye through an aperture toward the detector, where the portion of the wavefront beam directed through the aperture forms a spot on the detector, where an amplitude of deflection of a centroid of the spot from a reference point on the detector is approximately indicated by a ratiometric combination of the signal strengths, and where the amplitude of the deflection indicates the degree of tilt or convergence or divergence of the portion of the wavefront from a plane wave;
   a beam deflecting element driving circuit, coupled to the beam deflecting element, configured to output a beam deflecting element drive signal to scan the portion of the wavefront beam at a wavefront scanning frequency; and
   a plurality of composite transimpedance amplifiers, each having an input coupled to receive one of the plurality of detector output signals and an output for providing an amplified detector output signal, with the output of each transimpedance amplifier phase-locked to the light source drive signal and the beam deflecting element drive signal.

2. The wavefront sensor of claim 1 with each composite transimpedance amplifier comprising a low pass filter to increase stability and reduce high frequency noise.

3. The wavefront sensor of claim 2 with the low pass filter comprising:
   a first operational amplifier U2A having an input and output;
   a first resistor R3; and
   a first capacitor C3 with the first resistor and capacitor connected in series between the input and output of the first operational amplifier.

4. The wavefront sensor of claim 3 with the composite transimpedance amplifier further comprising:
   a second operational amplifier U1A having an input and an output; and
   a feedback resistor R1, having a feedback resistance value, coupling the output of the first operational amplifier to the input of the second operational amplifier where the amplitude of the amplified detector output signal is proportional to R1 and the noise is proportional to the square root of R1.

* * * * *